US009611489B2

(12) United States Patent
Schaffer et al.

(10) Patent No.: US 9,611,489 B2
(45) Date of Patent: Apr. 4, 2017

(54) ENZYMATIC OMEGA-OXIDATION AND OMEGA-AMINATION OF FATTY ACIDS

(71) Applicants: Steffen Schaffer, Herten (DE); Michaela Hauberg, Essen (DE); Mirja Wessel, Bochum (DE); Hans-Georg Hennemann, Marl (DE); Jan Christoph Pfeffer, Hanau (DE); Thomas Haas, Muenster (DE); Harald Haeger, Luedinghausen (DE)

(72) Inventors: Steffen Schaffer, Herten (DE); Michaela Hauberg, Essen (DE); Mirja Wessel, Bochum (DE); Hans-Georg Hennemann, Marl (DE); Jan Christoph Pfeffer, Hanau (DE); Thomas Haas, Muenster (DE); Harald Haeger, Luedinghausen (DE)

(73) Assignee: EVONIK DEGUSSA GmbH, Essen (DE)

( * ) Notice: Subject to any disclaimer, the term of this patent is extended or adjusted under 35 U.S.C. 154(b) by 15 days.

(21) Appl. No.: 14/384,301

(22) PCT Filed: Mar. 12, 2013

(86) PCT No.: PCT/EP2013/054928
§ 371 (c)(1),
(2) Date: Sep. 10, 2014

(87) PCT Pub. No.: WO2013/135650
PCT Pub. Date: Sep. 19, 2013

(65) Prior Publication Data
US 2015/0111253 A1  Apr. 23, 2015

(30) Foreign Application Priority Data
Mar. 12, 2012 (EP) ..................... 12159087

(51) Int. Cl.
C12P 7/64 (2006.01)
C12N 9/04 (2006.01)
C12N 9/02 (2006.01)
C12N 9/10 (2006.01)
C12P 7/42 (2006.01)
C12P 7/62 (2006.01)
C07K 14/79 (2006.01)
C12N 9/06 (2006.01)
C12P 13/00 (2006.01)
C07K 14/21 (2006.01)

(52) U.S. Cl.
CPC ............ C12P 7/6436 (2013.01); C07K 14/21 (2013.01); C07K 14/79 (2013.01); C12N 9/0006 (2013.01); C12N 9/0016 (2013.01); C12N 9/0077 (2013.01); C12N 9/0095 (2013.01); C12N 9/1096 (2013.01); C12P 7/42 (2013.01); C12P 7/62 (2013.01); C12P 7/6409 (2013.01); C12P 13/005 (2013.01); C12Y 114/14001 (2013.01)

(58) Field of Classification Search
None
See application file for complete search history.

(56) References Cited

U.S. PATENT DOCUMENTS

| | | | |
|---|---|---|---|
| 6,620,970 B2 | 9/2003 | Schiffer et al. |
| 6,639,108 B2 | 10/2003 | Schiffer et al. |
| 6,861,540 B2 | 3/2005 | Herwig et al. |
| 6,878,836 B2 | 4/2005 | Haas et al. |
| 7,030,052 B2 | 4/2006 | Stochniol et al. |
| 7,049,450 B2 | 5/2006 | Hofen et al. |
| 7,091,384 B2 | 8/2006 | Jaeger et al. |
| 7,157,610 B2 | 1/2007 | Hofen et al. |
| 7,195,748 B2 | 3/2007 | Jaeger et al. |
| 7,507,862 B2 | 3/2009 | Stochniol et al. |
| 7,608,738 B2 | 10/2009 | Herwig et al. |
| 7,879,938 B2 | 2/2011 | Häger et al. |
| 7,923,225 B2 | 4/2011 | Mueller et al. |
| 8,022,201 B2 | 9/2011 | Roos et al. |

(Continued)

FOREIGN PATENT DOCUMENTS

| | | |
|---|---|---|
| EP | 2 322 598 | 5/2011 |
| WO | 2008/016709 | 2/2008 |

(Continued)

OTHER PUBLICATIONS

Oudega et al. GenBank, Accession No. AZ82015 (2005).*
VanBeilen et al. UniProt, Acession No. Q9L4MF (2000).*
U.S. Appl. No. 14/649,414, filed Jun. 3, 2015, Schaffer et al.
U.S. Appl. No. 14/238,591, filed Feb. 12, 2014, Schaffer, et al.
U.S. Appl. No. 14/363,178, filed Jun. 5, 2014, Haas, et al.
U.S. Appl. No. 14/380,483, filed Aug. 22, 2014, Schiemann, et al.
Malca, S. H. et al., "Bacterial CYP153A monooxygenases for the synthesis of omega-hydroxylated fatty acids", Chemical Communications., vol. 48, No. 26, pp. 5115-5117, 2012, XP 002695533.
U.S. Appl. No. 14/435,339, filed Apr. 13, 2015, Engel, et al.

Primary Examiner — Nashaat Nashed
(74) Attorney, Agent, or Firm — Oblon, McClelland, Maier & Neustadt, L.L.P.

(57) ABSTRACT

The invention relates to a method for oxidizing a fatty acid or an ester thereof of formula (I) H3C—(CH2)n-COOR, wherein R is selected from the group that comprises H, methyl, ethyl, propyl, and butyl, wherein n is 0 to 30, preferably 6 to 24, comprising the step of oxidizing the fatty acid or the ester thereof by contacting the fatty acid or the ester thereof with a cytochrome P450 monooxygenase of the CYP153 family in the presence of molecular oxygen and NAD(P)H and a whole-cell catalyst that expresses a recombinant cytochrome P450 monooxygenase of the CYP153 family, a recombinant alcohol dehydrogenase, a recombinant transaminase, and optionally one or more than one recombinant enzyme from the group comprising alanine dehydrogenase, ferredoxin, and ferredoxin reductase, and the use of said whole-cell catalyst to oxidize a fatty acid or an ester thereof.

12 Claims, No Drawings

(56) References Cited

U.S. PATENT DOCUMENTS

| | | | |
|---|---|---|---|
| 8,168,841 B2 | 5/2012 | Herwig et al. | |
| 8,216,813 B2 | 7/2012 | Thum et al. | |
| 8,232,333 B2 | 7/2012 | Haeger et al. | |
| 8,349,596 B2 | 1/2013 | Mueller et al. | |
| 8,372,595 B2 | 2/2013 | Schaffer et al. | |
| 8,378,127 B2 | 2/2013 | Dingerdissen et al. | |
| 8,399,658 B2 | 3/2013 | Hengstermann et al. | |
| 8,404,470 B2 | 3/2013 | Thum et al. | |
| 8,445,720 B2 | 5/2013 | Hannen et al. | |
| 8,486,677 B2 | 7/2013 | Thum et al. | |
| 8,604,227 B2 | 12/2013 | Petrat et al. | |
| 8,703,451 B2 | 4/2014 | Haas et al. | |
| 8,703,993 B2 | 4/2014 | Hannen et al. | |
| 8,796,000 B2 | 8/2014 | Thum et al. | |
| 8,809,576 B2 | 8/2014 | Schraven et al. | |
| 8,835,691 B2 | 9/2014 | Klasovsky et al. | |
| 8,841,096 B2 | 9/2014 | Sieber et al. | |
| 8,871,862 B2 | 10/2014 | Pawlik et al. | |
| 9,000,223 B2 | 4/2015 | Micoine et al. | |
| 9,102,958 B2 * | 8/2015 | Botes | C12P 7/18 |
| 2002/0087036 A1 | 7/2002 | Haas et al. | |
| 2008/0220419 A1 * | 9/2008 | Kubota | C12N 9/0077 435/6.12 |
| 2009/0061471 A1 | 3/2009 | Fasan et al. | |
| 2010/0068773 A1 | 3/2010 | Marx et al. | |
| 2010/0167360 A1 | 7/2010 | Thum et al. | |
| 2010/0190224 A1 | 7/2010 | Poetter et al. | |
| 2010/0261237 A1 | 10/2010 | Verseck et al. | |
| 2010/0266518 A1 | 10/2010 | Springer et al. | |
| 2010/0291644 A1 | 11/2010 | Marx et al. | |
| 2010/0324257 A1 | 12/2010 | Karau et al. | |
| 2011/0039313 A1 | 2/2011 | Verseck et al. | |
| 2011/0118433 A1 | 5/2011 | Pötter et al. | |
| 2011/0118504 A1 | 5/2011 | Haas et al. | |
| 2011/0171702 A1 | 7/2011 | Reinecke et al. | |
| 2011/0251399 A1 | 10/2011 | Dingerdissen et al. | |
| 2012/0034665 A1 | 2/2012 | Haas et al. | |
| 2012/0071577 A1 | 3/2012 | Pfeffer et al. | |
| 2012/0077932 A1 | 3/2012 | Pfeffer et al. | |
| 2012/0264182 A1 | 10/2012 | Reinecke et al. | |
| 2012/0264877 A1 | 10/2012 | Häger et al. | |
| 2012/0315366 A1 | 12/2012 | Zehnacker et al. | |
| 2013/0035403 A1 | 2/2013 | Schaffer et al. | |
| 2013/0052700 A1 * | 2/2013 | Poetter | C07K 14/21 435/128 |
| 2013/0092232 A1 | 4/2013 | Pawlik et al. | |
| 2013/0092233 A1 | 4/2013 | Pawlik et al. | |
| 2013/0130319 A1 | 5/2013 | Schaffer et al. | |
| 2013/0164797 A1 | 6/2013 | Gielen et al. | |
| 2013/0165672 A1 | 6/2013 | Klasovsky et al. | |
| 2013/0165685 A1 | 6/2013 | Hannen et al. | |
| 2013/0171388 A1 | 7/2013 | Pawlik et al. | |
| 2013/0183725 A1 | 7/2013 | Poetter et al. | |
| 2013/0207050 A1 | 8/2013 | Hermasch et al. | |
| 2013/0240799 A1 | 9/2013 | Haeger et al. | |
| 2013/0299750 A1 | 11/2013 | Hermasch et al. | |
| 2013/0331580 A1 | 12/2013 | Klasovsky et al. | |
| 2014/0039210 A1 | 2/2014 | Erhardt et al. | |
| 2014/0039223 A1 | 2/2014 | Klasovsky et al. | |
| 2014/0054224 A1 | 2/2014 | Erhardt et al. | |
| 2014/0120587 A1 | 5/2014 | Haas et al. | |
| 2014/0141478 A1 | 5/2014 | Schaffer et al. | |
| 2014/0178948 A1 | 6/2014 | Schaffer et al. | |
| 2014/0186905 A1 | 7/2014 | Schaffer et al. | |
| 2014/0199736 A1 | 7/2014 | Köehler et al. | |
| 2014/0242646 A1 | 8/2014 | Pötter et al. | |
| 2014/0308717 A1 | 10/2014 | Haas et al. | |

FOREIGN PATENT DOCUMENTS

| | | |
|---|---|---|
| WO | 2009/077461 | 6/2009 |
| WO | 2011/131420 | 10/2011 |

* cited by examiner

ENZYMATIC OMEGA-OXIDATION AND OMEGA-AMINATION OF FATTY ACIDS

The invention relates to a process for the oxidation of a fatty acid or of an ester thereof, comprising the step of oxidising the fatty acid or the ester thereof by contacting with a cytochrome P450 monooxygenase of the CYP153 family in the presence of molecular oxygen and NAD(P)H and a whole-cell catalyst expressing a recombinant cytochrome P450 monooxygenase of the CYP153 family, a recombinant alcohol dehydrogenase, a recombinant transaminase and optionally one or more than one recombinant enzyme from the group comprising alanine dehydrogenase, ferredoxin and ferredoxin reductase, and to the use of this whole-cell catalyst for the oxidation of a fatty acid or of an ester thereof, wherein the fatty acid or the ester thereof preferably has the formula (I)

$$H_3C-(CH_2)_n-COOR \qquad (I),$$

wherein R is selected from the group comprising H, methyl, ethyl, propyl and butyl, wherein n is 0 to 30, preferably 6 to 24.

Polyamides are a class of polymers which are characterized by repeating amide groups. In contrast to the chemically related proteins, the term "polyamide" usually relates to synthetic, commercially available, thermoplastic polymers. Polyamides are derived from primary amines or from secondary amines which are conventionally obtained during the cracking of hydrocarbons. However, it is also possible to use derivatives, more precisely aminocarboxylic acid, lactams and diamines, for producing the polymer. Also of interest as starting materials are short-chain, gaseous alkanes which can be obtained proceeding from renewable raw materials using biotechnological processes.

Many commercial polyamides in high demand are produced starting from lactams. For example, "Polyamide 6" can be obtained by polymerization of ε-caprolactam and "Polyamide 12" can be obtained by polymerization of laurolactam. Further commercially interesting products include copolymers of lactam, e.g. copolymers of ε-caprolactam and laurolactam.

The conventional chemical-technical production of amines is dependent on the supply of fossil raw materials, inefficient, and in the process large amounts of undesired by-products are produced, in some steps of the synthesis up to 80%. One example of such a process is the production of laurolactam, which is conventionally obtained by trimerization of butadiene. The trimerization product cyclododecatriene is hydrogenated and the cyclododecane resulting therefrom is oxidized to cyclododecanone, which is then reacted with hydroxylamine to give cyclododecane oxime, which is finally converted to laurolactam via a Beckmann rearrangement.

In view of the said disadvantages, processes have been developed in order to obtain amines using biocatalysts starting from renewable raw materials. Suitable renewable raw materials are in particular sources of fatty acids which can be obtained in the form of rapeseed oil, globe thistle oil, palm kernel oil, coconut oil, sunflower kernel oil and similar natural products from a large number of biological sources, in particular from plants.

PCT/EP 2008/067447 describes a biological system for producing chemically related products, more precisely ω-aminocarboxylic acids, using a cell which has a series of suitable enzymatic activities and is able to convert carboxylic acids to corresponding ω-aminocarboxylic acid.

A known disadvantage of the AlkBGT oxidase system from *Pseudomonas putida* GPO1 used therein, however, is that it is not able to achieve selective oxidation of aliphatic alkanes to primary alcohols. Rather, a multitude of oxidation products arise; in particular, the fraction of more highly oxidized products, such as the corresponding aldehyde, ketone or the corresponding carboxylic acid, increases with increasing reaction time (C. Grant, J. M. Woodley and F. Baganz (2011), *Enzyme and Microbial Technology* 48, 480-486), which correspondingly reduces the yield of desired amine.

The problem of the relatively unselective oxidation is exacerbated by the fact that the corresponding oxidation products are structurally very similar. This means that it is very difficult to separate them off from the desired oxidation products efficiently and without a significant loss in yield.

There is therefore a need for processes in which the enzymatically catalysed reactions proceed more selectively and the formation of irreversibly produced by-products is minimized.

Against this background, the problem addressed by the invention consists in providing an improved process for the oxidation and amination of fatty acids using biocatalysts.

A further object addressed by the invention consists in improving the process such that the yield, based on the amount of fatty acid substrate or other substrates, increases the amount of the carbon substrate for cells used for biotechnological synthesis and/or the concentration of by-products or the ratio of by-products to desired product is reduced.

A further problem addressed by the invention consists in improving the process such that the selectivity of the biocatalysts used, in particular of fatty acid oxidases, is increased and/or extended, either at the start of the reaction, i.e. before reaching a plateau during the product concentration overtime, or after adjusting the equilibrium, i.e. after reaching the plateau.

A further object addressed by the invention consists in improving the ability to be worked up of the reaction mixture formed during the biotechnological oxidation and/or amination of fatty acids, in particular with regard to the efficiency and rate of the phase separation of hydrophilic and hydrophobic substances.

These and other objects are achieved by the subject matter of the present application and particularly also by the subject matter of the accompanying independent claims, with embodiments arising from the dependent claims.

The object underlying the invention is achieved in a first aspect by a process for the oxidation of a fatty acid or of an ester thereof comprising the step of:
a) oxidising the fatty acid or the ester thereof by contacting with a cytochrome P450 monooxygenase of the CYP153 family in the presence of molecular oxygen and NAD(P)H,
wherein the fatty acid or the ester thereof preferably has the formula (I)

$$H_3C-(CH_2)_n-COOR \qquad (I),$$

wherein R is selected from the group comprising H, methyl, ethyl, propyl and butyl,
wherein n is 0 to 30, preferably 6 to 24.

In a first embodiment of the first aspect, the object is achieved by a process further comprising the steps of:
b) further oxidising of the oxidized fatty acid or of the ester thereof from step a) by contacting with an alcohol dehydrogenase, c) amination of the further oxidized fatty acid or of the ester thereof from step b) by contacting with a transaminase in the presence of an amine donor, preferably alanine, wherein step c) optionally takes place in the presence of an alanine dehydrogenase, ammonium and NAD(P)H.

In a second embodiment, which is also an embodiment of the first embodiment, the object is achieved by a process wherein the cytochrome P450 monooxygenase of the CYP153 family has the peptide sequence LL(I/L)(V/I)GGNDTTRN (SEQ ID NO. 21) and is preferably the cytochrome P450 monooxygenase of the CYP153 family from *Alcanivorax borkumensis* SK2 (database code YP_691921) (SEQ ID NO. 19) or a variant thereof.

This and all other database codes used in this document originate from the Genbank Protein database of the NCBI in the release available online on 9 Mar. 2012.

In a third embodiment, which is also an embodiment of the first to second embodiment, the object is achieved by a process wherein the alcohol dehydrogenase is a NAD(P)$^+$-dependent alcohol dehydrogenase, preferably the NAD-dependent alcohol dehydrogenase from *Escherichia coli* MS 187-1 (database code ZP_07145023) (SEQ ID NO. 17) or a variant thereof or the alcohol dehydrogenase from *Bacillus stearothermophilus* (database code P42328) or a variant thereof, or an oxidoreductase of the glucose-methanol-choline-oxidoreductase family, preferably that from *Pseudomonas putida* (database code CAB54054.1) or a variant thereof, or a flavin-containing alcohol dehydrogenase, preferably the flavin-containing alcohol dehydrogenase from *Candida tropicalis* (database code AAS46878.1) (SEQ ID NO. 40) or a variant thereof.

In a fourth embodiment, which is also an embodiment of the first to third embodiment, the object is achieved by a process wherein, in step a), additionally a ferredoxin reductase, preferably the ferredoxin reductase from *Alcanivorax borkumensis* SK2 (database code YP_691923) (SEQ ID NO. 13) or a variant thereof, and/or a ferredoxin, preferably the ferredoxin from *Alcanivorax borkumensis* SK2 (database code YP_691920) (SEQ ID NO. 15) or a variant thereof, is present.

In a fifth embodiment, which is also an embodiment of the first to fourth embodiment, the object is achieved by a process, wherein step c) takes place in the presence of an alanine dehydrogenase, ammonium and NADH and the alanine dehydrogenase is the alanine dehydrogenase from *Bacillus subtilis* subsp. *subtilis* str. 168 (database code NP_391071) (SEQ ID NO. 22) or a variant thereof.

In a sixth embodiment, which is also an embodiment of the first to fifth embodiment, the object is achieved by a process, wherein at least one enzyme from the group comprising cytochrome P450 monooxygenase of the CYP153 family, alcohol dehydrogenase, transaminase, alanine dehydrogenase, ferredoxin and ferredoxin reductase is provided recombinantly in the form of a whole-cell catalyst.

In a seventh embodiment, which is also an embodiment of the sixth embodiment, the object is achieved by a process, wherein all of the enzymes from the group comprising cytochrome P450 monooxygenase of the CYP153 family, alcohol dehydrogenase, transaminase, alanine dehydrogenase, ferredoxin and ferredoxin reductase present or contacted in at least one of the steps a), b) or c) with the fatty acid or the ester thereof, the further oxidized fatty acid or the ester thereof from step b) or the aminated further oxidized fatty acid or the ester thereof from step c) are provided recombinantly in the form of one or more than one whole-cell catalyst.

In an eighth embodiment, which is also an embodiment of the sixth to seventh embodiment, the object is achieved by a process wherein the whole-cell catalyst additionally expresses a polypeptide of the AlkL family, preferably an AlkL from the group comprising AlkL from *Pseudomonas putida* (database code CAB69081) (SEQ ID NO. 3), *Marinobacter aquaeolei* VT8 (database code YP_957722) (SEQ ID NO. 5), *Oceanicaulis alexandrii* HTCC2633 (database code ZP_00953584) (SEQ ID NO. 7), *Marinobacter manganoxydans* MnI7-9 (database code ZP_09158756) (SEQ ID NO. 9), *Caulobacter* sp. K31 (database code YP_001672217) (SEQ ID NO. 11), *Pseudomonas oleovorans* (database code Q00595) (SEQ ID NO. 1) or a variant thereof.

In a ninth embodiment, which is also an embodiment of the first to eighth embodiment, the object is achieved by a process wherein the whole-cell catalyst is a cell which has an activity, reduced compared to its wildtype, of at least one enzyme which catalyses one of the reactions of the β-oxidation of fatty acids, wherein the enzyme is preferably selected from the group which comprises fatty acid importer, fatty acid-CoA ligase, acyl-CoA dehydrogenase, 2,4-dienoyl-CoA reductase, enoyl-CoA hydratase and 3-ketoacyl-CoA thiolase.

In a tenth embodiment, which is also an embodiment of the first to ninth embodiment, the object is achieved by a process wherein the alanine dehydrogenase in step c) is selected such that it reduces the redox cofactor oxidized by the alcohol dehydrogenase in step b), preferably NAD$^+$ or NADP$^+$.

In a second aspect, the object is achieved by a whole-cell catalyst expressing a recombinant cytochrome P450 monooxygenase of the CYP153 family, a recombinant alcohol dehydrogenase, a recombinant transaminase and optionally one or more than one recombinant enzyme from the group comprising alanine dehydrogenase, ferredoxin and ferredoxin reductase.

In a first embodiment of the first aspect, the object is achieved by a whole-cell catalyst, wherein the whole-cell catalyst additionally expresses a polypeptide of the AlkL family, preferably an AlkL from the group comprising AlkL from *Pseudomonas putida* (database code CAB69081) (SEQ ID NO. 3), *Marinobacter aquaeolei* VT8 (database code YP_957722) (SEQ ID NO. 5), *Oceanicaulis alexandrii* HTCC2633 (database code ZP_00953584) (SEQ ID NO. 7), *Marinobacter manganoxydans* MnI7-9 (database code ZP_09158756) (SEQ ID NO. 9), *Caulobacter* sp. K31 (database code YP_001672217) (SEQ ID NO. 11), *Pseudomonas oleovorans* (database code Q00595) (SEQ ID NO. 1) or a variant thereof.

In a second embodiment, which is also an embodiment of the first embodiment, the object is achieved by a whole-cell catalyst wherein the whole-cell catalyst is a cell which has an activity, reduced compared to its wildtype, of at least one enzyme which catalyses one of the reactions of the β-oxidation of fatty acids, wherein the enzyme is preferably selected from the group which comprises fatty acid importer, fatty acid-CoA ligase, acyl-CoA dehydrogenase, 2,4-dienoyl-CoA reductase, enoyl-CoA hydratase and β-ketoacyl-CoA thiolase.

In a third embodiment, which is also an embodiment of the first to second embodiment, the object is achieved by a whole-cell catalyst, wherein the whole-cell catalyst expresses a ferredoxin reductase and a ferredoxin.

In a fourth embodiment, which is also an embodiment of the first to third embodiment, the object is achieved by a whole-cell catalyst, wherein the whole-cell catalyst expresses an alanine dehydrogenase, and wherein the alanine dehydrogenase is from *Bacillus subtilis* subsp. *subtilis* str. 168 (database code NP_391071) (SEQ ID NO. 22) or a variant thereof.

In a fifth embodiment, which is also an embodiment of the first to fourth embodiment, the object is achieved by a whole-cell catalyst, wherein the cytochrome P450 monooxygenase of the CYP153 family has the peptide sequence LL(I/L)(V/I)GGNDTTRN (SEQ ID NO. 21) and/or it is the cytochrome P450 monooxygenase of the CYP153 family from *Alcanivorax borkumensis SK2* (database code YP_691921) (SEQ ID NO. 19) or a variant thereof, and the ferredoxin reductase is the ferredoxin reductase from *Alcanivorax borkumensis* SK2 (database code YP_691923) (SEQ ID NO. 13) or a variant thereof and the ferredoxin is the ferredoxin from *Alcanivorax borkumensis* SK2 (database code YP_691920) (SEQ ID NO. 15) or a variant thereof.

In a sixth embodiment, which is also an embodiment of the first to fifth embodiment, the object is achieved by a whole-cell catalyst, wherein the alcohol dehydrogenase is a NAD(P)$^+$-dependent alcohol dehydrogenase, an oxidoreductase of the glucose-methanol-choline-oxidoreductase family or a flavin-containing alcohol oxidase, preferably a NAD(P)$^+$-dependent alcohol dehydrogenase, most preferably the NAD-dependent alcohol dehydrogenase from *Escherichia coli* MS 187-1 (database code ZP_07145023) (SEQ ID NO. 17) or a variant thereof.

In a seventh embodiment, which is also a further embodiment of the first or second aspect and embodiments thereof, the object is achieved by a whole-cell catalyst according to the second aspect or an embodiment of the second aspect or processes according to the first aspect or of an embodiment of the first aspect, wherein the transaminase is the transaminase from *Pseudomonas putida* GB-1 (database code YP_001668026.1) or a variant thereof.

In an eighth embodiment, which is also a further embodiment of the first or second aspect, the fatty acid or the ester thereof is an unsaturated or branched fatty acid or ester thereof.

In a ninth embodiment, which is also a further embodiment of the first or second aspect, the object is achieved by a process wherein at least one enzyme from the group comprising cytochrome P450 monooxygenase of the CYP153 family, alcohol dehydrogenase, transaminase, alanine dehydrogenase, ferredoxin and ferredoxin reductase is provided recombinantly in the form of a whole-cell catalyst, or the object is achieved by a whole-cell catalyst, wherein the whole-cell catalyst is a cell which has an an activity, reduced relative to the wildtype of the cell, of at least one endogenous aldehyde dehydrogenase.

In a third aspect, the object underlying the invention is achieved by the use of the whole-cell catalyst according to the second aspect of the invention or one of its embodiments for the oxidation and/or amination of a fatty acid or ester thereof, wherein the fatty acid or the ester thereof preferably has the formula (I)

$$H_3C-(CH_2)_n-COOR \qquad (I),$$

wherein R is selected from the group comprising H, methyl, ethyl, propyl and butyl,
wherein n is 0 to 30, preferably 6 to 24.

In a first embodiment of the third aspect, the problem is solved through a use, wherein the oxidation produces a mixture of oxidation products which, based on the quantitative amount of the reacted fatty acid or of the ester thereof, comprises at least 90% of the corresponding alcohol, less than 1% of the corresponding aldehyde and less than 10% of the corresponding acid.

In a second embodiment of the third aspect, which is also a further embodiment of the embodiments of the third aspect, the fatty acid is an unsaturated or branched fatty acid or ester thereof.

The present invention is based on the discovery by the inventors that the use of specific monooxygenases or of whole-cell catalysts expressing such monooxygenases, more precisely cytochrome P450 monooxygenase of the CYP153 family, surprisingly leads to the oxidation and/or amination of fatty acids for the formation of the desired products with higher selectivity and better relative yield.

Without wishing to be bound to any theory, the inventors assume that the nature of the active catalytic centre of these monooxygenases is such that already hydroxylated products are bonded and further oxidized not only to the aldehyde or even products oxidized to the acid with lower affinity than is the case for comparable monooxygenases known from the prior art.

The process according to the invention envisages, in step a), the oxidation of fatty acids by a cytochrome P450 monooxygenase of the CYP153 family. In one embodiment, the term "fatty acid or ester thereof" is a compound of the formula $H_3C-(CH_2)_x-COOR$, where x is 4, 5, 6, 7, 8, 9, 10, 11, 12, 13, 14, 15, 16, 17, 18, 19, 20, 21, 22, 23, 24, 25, 26, 27, 28, 29 or 30 and R is hydrogen, methyl, ethyl or propyl, preferably hydrogen. In a particularly preferred embodiment, x is 6, 7, 8, 9, 10, 11, 12, 13, 14, 15, 16, 17, 18, 19, 20, 21, 22,23 or 24 and R is hydrogen. In a most preferred embodiment, it is lauric acid or methyl laurate. In a preferred embodiment, it is an unsaturated fatty acid from the group comprising myristoleic acid, palmitoleic acid, petroselinic acid, oleic acid, elaidic acid, vaccenic acid, gadoleic acid, eicosenoic acid or erucic acid. Likewise possible are mixtures of different fatty acids, for example mixtures of fatty acids or fatty acid esters obtained by hydrolysis and optional esterification of globe thistle oil, coconut oil, *cuphea* oil or palm kernel oil. Since not all fatty acids are soluble to a noteworthy extent at room temperature, it may be necessary to resort to other measures, such as, for example, increasing the temperature or, preferably, adding an organic solvent, in order to make them accessible to the aqueous phase. In a particularly preferred embodiment, a fatty acid or an ester thereof, most preferably methyl laurate or oleic acid, is used as such a further solvent.

As in the case of all of the compounds specified in this application, fatty acids include not only the protonated form of the fatty acid, but also all forms, formulations or salts dissociated in aqueous solution. For example, the term lauric acid also includes laurate or sodium laurate. As a further example, the amino acid alanine includes the forms deprotonated or protonated on the carboxyl group in water and the forms deprotonated or protonated on the amino group.

The process according to the invention provides not only the oxidation for the hydroxylated fatty acid, but permits the efficient reaction of fatty acids to the corresponding w-aminocarboxylic acid by means of an enzyme system comprising a cytochrome P450 monooxygenase of the CYP153 family, an alcohol dehydrogenase, a transaminase and optionally an amino acid dehydrogenase. The use of such enzymes takes place under conditions which are compatible with their enzymatic activity. These include firstly the selection of a suitable aqueous buffer system comprising at least one pH-stabilizing buffer, for example sodium phosphate, optionally additionally at least one salt, for example sodium chloride, at a suitable pH. In a most preferred embodiment, the pH is 5, 5.5, 6, 6.5, 7, 7.5, 8, 8.5, 9 or 10, preferably 2.5 to 7.5, particularly preferably 5.5 to 7.5. The temperature must also be matched to the activity of the enzyme or enzymes to be used. In a preferred embodiment, the temperature is 1 to 45, more preferably 20 to 45, most preferably 28 to 42° C. The selection of a suitable buffer system and the stabilization of the activity can be performed by a person skilled in the art using standard processes, see for example A Cornish-Bowden (1995), Fundamentals of Enzyme Kinetics, Portland Press Limited, 1995. The activity of the cytochrome P450 monooxygenase of the CYP153 family, without or in combination with ferredoxin and ferredoxin reductase, can be determined by means of the assay described by Scheps, D., Malca, H., Hoffmann, B., Nestl, B. M, and Hauer, B. (2011) Org. Biomol. Chem., 9, 6727. Whether ferredoxin and/or ferredoxin reductase are active is evident to the person skilled in the art from a considerable increase in activity of the monooxygenase in the presence of the two active enzymes compared with their absence. An enzyme test for the activity of transaminases is sold by Cayman Chemical Company, Ann Arbor, Mich., ("Alanine Transaminase Activity Assay Kit, Item No. 700260"). The activity of an amino acid dehydrogenase can be determined according to Germano, H. J., and Anderson, K. E. (1968), J. Bact. 96 (1), pages 55-60.

The use of enzymes further requires the presence of all necessary substrates. Thus, besides the fatty acid to be reacted according to the invention or the ester thereof, the presence of oxygen and of an electron donor is necessary for the activity of the cytochrome P450 monooxygenase of the CYP153 family. Preferably, oxygen is made available by contacting the reaction mixture comprising enzyme(s) or cells and substrates with atmospheric air, alternatively with pure oxygen or with oxygen-enriched atmospheric air, particularly preferably by stirring the reaction mixture while it is in contact with atmospheric air, alternatively with pure oxygen or with oxygen-enriched atmospheric air.

For the optimal supply of the cytochrome P450 monooxygenase of the CYP153 family with electrons from the reducing agent, preferably NADH, it is preferred that the monooxygenase is used together with ferredoxin reductase that interacts functionally with it and ferredoxin that interacts functionally with it. These may be isolated polypeptides or, in the case of using a whole-cell catalyst, coexpressed polypeptides or polypeptides fused on the N- or C-terminus with the cytochrome P450 monooxygenase of the CYP153 family. Whether a ferredoxin reductase or a ferredoxin with a given cytochrome P450 monooxygenase of the CYP153 family interact functionally with one another can be readily established by a person skilled in the art by whether the reducing agent is oxidized in the presence of an alkane substrate and the three polypeptides. Alternatively, it is possible to use the enzyme test described by Scheps, D., Malca, H., Hoffmann, B., Nestl, B. M, and Hauer, B. (2011) Org. Biomol. Chem., 9, 6727 which, in the case of functionally interacting polypeptides, exhibits a considerable increase in the reaction rate. In a particularly preferred embodiment, the cytochrome P450 monooxygenase of the CYP153 family, the ferredoxin and the ferredoxin reductase originate from the same organism. In a particularly preferred embodiment, it is the ferredoxin reductase from *Alcanivorax borkumensis* SK2 (database code YP_691923) (SEQ ID NO. 13) or a variant thereof, the ferredoxin from *Alcanivorax borkumensis* SK2 (database code YP_691920) (SEQ ID NO. 15) or a variant thereof and the cytochrome P450 monooxygenase of the CYP153 family from *Alcanivorax borkumensis* SK2 (database code YP_691921) (SEQ ID NO. 19) or a variant thereof.

For all of the enzymes used according to the invention, they may be cells comprising corresponding enzymatically active polypeptides or lysates thereof or preparations of the polypeptides in all purification states, from the crude lysate ranging to the pure polypeptide, or whole-cell catalysts. Numerous methods are known to those experts in the field, by which enzymatically active polypeptides may be overexpressed in suitable cells and may be purified or isolated. To express the polypeptides, all expression systems available to the person skilled in the art can be used. For the purification, chromatographic processes are suitable, for example the affinity-chromatographic purification of a recombinant protein provided with a tag using an immobilized ligand, for example a nickel ion in the case of a histidine tag, of immobilized glutathione in the case of a glutathione S-transferase fusioned to the target protein or of immobilized maltose in the case of a tag comprising maltose-binding protein. For numerous biotechnologically important types of cells, e.g. *E. coli*, suitable processes and vectors are known which can be used for the expression or overexpression of a nucleic acid molecule, for example the vectors of the pET or pGEX type and cells suitable for their expression (B A Moffatt, and F W Studier (1986) *J. Mol. Biol.* 189, 113-130, A H Rosenberg, B N Lade, D Chui, S Lin, J J Dunn, and F W Studier (1987) *Gene* 56, 125-135 and F W Studier, A H Rosenberg, J J Dunn, and J W Dubendorff (1990) *Meth. Enzymol.* 185, 60-89.

The purified enzymes can be used either in soluble form or immobilized. Suitable processes are known to the person skilled in the art with which polypeptides can be covalently or noncovalently immobilized on organic or inorganic solid phases, for example by sulphhydryl coupling chemistry (e.g. kits from Pierce). Cell-membrane-associated or cell-membrane-embedded enzymes can be used in the form of membrane preparations or solubilized.

In the case of the use of at least one whole-cell catalyst, in the case of a prolonged reaction time it must be ensured that the conditions are compatible with the viability of the at least one cell used as whole-cell catalyst. The person skilled in the art can refer to standard works, for example Fuchs/Schlegel (2007) Allgemeine Mikrobiologie, 2008, Georg Thieme Verlag, for conditions and solutions which permit the retention of such cells in a viable state.

In a preferred embodiment, the term "whole-cell catalyst", as used herein, is understood as meaning an intact, viable and metabolically active cell which provides a desired enzymatic activity. The whole-cell catalyst can transport the substrate to be metabolized, in the case of the present invention the alcohol or the oxidation product resulting therefrom, either into the inside of the cell, where it is metabolized by cytosolic enzymes, or it can present the enzyme of interest on its surface, where it is exposed directly to substrates in the medium. The person skilled in the art is aware of numerous systems for producing whole-cell catalysts, for example from DE 60216245.

When using a whole-cell catalyst, the problem can arise that a substrate has to be brought into contact with an intracellularly localized enzyme so that it results in the desired reaction. In the case of long-chain alkanes and derivatives thereof, it is preferred that the whole-cell catalyst has a polypeptide of the AlkL family. In a preferred embodiment, a "polypeptide of the AlkL family", as used herein, is a polypeptide which, over a length of 230 successive amino acids, has an at least 80, preferably 90, more preferred 90% sequence identity to AlkL from *Pseudomonas putida* (database code CAB69081) (SEQ ID NO. 3) and preferably the ability to assist the import of long-chain alkanes into the inside of a cell. In a further embodiment, a "polypeptide of the AlkL family", as used herein, is a polypeptide located in the outer membrane of a Gram-negative bacterium which has the sequence motif DXWAPAXQ(V/A)GXR (SEQ ID NO. 67), where X is a proteinogenic amino acid, and preferably is additionally AlkL from *Pseudomonas putida* (database code CAB69081) (SEQ ID NO. 3) or a variant thereof. Examples of members of the AlkL family include AlkL from *Pseudomonas putida* (database code CAB69081) (SEQ ID NO. 3), *Marinobacter aquaeolei* VT8 (database code YP_957722) (SEQ ID NO. 5), *Oceanicaulis alexandrii* HTCC2633 (database code ZP_00953584) (SEQ ID NO. 7), *Marinobacter manganoxydans* MnI7-9 (database code ZP_09158756) (SEQ ID NO. 9), *Caulobacter* sp. K31 (database code YP_001672217) (SEQ ID NO. 11), *Pseudomonas oleovorans* (database code Q00595) (SEQ ID NO. 1) and variants thereof.

The use of isolated enzymes is recommended for a series of applications. In a preferred embodiment, the term "isolated", as used herein, means that the enzyme is in a more pure and/or concentrated form than in its natural source. In a preferred embodiment, the enzyme is classed as being isolated if it is a polypeptide enzyme and constitutes more than 60, 70, 80, 90 or preferably 95% of the mass protein fraction of the corresponding preparation. The person skilled in the art is aware of numerous processes for measuring the mass of a protein in a solution, for example the visual estimation with reference to the thickness of corresponding protein bands on SDS-polyacrylamide gels, NMR spectroscopy or mass spectrometry-based processes.

The enzymes used according to the invention are preferably recombinant enzymes. In a preferred embodiment, the term "recombinant", as used herein, is understood as meaning that the corresponding nucleic acid molecule does not occur in nature and/or it has been produced using genetic engineering methods. In a preferred embodiment, the term recombinant protein is used if the corresponding polypeptide is encoded by a recombinant nucleic acid. In a preferred embodiment, a recombinant cell, as used herein, is understood as meaning a cell which has at least one recombinant nucleic acid or a recombinant polypeptide. Processes suitable for producing recombinant molecules or cells are known to the person skilled in the art, for example those described in Sambrook/Fritsch/Maniatis (1989): Molecular Cloning: A Laboratory Manual, Cold Spring Harbor Laboratory Press, 2nd edition.

In a preferred embodiment, the cell used as whole-cell catalyst or as expression system is a prokaryotic, preferably a bacterial, cell. It is preferred according to the invention that, on account of the good genetic accessibility, microorganisms are used; selected from the group of bacteria, particularly from the group comprising, preferably consisting of *Magnetococcus, Mariprofundus, Acetobacter, Acidiphilium, Afipia, Ahrensia, Asticcacaulis, Aurantimonas, Azorhizobium, Azospirillum, Bacillus, Bartonella, tribocorum, Beijerinckia, Bradyrhizobium, Brevundimonas, subvibrioides, Brucella, Caulobacter, Chelativorans, Citreicefia, Citromicrobium, Corynebacterium, Dinoroseobacter, Elythrobacter, Fulvimarina, Gluconacetobacter, Granulibacter, Hirschia, Hoeflea, Hyphomicrobium, Hyphomonas, Ketogulonicigenium, Labrenzia, Loktanella, Magnetospirillum, Maricaulis, Maritimibacter, Mesorhizobium, Methylobacterium, Methylocystis, Methylosinus, Nitrobacter, Novosphingobium, Oceanibulbus, Oceanicaulis, Oceanicola, Ochrobactrum, Octadecabacter, Oligotropha, Paracoccus, Parvibaculum, Parvularcula, Pelagibaca, Phaeobacter, Phenylobacterium, Polymorphum, Pseudovibrio, Rhodobacter, Rhodomicrobium, Rhodopseudomonas, Rhodospirillum, Roseibium, Roseobacter, Roseomonas, Roseovarius, Ruegeria, Sagittula, Silicibacter, Sphingobium, Sphingomonas, Sphingopyxis, Starkeya, Suffitobacter, Thalassiobium, Xanthobacter, Zymomonas, Agrobacterium, Rhizobium, Sinorhizobium, Anaplasma, Ehrlichia, Neorickettsia, Orientia, Rickettsia, Wolbachia, Bordetella, Burkholderia, Cupriavidus, taiwanensis, Lautropia, Limnobacter, Polynucleobacter, Ralstonia, Chromobacterium, Eikenella, corrodens, Basfia, Kingefia, Laribacter, Lutiella, Neisseria, Simonsiella, Achromobacter, Acidovorax, Alicycliphilus, Aromatoleum, Azoarcus, Comamonas, Dechloromonas, Delftia, Gallionella, Herbaspirillum, Herminiimonas, Hylemonella, Janthinobacterium, Leptothrix, Methylibium, Methylobacifius, Methylophilales, Methyloversatilis, Methylovorus, Nitrosomonas, Nitrosospira, Oxalobacter, Parasutterella, Polaromonas, Polaromonas, Pusillimonas, Rhodoferax, Rubrivivax, Sideroxydans, Sutterella, wadsworthensis, Taylorella, Thauera, Thiobacillus, Thiomonas, Variovorax, Verminephrobacter, Anaeromyxobacter, Bdellovibrio, bacteriovorus, Bilophila, Desulfarculus, Desulfatibacillum, Desulfobacca, Desulfobacterium, Desulfobulbus, Desulfococcus, Desulfohalobium, Desuffitobacterium, Desulfomicrobium, Desulfonatronospira, Desulfotalea, Desulfovibrio, Desulfuromonas, Geobacter, Haliangium, Hippea, Lawsonia, Myxococcus, Pelobacter, Plesiocystis, Sorangium, Stigmatella, Syntrophobacter, Syntrophus, Arcobacter, Caminibacter, Campylobacter, Helicobacter, Nitratifractor, Nitratiruptor, Sulfuricurvum, Sulfurimonas, Sulfurospirillum, Sulfurovum, Wolinella, Buchnera, Blochmannia, Hamiltonella, Regiella, Riesia, Citrobacter, Cronobacter, Dickeya, Edwardsiella, Enterobacter, Erwinia, Escherichia, Klebsiella, Pantoea, Pectobacterium, Proteus, Providencia, Rahnella, Salmonella, Serratia, Shigella, Sodalis, Wigglesworthia, Glossina, Xenorhabdus, Yersinia, Acidithiobacillus, Acinetobacter, Aeromonas, Alcanivorax, Alkalilimnicola, Allochromatium, Alteromonadales, Alteromonas, Baumannia, Beggiatoa, Bermanella, Carsonella, Ruthia, Vesicomyosocius, Cardiobacterium, Chromohalobacter, Colwellia, Congregibacter, Coxiella, Dichelobacter, Endoriftia, Enhydrobacter, Ferrimonas, Francisella, Glaciecola, Hahella, Halomonas, Halorhodospira, Halothiobacillus, ldiomarina, Kangiella, Legionella, Marinobacter, Marinomonas, Methylobacter, Methylococcus, Methylomicrobium, Methylophaga, Moraxella, Moritella, Neptuniibacter, Nitrococcus, Pseudoalteromonas, Psychrobacter, Psychromonas, Reinekea, Rickettsiefla, Saccharophagus, Shewanefla, Succinatimonas, Teredinibacter, Thioalkalimicrobium, Thioalkalivibrio, Thiomicrospira, Tolumonas, Vibrionales, Actinobacillus, Aggregatibacter, Gallibacterium, Haemophilus, Histophilus, Mannheimia, Pasteurella, Azotobacter, Cellvibrio, Pseudomonas, Aliivibrio, Grimontia, Photobacterium, Photobacterium, Vibrio, Pseudoxanthomonas, Stenotrophomonas, Xanthomonas, Xylella, Borrelia, Brachyspira, Leptospira, Spirochaeta, Treponema, Hodgkinia, Puniceispirillum, Liberibacter, Pelagibacter, Odyssella, Accumulibacter, in particular B. subtilis, B. megaterium, C. glutamicum, E. coli, Pseudomonas* sp., *Pseudomonas fluorescens, Pseudomonas putida, Pseudomonas stutzeri, Acinetobacter* sp., *Burkholderia* sp., *Burkholderia thailandensis, Cyanobakterien, Klebsiella* sp., *Klebsiella oxytoca, Salmonella* sp., *Rhizobium* sp. and *Rhizobium meliloti*, with *E. coli* being particularly preferred.

In a preferred embodiment, the term "cytochrome P450 monooxygenase of the CYP153 family" is understood as meaning a cytosolic oxidase which is part of a 3-component system which further comprises a ferredoxin and a ferredoxin reductase, with an alkane binding site and the ability to hydroxylate alkanes. In a particularly preferred embodiment, it is an enzyme which has to at least 80, preferably 90, most preferably 95 or 99%, sequence identity to the cytochrome P450 monooxygenase of the CYP153 family from *Alcanivorax borkumensis* SK2 (database code YP_691921) (SEQ ID NO. 19) or an enzyme which comprises a polypeptide sequence which has at least 80, preferably 90, most preferably 95 or 99%, sequence identity to the cytochrome P450 monooxygenase of the CYP153 family from *Alcanivorax borkumensis* SK2 (database code YP_691921) (SEQ ID NO. 19) and moreover has alkane hydroxylase activity.

In a preferred embodiment, the term "alkane hydroxylase activity", as used herein, is to be understood as meaning the ability to catalyse the hydroxylation of alkanes or unsubstituted linear alkyl radicals comprising at least five, preferably twelve, carbon atoms. In a further preferred embodiment, the term "cytochrome P450 monooxygenase of the CYP153 family" is understood as meaning a non-membrane-bonded oxidase which includes a binding site for alkanes, unsubstituted linear alkyl radicals comprising at least five, preferably twelve, carbon atoms or monohydroxylated alkanes and the polypeptide chain of which the motif LL(I/L)(V/I)GGNDT-TRN (SEQ ID NO. 21). In a preferred embodiment, a "cytochrome P450 monooxygenase of the CYP153 family", as used herein, is a cytochrome P450 monooxygenase of the CYP153 family from *Alcanivorax borkumensis* SK2 (database code YP_691921) (SEQ ID NO. 19) or a variant which preferably has alkane hydroxylase activity.

The use of cytochrome P450 monooxygenases of the CYP153 family for the hydroxylation of alkanes is described in the prior art, as are enzyme tests for determining the enzyme activity and processes for the expression and purification (Scheps, D., Malca, H., Hoffmann, B., Nestl, B. M, and Hauer, B. (2011) Org. Biomol. Chem., 9, 6727). Besides an alkane to be oxidized or unsubstituted linear alkyl radical comprising at least five, preferably twelve, carbon atoms, the substrates involved in the reaction of the enzyme comprise oxygen and electrons which are transferred in the form of NADH preferably via the other two components, ferredoxin and a ferredoxin reductase, to the oxidase. Scheps et al. (2011) and Roome, P. W., Jr., Philley, J. C., and Peterson (1983) J. Biol. Chem. 258, 2593, Roome, P. W., and Peterson, J. A. (1988), Arch. Biochem. Biophys., 266, 41 and Peterson, J. A., Lorence, M. C., and Amarneh, B. (1990) J. Biol. Chem, 265, 6066 also disclose processes for obtaining ferredoxin and ferredoxin reductase in functional form.

According to the invention, in step b), an alcohol dehydrogenase is used for the oxidation of the fatty acid alcohol resulting in step a). Alcohol dehydrogenases have for decades been a greatly observed and biotechnologically highly relevant enzyme class in biochemistry in connection with brewing fermentation processes, said class including various groups of isoforms. Thus, membrane-bonded, flavin-dependent alcohol dehydrogenases of *Pseudomonas putida* GPO1 AlkJ type exist which use flavocofactors instead of $NAD^+$. A further group includes iron-containing alcohol dehydrogenases that are sensitive towards oxygen and which are found in bacteria and in inactive form in yeast. Another group includes NAD-dependent alcohol dehydrogenases, among them zinc-containing alcohol dehydrogenases in which the active centre has a cysteine-coordinated zinc atom which fixes the alcohol substrate. In a preferred embodiment, the term "alcohol dehydrogenase", as used herein, is understood as meaning an enzyme which oxidizes an aldehyde or ketone to the corresponding primary or secondary alcohol, respectively. Preferably, the alcohol dehydrogenase in the process according to the invention is a NAD-dependent alcohol dehydrogenase, i.e. an alcohol dehydrogenase which uses $NAD^+$ as cofactor for the oxidation of the alcohol or NADH for reducing the corresponding aldehyde or ketone. In the most preferred embodiment, the alcohol dehydrogenase is a $NAD^+$-dependent zinc-containing alcohol dehydrogenase.

In a further preferred embodiment, the alcohol dehydrogenase is an alcohol dehydrogenase oxidoreductase of the glucose-methanol-choline-oxidoreductase family. In a preferred embodiment, the term "oxidoreductase of the glucose-methanol-choline-oxidoreductase family", as used herein, is understood as meaning an alcohol dehydrogenase which comprises FAD as cofactor and is preferably the enzyme from *Pseudomonas putida* (database code CAB54054) (SEQ ID NO. 46) or a variant thereof. Examples include SEQ ID No. 26, 27, 28 and 29, and also the enzyme from *Pseudomonas putida* (database code CAB54054) (SEQ ID NO. 46).

In a further preferred embodiment, the alcohol dehydrogenase is an alcohol dehydrogenase of the family of the flavin-containing alcohol dehydrogenases. In preferred embodiment, the term "family of flavin-containing alcohol dehydrogenases", as used herein, is understood as meaning the group of alcohol oxidases which constitute a haem protein of the c type and contain FAD as cofactor and preferably additionally belong to the group of the enzyme with the database code AAS46878.1 (SEQ ID NO. 40) and variants thereof. Examples of flavin-containing alcohol dehydrogenases include the enzymes with the database codes AAS46878.1 (SEQ ID NO. 40), AA S46880.1 from *Candida tropicalis* and the enzyme with the database code CAB75351.1 from *Candida cloacae* (SEQ ID NO: 68).

According to the invention, a transaminase is used in step c). In a preferred embodiment, the term "transaminase", as used herein, is understood as meaning an enzyme which catalyses the transfer of α-amino groups from a donor, preferably an amino acid, to an acceptor molecule, preferably an α-ketocarboxylic acid. In a preferred embodiment, the term "amine donor", as used herein, is understood as meaning an L-amino acid, the amino group of which can be transferred from the transaminase to the α-ketocarboxylic acid with the formation of an amino acid. In a particularly preferred embodiment, the amine donor is L-alanine. In a preferred embodiment, the transaminase is selected from the group of transaminases and variants thereof which are characterized in that it has, at the position of the amino acid sequence which corresponds to Val224 from the transaminase of *Pseudomonas putida* GB-1 (database code YP_001668026.1), an amino acid selected from the group comprising isoleucine, valine, phenylalanine, methionine and leucine, and at the position of the amino acid sequence which corresponds to Gly230 from the transaminase from *Pseudomonas putida* GB-1 (database code YP_001668026.1), an amino acid other than threonine and preferably an amino acid from the group comprising serine, cysteine, glycine and alanine. In a particularly preferred embodiment, the transaminase is selected from the group which comprises the ω-transaminase from *Chromobacterium violaceum* DSM30191, transaminases from *Pseudomonas putida* GB-1, *Pseudomonas putida* W619, from *Pseudomonas aeruginosa* PA01, *Streptomyces coelicolor*

A3(2), *Pseudomonas putida* (database code YP_001668026) (SEQ ID NO. 48), *Pseudomonas putida* (datenbase code YP_001668026.1 or YP_001671460); *Rhodobacter sphaeroides* (strain ATCC 17023; database code YP_353455) and *Streptomyces avermitilis* MA 4680, and variants thereof.

In a preferred embodiment, the term "alanine dehydrogenase", as used herein, is understood as meaning an enzyme which catalyses the conversion of L-alanine with consumption of water and NAD(P)$^+$ to pyruvate, ammonia and NAD(P)H. Preferably, the alanine dehydrogenase is an intracellular alanine dehydrogenase, even more preferably a recombinant intracellular alanine dehydrogenase of a bacterial whole-cell catalyst. Examples include the enzymes from *Rhizobium leguminosarum* (database code YP_002975437), *Bacillus megaterium* (database code YP_003565624), *Rhodobacter capsulatus* (database code ADE84249.1) and *Bacillus subtilis* (database code NP_391071).

While the alcohol dehydrogenase in step b), if it is a NAD(P)-dependent one, consumes one molecule of the redox cofactor NAD(P)H per reacted substrate molecule, the amino dehydrogenase oxidizes NAD(P)H. Of particular advantage is therefore the use of a system in which alcohol dehydrogenase and amino acid dehydrogenase convert the same redox cofactor. NADP-dependent alcohol dehydrogenases include the enzyme from *E. coli* (YjgB, database code ZP_07117674) and a further enzyme from *E. coli* (YahK, database code BAE76108.1). NAD-dependent alcohol dehydrogenases include an enzyme from *E. coli* (AdhP, database code ZP_07145023), the enzyme from *Bacillus subtilis* (database code NP_391071), the enzyme from *Bacillus stearothermophilus* (database code P42328.1) and the enzyme from *Rhizobium leguminosarum* (database code YP_002975437). NADP-dependent alanine dehydrogenases include the enzyme from *Rhodobacter capsulatus* (database code ADE84249.1). NAD-dependent alanine dehydrogenases include the alanine dehydrogenase from *Bacillus subtilis* subsp. *subtilis* str. 168 (database code NP_391071) (SEQ ID NO. 22).

The teaching of the present invention can not only be carried out or applied using the, or on the, exact amino acid or nucleic acid sequences of the biological macromolecules described herein, but also using or on variants of those macromolecules which can be obtained by deleting, adding or substituting one or more than one amino acid or nucleic acid. In a preferred embodiment, the term "variant" of a nucleic acid sequence or amino acid sequence, which is used hereinbelow synonymously and exchangeably with the term "homologon", as used herein, means another nucleic acid or amino acid sequence which, with regard to the corresponding original wildtype nucleic acid or amino acid sequence, has a homology, used synonymously here with identity, of 70, 75, 80, 85, 90, 92, 94, 96, 98, 99% or more percent, where preferably amino acids other than those forming the catalytically active centre or amino acids essential for the structure or folding are deleted or substituted or such are merely conservatively substituted, for example a glutamate instead of an aspartate or a leucine instead of a valine. The prior art describes algorithms, which may be used to calculate the degree of homology of two sequences, e.g. Arthur Lesk (2008), Introduction to Bioinformatics, 3rd edition. In a further more preferred embodiment of the present invention, the variant of an amino acid or nucleic acid sequence, preferably in addition to the sequence homology mentioned above, has essentially the same enzymatic activity of the wildtype molecule and of the original molecule. For example, a variant of an enzymatically active polypeptide protease has the same, or essentially the same, proteolytic activity as the polypeptide enzyme, i.e. the capability to catalyse the hydrolysis of a peptide bond. In a particular embodiment, the term "essentially the same enzymatic activity" means an activity, with respect to the substrates of the wildtype polypeptide, which clearly lies above the background activity or/and differs from the $K_M$ and/or $k_{cat}$ values by less than 3, preferably 2, more preferably one order of magnitude, which the wildtype polypeptide exhibits with respect to the same substrates. In a further preferred embodiment, the term "variant" of a nucleic acid or amino acid sequence includes at least one active part/or fragment of the nucleic acid or amino acid sequence. In a further preferred embodiment, the term "active part", as used herein, means an amino acid sequence or a nucleic acid sequence which has a smaller than the full length of the amino acid sequence or codes for a smaller than the full length of the amino acid sequence, where the amino acid sequence or the coded amino acid sequence with the smaller length than the wildtype amino acid sequence has essentially the same enzymatic activity as the wildtype polypeptide or a variant thereof, for example as protease. In a particular embodiment, the term "variant" of a nucleic acid comprises a nucleic acid whose complementary strand, preferably under stringent conditions, binds to the wildtype nucleic acid. The stringency of the hybridization reaction is readily determinable by those skilled in the art and depends in general on the length of the probe, the washing temperatures and the salt concentration. Generally, longer probes require higher temperatures for the hybridization, whereas shorter probes work at lower temperatures. Whether hybridization takes place depends in general on the capability of the denatured DNA to anneal to complemetary strands which are present in its environment and below the melting temperature. The stringency of hybridization reaction and corresponding conditions are described in detail in F M Ausubel (1995), Current Protocols in Molecular Biology. John Wiley & Sons, Inc. Instructions for identifying DNA sequences by means of hybridization can be found by the person skilled in the art inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place in a preferred embodiment under stringent conditions, i.e. only hybrids are formed in which probe and target sequence, i.e. the polynucleotides treated with the probe, are at least 70% identical. It is known that the stringency of the hybridization including the washing steps is influenced and/or determined by varying the buffer composition, the temperature and the salt concentration. The hybridization reaction is generally carried out at a relatively lower stringency compared to the washing steps (Hybaid Hybridisation Guide, Hybaid Limited, Teddington, U K, 1996). For the hybridization reaction, for example, a buffer corresponding to 5×SSC buffer can be used at a temperature of about 50° C.-68° C. In this connection, probes can also hybridize with polynucleotides which have less than 70% identity to the sequence of the probe. Such hybrids are less stable and are removed by washing under stringent conditions. This can be achieved for example by lowering the salt concentration to 2×SSC and optionally subsequently 0.5×SSC (The DIG System User's Guide for Filter Hybridisation, Boehringer Mannheim, Mannheim, Germany, 1995), in which case a temperature of, increasing in order of preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. is established.

Temperature ranges from about 64° C.-68° C. or about 66° C.-68° C. are preferred. It is optionally possible to reduce the salt concentration down to a concentration corresponding to 0.2×SSC or 0.1×SSC. By means of a stepwise increase in the hybridization temperature in steps of about 1-2° C. from 50° C. to 68° C., polynucleotide fragments can be isolated which, for example in the order of increasing preference, at least 70% or at least 80% or at least 90%, at least 91%, at least 92%, at least 93%, at least 94%, at least 95%, at least 96%, at least 97%, at least 98% or at least 99% identity to the sequence of the nucleic acid molecule used. Further instructions relating to the hybridization are commercially available in the form of so-called kits (e.g. DIG Easy Hyb from Roche Diagnostics GmbH, Mannheim, Germany, Catalogue No. 1603558). In a preferred embodiment, the term "variant" of a nucleic acid, as used here, comprises any nucleic acid sequence which codes for the same amino acid sequence as the original nucleic acid or a variant of this amino acid sequence in terms of the degeneracy of the genetic code.

If a whole-cell catalyst is used according to the invention, then it is preferred if this is a cell which has an activity, reduced compared to its wildtype, of at least one enzyme which catalyses one of the reactions of the β-oxidation of fatty acids, with the enzyme preferably being selected from the group which includes fatty acid importer, fatty acid-CoA ligase, acyl-CoA dehydrogenase, 2,4-dienoyl-CoA reductase, enoyl-CoA hydratase and 3-ketoacyl-CoA thiolase. The β-oxidation of fatty acids is a widespread metabolic route which equally permits prokaryotic and eukaryotic organisms to oxidize fatty acids and to make available the chemical energy present therein to the metabolism (Y Fujita, H Matsuoka, and K Hirooka (2007) *Mol. Microbiology* 66(4), 829-839). In the further sense, it starts with the uptake of a fatty acid into the cell, in the case of *E. coli* by means of the transporter FadL (P N Black (1991) J. Bacteriol. 173, 435-442), which channels it through the outer or inner membrane of the Gram-negative bacteria cell and the FadD gene product (P N Black, C C DiRusso, A K Metzger, and T L Heimert (1992) J. Biol. Chem. 267, 25513-25520), which releases the fatty acid in the form of the CoA ester into the cytosol. There, if the conditions require it, the fatty acid is firstly oxidized at the β position of the CoA fatty acid ester by an acyl-CoA dehydrogenase, in the case of *E. coli* FadE (J. W. Campbell & J. E. Cronan (200) J. Bacteriol. 184, 3759-3764). A similar molecule can alternatively also be formed from a double-unsaturated fatty acid by reduction by means of a 2,4-dienoyl-CoA reductase, in the case of *E. coli* FadH. A multifunctional enzyme, the enoyl-CoA hydratase/3-hydroxyacyl-CoA dehydrogenase, in the case of *E. coli* FadB, then catalyses the hydration with the formation of the secondary alcohol and its subsequent oxidation to the ketone. In the last step, a 3-ketoacyl-CoA thiolase, in the case of *E. coli* FadA, catalyses the cleavage of the ketoacyl-CoA, with the result that acetyl-CoA and a CoA ester of the fatty acid that is two carbon atoms shorter compared to the starting molecule are released. If it is not likewise acetyl-CoA, the latter can be fed again into the β-oxidation cycle and be shortened via oxidation. Also involved in the regulation of the β-oxidation of fatty acids is FadR, a regulator of the Fad operon, which includes the genes required for the degradation of fatty acids, without FadR appearing to catalyse a reaction of the β-oxidation. In a preferred embodiment, the term "enzyme which catalyses one of the reactions of the β-oxidation of fatty acids" is understood as meaning any enzyme which interacts directly with the fatty acid substrate or a molecule formed therefrom on the route to the acetyl-CoA, preferably recognizes it as substrate, and catalyses its conversion to a metabolic product lying closer on this degradation route to the acetyl-CoA, preferably including the fatty acid importer, which effects the uptake of the fatty acid into the cell. For example, according to the preceding definition, these enzymes include acyl-CoA dehydrogenase since it interacts with the fatty acid-CoA ester and catalyses its conversion to the enyol-CoA, which lies closer to the acetyl-CoA on the metabolic route of the β-oxidation than the fatty acid-CoA ester. In a particularly preferred embodiment, the term "enzyme which catalyses one of the reactions of the β-oxidation of fatty acids", as used herein, is understood as meaning any enzyme from the group which comprises the gene products FadA, FadB, FadD, FadL and FadE from *E. coli* and/or their variants or homologues from other organisms. The gene products FadA, FadB, FadD, FadL and FadE from *E. coli* as well as variants and homologues from numerous other biotechnologically useful organisms and their nucleic acid and polypeptide sequences are described in the prior art, for example FadA under access number AP009048.1, FadB under access number BAE77457.1, FadD under access number BAA15609.1, FadE under access number BAA77891.2 and FadL under access number BAA16205.1

With the development of modern genetic, microbiological and molecular biological methods, numerous tools are available to the person skilled in the art with which he is able to routinely measure and influence the activity of enzymes present in living cells. To determine the activity of an enzyme which is present in the form of a suspension, a pellet or can be removed in processed form from a cell culture, enzymatic standard tests can be used and evaluated, as described in textbooks, for example A Cornish-Bowden (1995), Fundamentals of Enzyme Kinetics, Portland Press Limited. The prior art discloses numerous tests which are suitable specifically for measuring the activity of enzymes which catalyse one of the reactions of the β-oxidation of fatty acids, for example in K Kameda & W D Nunn (1981) J. Biol. Chem. 256, 5702-5707, Hi Marrakchi, W E DeWolf, C Quinn, J West, B J Polizzi, C Y So et al. (2003) Biochem. J. 370, 1055-1062, S Lobo, G Florova, and K A Reynolds (2001) Biochemistry 40 (39), 11955-64 and X Yu, T Liu, F Zhu, and C Khosla (2011) PNAS, electronic publication before printing. Routinely applicable processes for reducing the activity of an enzyme in a cell, for example by undirected mutagenesis of cells by exposure to radioactive radiation followed by enrichment or screening of the mutants, by site-directed insertion of point mutations or by the knock-out of a gene coding for an active enzyme integrated chromosomally into a cell are also described in the prior art, for example in Sambrook/Fritsch/Maniatis (1989): Molecular Cloning: A Laboratory Manual, Cold Spring Harbor Laboratory Press, 2nd edition or in Fuchs/Schlegel (2007) Allgemeine Mikrobiologie, 2008, Georg Thieme Verlag. In the particular case of the Fad gene product, the overexpression of a transcriptional repressor, for example of FadR (Y Fujita, H Matsuoka, and K Hirooka (2007) *Mol. Microbiology* 66(4), 829-839) is also appropriate for reducing the activity. A reduction in activity based on RNA interference (T Tuschl (2001) Chem Bio Chem 2: 239-145) or using specific inhibitors is also possible. In a preferred embodiment, the wording "where the cell has an activity reduced compared to its wildtype" of an enzyme, as used herein, means that the activity of the enzyme in the modified cell is reduced compared to the activity of the same enzyme in a wildtype cell. In a preferred embodiment, the relative reduction is, in order of increasing preference, 5, 10, 20, 40, 50, 75, 90, 95, 99 or more percent of the activity. In a particularly preferred embodiment, activity of the enzyme compared to the background can no longer be detected.

If a whole-cell catalyst is used according to the invention, then it is furthermore advantageous if the whole-cell catalyst is a cell which is an activity, reduced relative to the wildtype of the cell, of at least one endogenous aldehyde dehydrogenase. In a preferred embodiment, the term "endogenous aldehyde dehydrogenase", as used herein, is understood as meaning an enzyme which is able to catalyse the oxidation of an aldehyde to the corresponding carboxylic acid, and which is naturally present in the genome of the wildtype of the cell used. One example of an alcohol dehydrogenase endogenous for *E. coli* is the enzyme with the database code BAA15032.1 (AldA) and variants thereof.

The present application encompasses a sequence protocol with the following polypeptide (Polyp)- and nucleotide (DNA) sequences:

| SEQ ID NO | Type | Description |
| --- | --- | --- |
| 1 | Polyp | AlkL from *Pseudomonas oleovorans* (database code Q00595) |
| 2 | DNA | AlkL from *Pseudomonas oleovorans* (database code Q00595) |
| 3 | Polyp | AlkL from *Pseudomonas putida* (database code CAB69081) |
| 4 | DNA | AlkL from *Pseudomonas putida* (database code CAB69081) |
| 5 | Polyp | AlkL from *Marinobacter aquaeolei* VT8 (database code YP_957722) |
| 6 | DNA | AlkL from *Marinobacter aquaeolei* VT8 (database code YP_957722) |
| 7 | Polyp | AlkL from *Oceanicaulis alexandrii* HTCC2633 (database code ZP_00953584) |
| 8 | DNA | AlkL from *Oceanicaulis alexandrii* HTCC2633 (database code ZP_00953584) |
| 9 | Polyp | AlkL from *Marinobacter manganoxydans* Mnl7-9 (database code ZP_09158756) |
| 10 | DNA | AlkL from *Marinobacter manganoxydans* Mnl7-9 (database code ZP_09158756) |
| 11 | Polyp | AlkL from *Caulobacter* sp. K31 (database code YP_001672217) |
| 12 | DNA | AlkL from *Caulobacter* sp. K31 (database code YP_001672217) |
| 13 | Polyp | Ferredoxin reductase from *Alcanivorax borkumensis* SK2 (database code YP_691923) |
| 14 | DNA | Ferredoxin reductase from *Alcanivorax borkumensis* SK2 (database code YP_691923) |
| 15 | Polyp | Ferredoxin from *Alcanivorax borkumensis* SK2 (database code YP_691920) |
| 16 | DNA | Ferredoxin from *Alcanivorax borkumensis* SK2 (database code YP_691920) |
| 17 | Polyp | NAD-dependent alcohol dehydrogenase from *Escherichia coli* MS 187-1 (database code ZP_07145023) |
| 18 | DNA | NAD-dependent alcohol dehydrogenase from *Escherichia coli* MS 187-1 (database code ZP_07145023) |
| 19 | Polyp | CYP153 family from *Alcanivorax borkumensis* SK2 (database code YP_691921) |
| 20 | DNA | CYP153 family from *Alcanivorax borkumensis* SK2 (database code YP_691921) |
| 21 | Polyp | LL(I/L)(V/I)GGNDTTRN |
| 22 | Polyp | Alanine dehydrogenase from *Bacillus subtilis* subsp. *subtilis* str. 168 (database code NP_391071) |
| 23 | DNA | Alanine dehydrogenase from *Bacillus subtilis* subsp. *subtilis* str. 168 (database code NP_391071) |
| 24 | Polyp | Transaminase from *Chromobacterium violaceum* ATCC 12472 (database code NP_901695) |
| 25 | DNA | Transaminase from *Chromobacterium violaceum* ATCC 12472 (database code NP_901695) |
| 26 | Polyp | Oxidoreductase of the glucose-methanol-choline-oxidoreductase family (Deletion of AlkJ Q00593) |
| 27 | DNA | Oxidoreductase of the glucose-methanol-choline-oxidoreductase family (Deletion of AlkJ Q00593) |
| 28 | Polyp | Oxidoreductase of the glucose-methanol-choline-oxidoreductase family YP_694430 (Ab_AlkJ) |
| 29 | DNA | Oxidoreductase of the glucose-methanol-choline-oxidoreductase family YP_694430 (Ab_AlkJ) |
| 30 | Polyp | Ferredoxin reductase (YP_957889(Maqu_FdOR) |
| 31 | DNA | Ferredoxin reductase (YP_957889(Maqu_FdOR) |
| 32 | Polyp | Ferredoxin reductase (BAE78453 (Ac_FdOR)) |
| 33 | DNA | Ferredoxin reductase (BAE78453 (Ac_FdOR)) |
| 34 | Polyp | Ferredoxin YP_957887 (Maqu_Fd) |
| 35 | DNA | Ferredoxin YP_957887 (Maqu_Fd) |
| 36 | Polyp | Ferredoxin BAE78451 (Ac_Fd) |
| 37 | DNA | Ferredoxin BAE78451 (Ac_Fd) |
| 38 | Polyp | Oxidoreductase of the glucose-methanol-choline-oxidoreductase family from *Caulobacter* sp. K31 (database code ABZ74557.1) |
| 39 | DNA | Oxidoreductase of the glucose-methanol-choline-oxidoreductase family from *Caulobacter* sp. K31 (database code ABZ74557.1) |

-continued

| SEQ ID NO | Type | Description |
|---|---|---|
| 40 | Polyp | Flavin-containing alcohol dehydrogenase from *Candida tropicalis* (database code AAS46878.1) |
| 41 | DNA | Flavin-containing alcohol dehydrogenase from *Candida tropicalis* (database code AAS46878.1) |
| 42 | Polyp | CYP153 family from *Marinobacter aquaeolei* VT8 (database code YP_ YP_957888) |
| 43 | DNA | CYP153 family from *Marinobacter aquaeolei* VT8 (database code YP_ YP_957888) |
| 44 | Polyp | CYP153 family from *Acinetobacter* sp. OC4 (database code YP_ YP_957888) |
| 45 | DNA | CYP153 family from *Acinetobacter* sp. OC4 (database code YP_ YP_957888) |
| 46 | Polyp | Alcohol dehydrogenase from *Pseudomonas putida* (database code CAB54054) |
| 47 | DNA | Alcohol dehydrogenase from *Pseudomonas putida* (database code CAB54054) |
| 48 | Polyp | Aminotransferase from *Pseudomonase putida* (database code YP_001668026) |
| 49 | DNA | Aminotransferase from *Pseudomonase putida* (database code YP_001668026) |
| 50 | DNA | AlkB promoter |
| 51 | DNA | Primer Fd_CYP153 |
| 52 | DNA | Primer pHg-LL-08 |
| 53 | DNA | Primer pHg-LL-09 |
| 54 | DNA | Primer pHg-LL-10 |
| 55 | DNA | Primer pHg-LL-11 |
| 56 | DNA | Primer pHg-LL-06 |
| 57 | DNA | Vector pCOM10 |
| 58 | DNA | Expression vector pCOM[Ab_Fd/CYP153-2/FdOR/alkL] |
| 59 | Polyp | CYP52 family from *Candida tropicalis* (database code AAO73952) |
| 60 | DNA | CYP52A |
| 61 | Polyp | CYP52 family from *Candida tropicalis* (database code AAO73958) |
| 62 | DNA | CYP52 family from *Candida tropicalis* (database code AAO73958) |
| 63 | Polyp | NADPH-dependent cytochrome P450 oxidoreductase (database code P37201) |
| 64 | DNA | NADPH-dependent cytochrome P450 oxidoreductase (database code P37201) |
| 65 | DNA | pCOM10-Ct CYP52A12_co plus OR_co |
| 66 | DNA | pCOM10-Ct CYP52A17_co plus OR_co |

The present invention is further illustrated by the following FIGURES and non-limiting examples, from which further features, embodiments, aspects and advantages of the present invention may be taken.

EXAMPLE 1

Preparation of Expression Vectors for the Genes CYP153, Fd and FdOR from *Alcanivorax borkumensis* SK2 and alkL from *Pseudomonas oleovorans*

To prepare an *E. coli* expression vector for the genes CYP153 (SEQ ID No. 20), Fd (SEQ ID No. 16) and FdOR (SEQ ID No. 14) from *Alcanivorax borkumensis*, as well as the gene alkL (SEQ ID No. 2) from *Pseudomonas oleovorans*, the genes were cloned under the control of the alkB promotor (SEQ ID No. 50) in the plasmid pCOM10. The different DNA fragments were amplified by inserting homologous regions for recombination cloning. The template used was the respective chromosomal DNA.

The following oligonucleotides were used for the amplification of the respective fragments:

Fd_CYP153
pHg-LL-07:
(SEQ ID No. 51)
5'-TTAATAAAAATTGGAGTACAGACTTTTGGTAGGAGAATGC-3' pHg-LL-08:
(SEQ ID No. 52)
5'-CCTTGGGCTTATTTTTTAGCCGTCAACTTAAC-3'

FdOR
pHg-LL-09:
(SEQ ID No. 53)
5'-AAAAATAAGCCCAAGGCACAGATAAAGAGAGA-3' pHg-LL-10:
(SEQ ID No. 54)
5'-TAGATCCTTCAGATCAAAGACTTTAATTCAAC-3' alkL
pHg-LL-11:
(SEQ ID No. 55)
5'-TGATCTGAAGGATCTAGGAACCAAGGAGAGTG-3' pHg-LL-06:
(SEQ ID No. 56)
5'-CTTGGCTGCAGGTCGATTAGAAAACATATGACGCACCAAG-3'

The following parameters were used for the PCR:

| Fd-CYP153: | | | |
|---|---|---|---|
| Denaturation: | 98° C. | 30 s | |
| Denaturation: | 98° C. | 10 s | 35x |
| Annealing: | 62° C. | 20 s | 35x |

| | | | |
|---|---|---|---|
| Elongation: | 72° C. | 1:10 min | 35x |
| Final elongation: | 72° C. | 10 min | |
| FdOR | | | |
| Denaturation: | 98 ° C. | 30 s | |
| Denaturation: | 98° C. | 10 s | 35x |
| Annealing: | 53° C. | 20 s | 35x |
| Elongation: | 72° C. | 55 s | 35x |
| Final elongation: | 72° C. | 10 min | |
| alkL | | | |
| Denaturation: | 98° C. | 30 s | |
| Denaturation: | 98° C. | 10 s | 25x |
| Annealing: | 65° C. | 20 s | 25x |
| Elongation: | 72° C. | 18 s | 25x |
| Final elongation: | 72° C. | 10 min | |

For the amplification, the Phusion™ High-Fidelity Master Mix from New England Biolabs (Frankfurt) was used according to the manufacturer's recommendations. In each case, 50 µl of the PCR reactions were then separated on a 1% strength TAE agarose gel. The implementation of the PCR, of the agarose gel electrophoresis, of the ethidium bromide staining of the DNA and determination of the PCR fragment sizes was performed in the manner known to the person skilled in the art. In all cases, PCR fragments of the expected size could be amplified (Fd-CYP153: 1800 bp; FdOR: 1276 bp; alkL: 745 bp). For isolating and purifying the DNA, the PCR products were cut out of a preparative gel using a scalpel and purified using the QiaQuick Gel extraction Kit in accordance with the manufacturer's instructions (Qiagen, Hilden). The purified PCR products were cloned using the Geneart® Seamless Cloning and Assembly Kit in accordance with the manufacturer's instructions (Life Technologies, Carlsbad, Calif., USA) into a pCOM10 vector cleaved with EcoRI-HF and SalI (SEQ ID No. 57) behind the alkB promotor (SEQ ID No. 50). The transformation of chemically competent E. coli 10 beta cells (New England Biolabs, Frankfurt) was carried out in the manner known to the person skilled in the art. The correct insertion of the target genes was checked by restriction analysis and the authenticity of the inserted genes confirmed by DNA sequencing. The resulting expression vector was referred to as pCOM[Ab_Fd/CYP153-2/FdOR/alkL] (SEQ ID No. 58).

EXAMPLE 2

Preparation of Expression Vectors for the Genes CYP52A12 and OR from Candida tropicalis, and Also alkL from Pseudomonas oleovorans To prepare an E. coli expression vector for the genes CYP52A12 (SEQ ID No. 60) and OR (SEQ ID No. 64) from Candida tropicalis, and also the gene alkL (SEQ ID No. 2) from Pseudomonas oleovorans, the genes CYP52A12 and OR were codon-optimized for the expression in Escherichia coli in silico and synthesized together with the gene alkL as operon. During the synthesis, cleavage sites for AscI and SalI were inserted upstream of the CYP52A12 gene and downstream of the alkL gene. The synthesized DNA fragment CYP52A12 OR alkL was digested with the restriction endonucleases AscI and SalI, ligated into the correspondingly cleaved vector pCOM10 and the product was transformed into chemically competent E. coli 10 beta cells (New England Biolabs, Frankfurt). The finished vector was referred to as pCOM10-Ct CYP52A12_co plus OR_co (SEQ ID No. 65).

EXAMPLE 3

Preparation of Expression Vectors for the Genes CYP52A17 and OR from Candida tropicalis, and alkL from Pseudomonas oleovorans To prepare an E. coli expression vector for the genes CYP52A17 (SEQ ID No. 62), and OR (SEQ ID No. 64) from Candida tropicalis, and also the gene alkL (SEQ ID No. 2) from Pseudomonas oleovorans, the genes CYP52A17 and OR were codon-optimized for the expression in Escherichia coli in silico and synthesized together with the gene alkL as operon. During the synthesis, cleavage sites for AscI and SalI were inserted upstream of the CYP52A17 gene and downstream of the alkL-gene. The synthesized DNA fragment CYP52A12 OR alkL was digested with the restriction endonucleases AscI and SalI, ligated into the correspondingly cleaved vector pCOM10 and the product was transformed into chemically competent E. coli 10 beta cells (New England Biolabs, Frankfurt). The finished vector was referred to as pCOM10-Ct CYP52A17_co plus OR_co (SEQ ID No. 66).

EXAMPLE 4

Production of Methyl Hydroxylaurate by an E. coli Strain with Expression Vectors for the Genes CYP153, Fd and FdOR from Alcanivorax borkumensis SK2 and alkL from Pseudomonas oleovorans, or for the Genes CYP52A17 and OR from Candida tropicalis and alkL from Pseudomonas oleovorans To produce an E. coli strain with the expression vector pCOM[Ab_Fd/CYP153-2/FdOR/alkL] or pCOM10-Ct CYP52A17_co plus OR_co, electrocompetent cells of E. coli W3110 were prepared. This was carried out in a manner known to the person skilled in the art. E. coli W3110 was transformed in each case with one of the two listed plasmids and plated out onto LB-agar plates with kanamycin (50 µg/ml). Transformants were checked as regards the presence of the correct plasmids by plasmid preparation and analytical restriction analysis. The following strains were constructed in this way:

E. coli W3110 pCOM[Ab_Fd/CYP153-2/FdOR/alkL]
E. coli W3110 pCOM10-Ct CYP52A17_co plus OR_co The strains were subjected to a fed-batch fermentation in order to investigate their ability to produce methyl hydroxylaurate, methyl oxolaurate and methyl carboxylaurate from methyl laurate. This was carried out in an 8-fold parallel fermentation system from DASGIP.

For the fermentation, 1 l reactors were used which were equipped with overhead stirrers and impeller turbines. To monitor the process, pH and $pO_2$ were measured online. OTR/CTR measurements served inter alia for estimating the metabolic activity and fitness of the cells.

The pH probes were calibrated by means of a two-point calibration with measurement solutions of pH 4.0 and pH 7.0 according to technical reference of DASGIP. The reactors were provided according to technical reference with the required sensors and connections and the stirrer shaft was installed. The reactors were then filled with 300 ml of water and autoclaved for 20 min at 121° C. in order to ensure sterility. The $pO_2$ probes were polarized overnight (at least 6 h) following connection to the measurement amplifier. The water was then removed under the clean bench and replaced by high-cell-density medium consisting of $(NH_4)_2SO_4$ 1.76 g/l, $K_2HPO_4$ 19.08 g/l, $KH_2PO_4$ 12.5 g/l, yeast extracts 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2*4H_2O$ 1.91 g/l, $ZnSO_4*7H_2O$ 1.87 g/l, ethylenediaminetetraacetic acid dihydrate 0.84 g/l, $H_3BO_3$ 0.30 g/l, $Na_2MoO_4*2H_2O$ 0.25 g/l, $CaCl_2*2H_2O$ 4.70 g/l, $FeSO_4*7H_2O$ 17.80 g/l, $CuCl_2*2H_2O$ 0.15 g/l) with 15 g/l glucose as carbon source (added by metered addition of 30 ml/l of a sterile feed solution consisting of 500 g/l glucose, 1% (w/v) $MgSO_4*7H_2O$ and 2.2% (w/v) $NH_4Cl$) with 50 mg/l kanamycin.

Subsequently, the $pO_2$ probes were calibrated using a single-point calibration (stirrer: 600 rpm/gassing: 10 sL/h air) to 100% and the feed, correction agent and induction agent stretches were cleaned by means of cleaning-in-place according to technical reference. For this, the tubes were firstly flushed with 70% ethanol, then with 1 M NaOH, then with sterile demineralized water and finally filled with the respective media.

All of the aforementioned *E. coli* strains were cultured firstly from a cryoculture in LB medium (25 ml in a 100 ml chicane flask) with 50 mg/l kanamycin overnight at 37° C. and 200 rpm for about 18 h. Then, 2 ml of this culture were transferred for a second preculture stage into 25 ml of high-cell-density medium consisting of $(NH_4)_2SO_4$ 1.76 g/L, $K_2HPO_4$ 19.08 g/l, $KH_2PO_4$ 12.5 g/l, yeast extract 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2*4H_2O$ 1.91 g/l, $ZnSO_4*7H_2O$ 1.87 g/l, ethylenediaminetetraacetic acid dihydrate 0.84 g/l, $H_3BO_3$ 0.30 g/l. $Na_2MoO_4*2H_2O$ 0.25 g/l, $CaCl_2*2H_2O$ 4.70 g/l, $FeSO_4*7H_2O$ 17.80 g/l, $CuCl_2*2H_2O$ 0.15 g/l) with 15 g/l glucose as carbon source (added by metered addition of 30 ml/l of a sterile feed solution consisting of 500 g/l glucose, 1% (w/v) $MgSO_4*7H_2O$ and 2.2% (w/v) $NH_4Cl$) with the already described antibiotics in a 100 ml shake flask and incubated at 37° C./200 rpm for a further 6 h.

In order to inoculate the reactors with an optical density of 0.1, the $OD_{600}$ of the second preculture stage was measured and the amount of culture required for the inoculation was calculated. The required amount of culture was added with the help of a 5 ml syringe through a septum into the heat-treated and aerated reactor.

The following standard program was used:

| DO regulator | | pH regulator | |
| --- | --- | --- | --- |
| Preset | 0% | Preset | 0 ml/h |
| P | 0.1 | P | 5 |
| Ti | 300 s | Ti | 200 s |
| min | 0% | min | 0 ml/h |
| max | 100% | max | 40 ml/h |

| N (Rotation) | from | to | XO2 (gas mixture) | from | to | F (gas flow rate) | from | to |
| --- | --- | --- | --- | --- | --- | --- | --- | --- |
| growth and biotransformation | 0% 400 rpm | 30% 1500 rpm | growth and biotransformation | 0% 21% | 100% 21% | growth and biotransformation | 15% 6 sL/h | 80% 72 sL/h |

| Script | |
| --- | --- |
| Trigger sharp | 31% DO (1/60h) |
| Induction | 10 h after feed |
| DCPK | start |
| Feed trigger | 50% DO |
| Feed rate | 3 [ml/h] |

The pH was regulated to pH 6.8 on one side with 12.5% strength ammonia solution. During cultivation and biotransformation, the dissolved oxygen ($pO_2$ or DO) in the culture was regulated to at least 30% by means of stirrer feed and gassing rate. Following inoculation, the DO dropped from 100% to this 30%, where it was kept stable for the remainder of the fermentation.

The fermentation was carried out as fed-batch, where the feed start was triggered as delivery to the feed phase with 5 g/l*h glucose feed, consisting of 500 g/l glucose, 1% (w/v) $MgSO_4*7H_2O$ and 2.2% (w/v) $NH_4Cl$, via the DO peak inducing the end of the batch phase. With feed start, the temperature of 37° C. was lowered to 30° C. 10 h after feed start, the expression of the oxidation genes was induced with 0.025% (v/v) DCPK. The start of the methyl hydroxylaurate production (=start of the biotransformation) was carried out 14 h after feed start. For this purpose, 150 ml of a mixture of methyl laurate and oleic acid (technical-grade 90%) were added as batch to the fermentation broth.

To quantify LSME and HLS in fermentation samples, samples were taken 1/2/4/20/22 h after the start of biotransformation. These samples were prepared for analysis. (see LC-ESI/$MS^2$-based quantification of products).

LC-ESI/$MS^2$-Based Quantification of Products

The quantification of LSME and HCL in fermentation samples was carried out by means of LC-ESI/$MS^2$ by reference to an external calibration for all analytes (0.1-50 mg/l) and using the internal standard aminoundecanoic acid (AUD for HLSME), and d3-LSME (for LSME).

The following instruments were used here:
- HPLC system 1260 (Agilent; Böblingen) with autosampler (G1367E), binary pump (G1312B) and column oven (G1316A)
- Mass spectrometer TripelQuad 6410 (Agilent; Böblingen) with ESI source
- HPLC column: Kinetex C18, 100×2.1 mm, particle size: 2.6 μm, pore size 100 Å (Phenomenex; Aschaffenburg)
- Precolumn: KrudKatcher Ultra HPLC In-Line Filter; 0.5 μm filter depth and 0.004 mm internal diameter (Phenomenex; Aschaffenburg)

The samples were prepared by pipetting 1900 μl of solvent (80% (v/v) acetonitrile, 20% double-distilled $H_2O$ (v/v), +0.1% formic acid) and 100 μl sample in a 2-ml reaction vessel. The mixture was vortexed for about 10 seconds and then centrifuged at about 13 000 rpm for 5 min. The clear supernatant was removed using a pipette and, after appropriate dilution, analysed with diluents (80% (v/v) ACN, 20% double-distilled. $H_2O$ (v/v), +0.1% formic acid).

100 µL of ISTD were pipetted into each 900 µL sample (10 µL for a sample volume of 90 µL).

The HPLC separation was carried out with the aforementioned column and precolumn. The injection volume was 0.7 µL, the column temperature 50° C., the flow rate 0.6 mL/min. The mobile phase consisted of eluent A (0.1% strength (v/v) aqueous formic acid) and eluent B (acetonitrile with 0.1% (v/v) formic acid). The following gradient profile was used:

| Time [min] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

The ESI-MS$^2$ analysis was carried out in the positive mode with the following parameters of the ESI source:

Gas temperature 280° C.

Gas flow rate 11 L/min

Nebulizing pressure 50 psi

Capillary voltage 4000 V

The detection and quantification of the compounds DDS, DDSME, HLS, HLSME, OLS, OLSME was carried out with the following MRM parameters, with in each case a product ion being used as qualifier and one as quantifier

| Analyte | Precursor ion [m/z] | Product ion [m/z] | Residence time [ms] | Collision energy [eV] |
|---|---|---|---|---|
| HLSME | 231.3 | 181.2 | 15 | 2 |
| HLSME | 231.3 | 163.2 | 25 | 5 |

The analyte LSME was detected in the SIM mode (m/z 201 and 215).

It was able to be shown that the strain E. coli W3110 pCOM[Ab_Fd/CYP153-2/FdOR/alkL] is able to form methyl w-hydroxylaurate from methyl laurate. The strain E. coli W3110 pCOM10-Ct CYP52A17_co plus OR_co was able to convert methyllaurate to methyl ω-hydroxylaurate or further oxidation products only to a considerably lesser extent.

The concentrations of methyl laurate and methyl ω-hydroxylaurate are given after a fermentation time of 22 hours.

| Strain | C (Lauric acid) methylester [g/L] | C (ω-Hydroxyacid methylester) [g/L] |
|---|---|---|
| E. coli W3110 pCOM[Ab_Fd/CYP153-2/FdOR/alkL] | 88.1 | 4.35 |
| E. coli W3110 pCOM10-Ct CYP52A17_co plus OR_co | 106.9 | <0.1 |

EXAMPLE 5

Prophetic

Production of Methyl Hydroxylaurate by an *E. coli* Strain with Expression Vectors for the Genes CYP153, Fd and FdOR from *Alcanivorax Borkumensis* SK2 and alkL from *Pseudomonas oleovorans* or for the Genes CYP52A12 and OR from *Candida tropicalis* and alkL from *Pseudomonas oleovorans*

To produce an *E. coli* strain with the expression vector pCOM[Ab_Fd/CYP153-2/FdOR/alkL] or pCOM10-Ct CYP52A12_co plus OR_co, electrocompetent cells of *E. coli* W3110 are prepared. This is carried out in a manner known to the person skilled in the art. *E. coli* W3110 is transformed in each case with one of the two listed plasmids and plated out onto LB-agar plates with kanamycin (50 µg/ml). Transformants are tested as regards the presence of the correct plasmids by plasmid preparation and analytical restriction analysis. The following strains are constructed in this way:

*E. coli* W3110 pCOM[Ab_Fd/CYP153-2/FdOR/alkL]

*E. coli* W3110 pCOM10-Ct CYP52A12_co plus OR_co

The strains are subjected to a fed-batch fermentation in order to investigate their ability to produce HLSME. This is carried out in an 8-fold parallel fermentation system from DASGIP. 1 L reactors equipped with overhead stirrers and impeller turbines are used for the fermentation. pH and pO$_2$ are measured online for monitoring the process. OTR/CTR measurements serve inter alia to estimate the metabolic activity and fitness of the cells.

The pH probes are calibrated by means of a two-point calibration with measurement solutions of pH 4.0 and pH 7.0 according to technical reference from DASGIP. The reactors are provided according to technical reference with the required sensors and connections and the stirrer shaft is installed. Then, the reactors are filled with 300 mL of water and autoclaved for 20 min at 121° C. in order to ensure sterility. The pO$_2$ probes are polarized overnight (at least 6 h) following connection to the measurement amplifier. The water is then removed under the clean bench and replaced by high-cell-density medium consisting of (NH$_4$)$_2$SO4 1.76 g/L, K$_2$HPO$_4$ 19.08 g/L, KH$_2$PO$_4$ 12.5 g/L, yeast extract 6.66 g/L, trisodium citrate dihydrate 11.2 g/L, 17 mL/L of a filter-sterilized 1% strength ammonium iron citrate solution, and 5 mL/L of a filter-sterilized trace element strain solution (consisting of HCl (37%) 36.50 g/L, MnCl$_2$*4H$_2$O 1.91 g/L, ZnSO$_4$*7H$_2$O 1.87 g/L, ethylenediaminetetraacetic acid dihydrate 0.84 g/L, H$_3$BO$_3$ 0.30 g/L. Na$_2$MoO$_4$*2H$_2$O 0.25 g/L, CaCl$_2$*2H$_2$O 4.70 g/L, FeSO$_4$*7H$_2$O 17.80 g/L, CuCl$_2$*2H$_2$O 0.15 g/L) with 15 g/L glucose as carbon source (added by metered addition of 30 mL/L of a sterile feed solution consisting of 500 g/L glucose, 1% (w/v) MgSO$_4$*7H$_2$O and 2.2% (w/v) NH$_4$Cl) with 50 mg/L kanamycin.

Subsequently, the pO$_2$ probes are calibrated with a single-point calibration (stirrer: 600 rpm/gassing: 10 sL/h air) to 100%, and the feed, correcting agent and induction agent stretches are cleaned by means of cleaning-in-place according to technical reference. For this, the tubes are first flushed with 70% ethanol, then with 1 M NaOH, then with sterile demineralized water, and finally filled with the respective media.

All of the aforementioned *E. coli* strains are first cultivated from a cryoculture in LB medium (25 mL in a 100 mL shake flask) with 50 mg/L kanamycin overnight at 37° C. and 200 rpm for about 18 h. Then, 2 mL of this culture are transferred for a second preculture stage in 25 mL of high-cell-density medium consisting of $(NH_4)_2SO_4$ 1.76 g/L, $K_2HPO_4$ 19.08 g/L, $KH_2PO_4$ 12.5 g/L, yeast extract 6.66 g/L, trisodium citrate dihydrate 11.2 g/L, 17 mL/L of a filter-sterilized 1% strength ammonium iron citrate solution, and 5 mL/L of a filter-sterilized trace element strain solution (consisting of HCl (37%) 36.50 g/L, $MnCl_2*4H_2O$ 1.91 g/L, $ZnSO_4*7H_2O$ 1.87 g/L, ethylenediaminetetraacetic acid dihydrate 0.84 g/L, $H_3BO_3$ 0.30 g/L. $Na_2MoO_4*2H_2O$ 0.25 g/L, $CaCl_2*2H_2O$ 4.70 g/L, $FeSO_4*7H_2O$ 17.80 g/L, $CuCl_2*2H_2O$ 0.15 g/L) with 15 g/L glucose as carbon source (added by metered addition of 30 mL/L of a sterile feed solution consisting of 500 g/L glucose, 1% (w/v) $MgSO_4*7H_2O$ and 2.2% (w/v) $NH_4Cl$) with the already described antibiotics in a 100 mL shake flask and incubated at 37° C./200 rpm for a further 6 h.

In order to inoculate the reactors with an optical density of 0.1, the $OD_{600}$ of the second preculture stage is measured and the amount of culture required for the inoculation is calculated. The amount of culture required is added with the help of a 5 mL syringe through a septum into the heat-treated and aerated reactor.

The following standard program is used:

| DO regulator | | pH regulator | |
|---|---|---|---|
| Preset | 0% | Preset | 0 ml/h |
| P | 0.1 | P | 5 |
| Ti | 300 s | Ti | 200 s |
| min | 0% | min | 0 mL/h |
| max | 100% | max | 40 mL/h |

| N (rotation) | from | to | XO2 (gas mixture) | from | to | F (gas flow rate) | from | to |
|---|---|---|---|---|---|---|---|---|
| Growth and biotransformation | 0% 400 rpm | 30% 1500 rpm | Growth and biotransformation | 0% 21% | 100% 21% | Growth and biotransformation | 15% 6 sL/h | 80% 72 sL/h |

| Script | |
|---|---|
| Trigger sharp | 31% DO (1/60 h) |
| Induction DCPK | 10 h after feed start |
| Feed trigger | 50% DO |
| Feed rate | 3 [mL/h] |

The pH is regulated to pH 6.8 on one side with 12.5% strength ammonia solution. During cultivation and biotransformation, the dissolved oxygen ($pO_2$ or DO) in the culture is regulated to at least 30% via stirrer speed and gassing rate. Following inoculation, the DO drops from 100% to this 30%, where it is kept stable for the remainder of the fermentation.

The fermentation is carried out as fed batch, where the feed start is triggered as entry to the feed phase with 5 g/L*h glucose feed, consisting of 500 g/L glucose, 1% (w/v) $MgSO_4*7H_2O$ and 2.2% (w/v) $NH_4Cl$, via the DO peak indicating the end of the batch phase. With feed start, the temperature is lowered from 37° C. to 30° C. 10 h after feed start, the expression of the oxidation genes is induced with 0.025% (v/v) DCPK. The start of the methyl hydroxylaurate production (=start of the biotransformation) takes place 14 h after feed start. For this, 150 mL of a mixture of methyl laurate and oleic acid (technical-grade 90%) were added as batch to the fermentation broth.

For quantification of LSME and HLSME, fermentation samples are taken 1/2/4/20/22 h after the start of biotransformation. These samples are prepared for analysis. (See LC-ESI/MS$^2$-based quantification of products).

LC-ESI/MS$^2$-Based Quantification of Products.

The quantification of LSME and HLSME in fermentation samples takes place by means of LC-ESI/MS$^2$ by reference to an external calibration for all analytes (0.1-50 mg/L) and using the internal standard aminoundecanoic acid (AUD for HLSME) and d3-LSME (for LSME).

The following equipment is used here:
- HPLC system 1260 (Agilent; Böblingen) with autosampler (G1367E), binary pump (G1312B) and column oven (G1316A)
- Mass spectrometer TripelQuad 6410 (Agilent; Böblingen) with ESI source
- HPLC column: Kinetex C18, 100×2.1 mm, particle size: 2.6 μm, pore size 100 Å (Phenomenex; Aschaffenburg)
- Precolumn: KrudKatcher Ultra HPLC In-Line Filter; 0.5 μm filter depth and 0.004 mm internal diameter (Phenomenex; Aschaffenburg)

The samples are prepared by pipetting 1900 μL of solvent (80% (v/v) of acetonitrile, 20% double-distilled $H_2O$ (v/v), +0.1% formic acid) and 100 μL of sample in a 2-mL reaction vessel. The mixture is vortexed for about 10 seconds and then centrifuged at about 13 000 rpm for 5 min. The clear supernatant is removed using a pipette and analysed following appropriate dilution with diluent (80% (v/v) ACN, 20% double-distilled $H_2O$ (v/v), +0.1% formic acid). 100 μL of ISTD are pipetted in for each 900 μL of sample (10 μL for a sample volume of 90 μL).

The HPLC separation takes place with the aforementioned column or precolumn. The injection volume is 0.7 μL, the column temperature is 50° C., and the flow rate is 0.6 mL/min. The mobile phase consists of eluent A (0.1% strength (v/v) aqueous formic acid) and eluent B (acetonitrile with 0.1% (v/v) formic acid). The following gradient profile is used:

| Time [min] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

The ESI-MS$^2$ analysis takes place in the positive mode with the following parameters of the ESI source:

Gas temperature 280° C.

Gas flow rate 11 L/min

Nebulizer pressure 50 psi
Capillary voltage 4000 V

The detection and quantification of the compound HLSME takes place with the following MRM parameters, with in each case one product ion being used as qualifier and one as quantifier

| Analyte | Precursor ion [m/z] | Product ion [m/z] | Residence time [ms] | Collision energy [eV] |
|---|---|---|---|---|
| HLSME | 231.3 | 181.2 | 15 | 2 |
| HLSME | 231.3 | 163.2 | 25 | 5 |

The analyte is detected in the SIM mode (m/z 201 and 215).

It is found that the strain E. coli W3110 pCOM[Ab_Fd/CYP153-2/FdOR/alkL] is able to form methyl w-hydroxylaurate from methyl laurate. The strain E. coli W3110 pCOM10-Ct CYP52A12_co plus OR_co can convert methyl laurate to methyl ω-hydroxylaurate or other oxidation products only to a lesser extent.

The features of the invention disclosed in the preceding description, the claims and the examples may be essential both individually and also in any desired combination for realizing the invention in its various embodiments.

The invention claimed is:

1. A method for oxidizing a fatty acid or an ester of the formula (I):

H₃C—(CH₂)ₙ—COOR  (I), where R is H, methyl, ethyl, propyl or butyl, and n is an integer from 6 to 30,
the method comprising:
a) contacting the fatty acid or the ester with a cytochrome P450 monooxygenase of the CYP153 family in the presence of molecular oxygen, NAD(P)H, and an electron donor, such that the fatty acid or the ester is oxidized and at least one fatty acid alcohol is produced, wherein the cytochrome P450 monooxygenase of the CYP153 family comprises a peptide having the amino acid sequence of SEQ ID NO: 21;
b) contacting the fatty acid alcohol produced in a) with an alcohol dehydrogenase, such that the fatty acid alcohol reacts with the alcohol dehydrogenase, and aldehyde or ketone is produced; and
c) contacting the aldehyde or ketone produced in b) with a transaminase in the presence of an amine donor, such that the aldehyde or ketone is aminated,
wherein the contacting in a), b), and c) occurs in the presence of a cell which is genetically transformed to have a vector having a gene encoding the cytochrome P450 monooxygenase of the CYP153 family and at least one additional gene selected from the group consisting of a gene encoding the alcohol dehydrogenase and a gene encoding the transaminase, such that the cell expresses the cytochrome P450 monooxygenase of the CYP153 family, and at least one of the alcohol dehydrogenase and the transaminase.

2. The method according to claim 1, wherein the alcohol dehydrogenase is selected from the group consisting of
a NAD(P)⁺-dependent alcohol dehydrogenase,
an alcohol dehydrogenase from *Pseudomonas putida* comprising the amino acid sequence of SEQ ID NO: 46 or a variant thereof, wherein the variant of the alcohol dehydrogenase from *Pseudomonas putida* has at least 70% homology to the amino acid sequence of SEQ ID NO: 46,
a flavin-containing alcohol dehydrogenase from *Candida tropicalis* comprising the amino acid sequence of SEQ ID NO: 40 or a variant thereof, wherein the variant of the flavin-containing alcohol dehydrogenase from *Candida tropicalis* has at least 70% homology to the amino acid sequence of SEQ ID NO: 40, and
a flavin-containing alcohol dehydrogenase from *Candida cloacae* comprising the amino acid sequence of SEQ ID NO: 68 or a variant thereof, wherein the variant of the flavin-containing alcohol dehydrogenase from *Candida cloacae* has at least 70% homology to the amino acid sequence of SEQ ID NO: 68.

3. The method according to claim 1, wherein the electron donor is at least one of a ferredoxin reductase and a ferredoxin.

4. The method according to claim 1,
wherein the contacting in c) is carried out in the presence of an alanine dehydrogenase, ammonia, and NADH, and
the alanine dehydrogenase is an alanine dehydrogenase from *Bacillus subtilis* subsp. *subtilis* str. 168 having the amino acid sequence of SEQ ID NO: 22 or an alanine dehydrogenase having an amino acid sequence having at least 70% homology to the amino acid sequence of SEQ ID NO: 22.

5. The method according to claim 1,
wherein the electron donor is at least one of a ferredoxin reductase and a ferredoxin, and
the contacting in c) is carried out in the presence of an alanine dehydrogenase, ammonia, and NAD(P)H.

6. The method according to claim 5, wherein the vector further has a gene encoding the ferredoxin reductase, a gene encoding the ferredoxin, or both, such that the cell further expresses the ferredoxin reductase, the ferredoxin, or both.

7. The method according to claim 1, wherein the cell further expresses an AlkL polypeptide having the amino acid sequence of SEQ ID NO: 1, SEQ NO: 3, SEQ ID NO: 5, SEQ ID NO: 7, SEQ NO: 9, or SEQ ID NO: 11.

8. The method according to claim 1,
wherein the cell has a reduced activity of an enzyme which catalyzes at least one reaction of β-oxidation of a fatty acid, compared to an activity in a corresponding wildtype cell, and
the enzyme is at least one selected from the group consisting of FadA, FadB, FadD, FadL, and FadE from *Escherichia coli*.

9. The method according to claim 1, wherein the contacting in c) is carried out in the presence of an alanine dehydrogenase, ammonia, and NAD(P)H.

10. The method according to claim 1, wherein the cytochrome P450 monooxygenase of the CYP153 family has a peptide having the amino acid sequence of SEQ ID NO: 19 or a peptide having an amino sequence having 90% or more of homology to the amino acid sequence of SEQ ID NO: 19.

11. The method according to claim 10, wherein the fatty acid or the ester comprises methyl laurate.

12. The method according to claim 10,
wherein the fatty acid or the ester comprises methyl laurate, and
the electron donor is at least one of a ferredoxin reductase and a ferredoxin.

* * * * *

SEQUENCE LISTING

<160> NUMBER OF SEQ ID NOS: 68

<210> SEQ ID NO 1
<211> LENGTH: 230
<212> TYPE: PRT
<213> ORGANISM: Pseudomonas oleovorans

<400> SEQUENCE: 1

```
Met Ser Phe Ser Asn Tyr Lys Val Ile Ala Met Pro Val Leu Val Ala
1               5                   10                  15

Asn Phe Val Leu Gly Ala Ala Thr Ala Trp Ala Asn Glu Asn Tyr Pro
            20                  25                  30

Ala Lys Ser Ala Gly Tyr Asn Gln Gly Asp Trp Val Ala Ser Phe Asn
        35                  40                  45

Phe Ser Lys Val Tyr Val Gly Glu Glu Leu Gly Asp Leu Asn Val Gly
    50                  55                  60

Gly Gly Ala Leu Pro Asn Ala Asp Val Ser Ile Gly Asn Asp Thr Thr
65                  70                  75                  80

Leu Thr Phe Asp Ile Ala Tyr Phe Val Ser Ser Asn Ile Ala Val Asp
                85                  90                  95

Phe Phe Val Gly Val Pro Ala Arg Ala Lys Phe Gln Gly Glu Lys Ser
            100                 105                 110

Ile Ser Ser Leu Gly Arg Val Ser Glu Val Asp Tyr Gly Pro Ala Ile
        115                 120                 125

Leu Ser Leu Gln Tyr His Tyr Asp Ser Phe Glu Arg Leu Tyr Pro Tyr
    130                 135                 140

Val Gly Val Gly Val Gly Arg Val Leu Phe Phe Asp Lys Thr Asp Gly
145                 150                 155                 160

Ala Leu Ser Ser Phe Asp Ile Lys Asp Lys Trp Ala Pro Ala Phe Gln
                165                 170                 175

Val Gly Leu Arg Tyr Asp Leu Gly Asn Ser Trp Met Leu Asn Ser Asp
            180                 185                 190

Val Arg Tyr Ile Pro Phe Lys Thr Asp Val Thr Gly Thr Leu Gly Pro
        195                 200                 205

Val Pro Val Ser Thr Lys Ile Glu Val Asp Pro Phe Ile Leu Ser Leu
    210                 215                 220

Gly Ala Ser Tyr Val Phe
225                 230
```

<210> SEQ ID NO 2
<211> LENGTH: 693
<212> TYPE: DNA
<213> ORGANISM: Pseudomonas oleovorans

<400> SEQUENCE: 2

```
atgagttttt ctaattataa agtaatcgcg atgccggtgt tggttgctaa ttttgttttg      60
ggggcggcca ctgcatgggc gaatgaaaat tatccggcga atctgctgg ctataatcag     120
ggtgactggg tcgctagctt caattttct aaggtctatg tgggtgagga gcttggcgat    180
ctaaatgttg gagggggggc tttgccaaat gctgatgtaa gtattggtaa tgatacaaca    240
cttacgtttg atatcgccta ttttgttagc tcaaatatag cggtggattt ttttgttggg    300
gtgccagcta gggctaaatt tcaaggtgag aaatcaatct cctcgctggg aagagtcagt    360
gaagttgatt acggccctgc aattctttcg cttcaatatc attacgatag ctttgagcga    420
ctttatccat atgttggggt tggtgttggt cgggtgctat ttttgataa aaccgacggt     480
gctttgagtt cgtttgatat taaggataaa tgggcgcctg cttttcaggt tggccttaga    540
tatgaccttg gtaactcatg gatgctaaat tcagatgtgc gttatattcc tttcaaaacg    600
gacgtcacag gtactcttgg cccggttcct gtttctacta aaattgaggt tgatcctttc    660
attctcagtc ttggtgcgtc atatgttttc taa                                693
```

<210> SEQ ID NO 3
<211> LENGTH: 230
<212> TYPE: PRT
<213> ORGANISM: Pseudomonas putida

<400> SEQUENCE: 3

```
Met Asn Pro Pro Ile Leu Lys Lys Leu Ala Met Ser Ile Leu Ala Thr
  1               5                  10                  15

Ser Phe Val Leu Gly Gly Ala Ser Ala Trp Ser Gly Glu Ile Tyr Ser
                 20                  25                  30

Thr Glu Thr Ala Gly Tyr Asn Gln Gly Asp Trp Val Ala Ser Phe Asn
             35                  40                  45

Met Ser Lys Val Tyr Val Asp Glu Thr Leu Gly Ser Leu Asn Val Gly
         50                  55                  60

Gly Ala Thr Val Pro Asn Ala Ala Val Ser Ile Gly Asn Asp Thr Thr
 65                  70                  75                  80

Val Ser Phe Asp Ile Ser Tyr Phe Ile Ser Asn Asn Val Ala Leu Asp
                 85                  90                  95

Phe Phe Val Gly Ile Pro Ala Lys Ala Lys Phe Gln Gly Glu Lys Ser
            100                 105                 110

Ile Ser Ala Leu Gly Arg Val Ser Glu Val Asp Tyr Gly Pro Ala Ile
        115                 120                 125

Leu Ser Leu Gln Tyr His Phe Asp Asn Phe Glu Arg Leu Tyr Pro Tyr
    130                 135                 140

Val Gly Leu Gly Val Gly Arg Val Phe Phe Phe Asp Lys Thr Asp Gly
145                 150                 155                 160

Ala Leu Thr Ser Phe Asp Ile Lys Asp Lys Trp Ala Pro Ala Val Gln
                165                 170                 175

Val Gly Leu Arg Tyr Asp Phe Gly Asn Ser Trp Met Leu Asn Ser Asp
            180                 185                 190

Val Arg Tyr Ile Pro Phe Lys Thr Asp Val Ser Gly Thr Leu Gly Ala
        195                 200                 205

Ala Pro Val Ser Thr Lys Ile Glu Ile Asp Pro Phe Ile Leu Ser Leu
    210                 215                 220

Gly Ala Ser Tyr Lys Phe
225                 230
```

<210> SEQ ID NO 4
<211> LENGTH: 693
<212> TYPE: DNA
<213> ORGANISM: Pseudomonas putida

<400> SEQUENCE: 4

```
atgaatccgc ctattttaaa aaaactcgct atgtcgatat tagcaactag ttttgtgttg      60
ggtggggcca gtgcgtggtc aggtgaaatc tattcgactg aaactgctgg ctacaatcag     120
ggcgactggg ttgctagctt taatatgtct aaagtttatg tagacgagac gctaggctcc     180
ctaaatgtag gtggggctac tgtacccaat gctgctgtaa gcatcggtaa tgatacaaca     240
gtttcttttg atatttccta ttttattagt aacaatgtag ctttggattt tttcgtcggg     300
attccagcta agctaagtt tcaaggtgaa aaatccatct ctgcgctggg aagagtcagt     360
gaagttgatt atggccctgc aatttttgtca cttcagtatc attttgataa ttttgagcga     420
ctttatccat atgtcggact aggtgtcggt cgagtgtttt tcttcgacaa aactgatggt     480
gccttgactt catttgatat caaagataaa tgggcgcctg ctgttcaggt cggccttaga     540
tatgattttg gtaactcatg gatgttaaat tcagatgtgc gctatattcc tttcaaaaca     600
gatgtttctg gtacacttgg ggctgcacct gtttctacca agattgagat tgatcctttc     660
attctgagtc ttggagcatc atataagttc tga                                   693
```

<210> SEQ ID NO 5
<211> LENGTH: 246
<212> TYPE: PRT
<213> ORGANISM: Marinobacter aquaeolei VT8

<400> SEQUENCE: 5

```
Met Cys Tyr Glu Lys Leu Gln Phe Tyr Leu Lys Pro Ile Cys Phe Asn
1               5                  10                  15

Thr Lys Lys Asp Asn Lys Lys Met Lys Pro Lys Ile Ile Ser Lys Val
            20                  25                  30

Ser Leu Val Ala Phe Leu Leu Leu Ser Leu Ala Ala Ser Leu Ala Asn
        35                  40                  45

Ala Gln Ser Glu Pro Val Tyr Ser Arg Gly Asp Trp Val Val Gly Leu
    50                  55                  60

Asn Ala Thr Arg Val Leu Thr Asp Glu Asp Leu Arg Ser Ala Ser Ala
65                  70                  75                  80

Gly Gly Ala Pro Val Pro Asn Ser Asn Leu Ser Ile Asn Asn Asp Thr
                85                  90                  95

Thr Val Ser Phe Asp Val Ser Tyr Phe Leu Ser Asn Gln Leu Ala Phe
            100                 105                 110

Asn Ile Phe Gly Gly Ile Pro Ala Ser Ala Asp Leu Gln Gly Glu Glu
        115                 120                 125

Ser Leu Ser Gly Leu Phe Leu Gly Gln Thr Asp Tyr Gly Pro Val Ile
    130                 135                 140

Leu Ser Leu Gln Tyr His Val Leu Thr Gly Ser Asn Phe Ser Pro Tyr
145                 150                 155                 160

Phe Gly Ala Gly Val Gly Arg Ile Leu Phe Leu Asp Glu Lys Asp Arg
                165                 170                 175

Ala Leu Thr Asp Phe Asp Val Glu Asp Thr Trp Ala Pro Ala Ile Gln
            180                 185                 190

Ala Gly Phe Arg Trp Arg Ile His Asn Asn Trp Ser Ala Asn Phe Asp
        195                 200                 205
```

```
Val Arg Tyr Ala Pro Phe Lys Ala Asp Ile Thr Gly Asn Leu Gly Pro
    210                 215                 220

Ala Pro Val Gln Ala Glu Val Glu Val Asp Pro Thr Ile Val Ser Ile
225                 230                 235                 240

Gly Val Ala Tyr Arg Phe
                245

<210> SEQ ID NO 6
<211> LENGTH: 741
<212> TYPE: DNA
<213> ORGANISM: Marinobacter aquaeolei

<400> SEQUENCE: 6
ttgtgttacg aaaaattgca gttttaccta aagccaattt gttttaatac caaaaaggat     60
aataaaaaaa tgaaacctaa aataattagt aaagtctcgt tagtggcgtt ccttttactt    120
tcacttgctg cgagcctggc caacgctcaa tctgagccgg tttacagtag aggcgactgg    180
gtggttggac tgaatgccac tagagtttta accgatgaag atttgcgatc agcctctgcg    240
gggggtgccc ccgttccaaa ttccaacctg tctattaaca acgatacgac cgtttcattc    300
gacgtgtcgt attttctgag taatcagctg gcatttaaca ttttttggcgg cattcccgct    360 agtgcggacc tccagggcga agagtctctc tccggtcttt tcttggtca aacagattat    420 ggtccggtaa ttcttttcgct tcagtatcat gtcttaacgg gtagcaactt ctctccgtac    480
tttggagcgg gtgtaggacg gattctcttt ttagatgaga aggatcgcgc actaaccgac    540
ttcgacgtcg aagatacatg ggcccctgcg attcaggctg ttttcgctg gaggatacac    600 aataactggt cggcaaattt tgacgttaga tatgcaccct tcaaagcgga tatcaccggt    660
aacctaggcc cggcccctgt tcaggcagaa gtggaagtgg accccactat cgtgagcatc    720
ggtgtcgcat atcgctttta a                                               741

<210> SEQ ID NO 7
<211> LENGTH: 228
<212> TYPE: PRT
<213> ORGANISM: Oceanicaulis alexandrii HTCC2633

<400> SEQUENCE: 7

Met Lys Gln Ser Asn Val Lys Ser Lys Gly Pro Phe Ala Ser Lys Phe
1                   5                   10                  15

Val Leu Ile Thr Met Ile Gly Gly Phe Ser Ser Phe Ser Val Ala Asn
                20                  25                  30

Ala Glu Pro Leu Tyr Ser Lys Gly Asp Trp Leu Phe Gly Leu Asn Ala
            35                  40                  45

Ala Lys Val Phe Thr Asn Glu Thr Leu Asp Ser Ile Ser Ala Gly Gly
        50                  55                  60

Ala Pro Ile Pro Gly Ala Gly Val Asn Ile Thr Asp Asp Thr Thr Leu
65                  70                  75                  80

Ser Phe Asp Val Ser Tyr Phe Leu Asn Ser Val Ala Leu Asn Phe
                85                  90                  95

Phe Gly Gly Leu Pro Ala Ser Ala Asn Leu Ala Gly Ser Gly Ser Leu
            100                 105                 110

Ala Gly Leu Pro Val Gly Glu Thr Glu Tyr Gly Pro Ala Val Leu Ser
        115                 120                 125

Leu Gln Tyr His Phe Ser Thr Asn Ser Ser Val Ser Pro Tyr Val Gly
    130                 135                 140

Ala Gly Ile Ala Arg Ile Leu Phe Leu Glu Glu Gln Gly Asp Ala Leu
```

Ala Asp Phe Asp Leu Lys Asp Ala Trp Ala Pro Ala Val Gln Val Gly
            165                 170                 175

Met Arg Tyr Gln Met Ser Asp Asn Trp Phe Ala Asn Ala Asp Ile Arg
            180                 185                 190

Tyr Thr Pro Phe Glu Thr Asp Ile Ser Gly Thr Leu Gly Gly Ala Pro
            195                 200                 205

Val Arg Gly Lys Ile Ser Val Asp Pro Thr Ile Leu Asn Ile Gly Ile
        210                 215                 220

Ala Tyr Arg Phe
225

<210> SEQ ID NO 8
<211> LENGTH: 741
<212> TYPE: DNA
<213> ORGANISM: Oceanicaulis alexandrii HTCC2633

<400> SEQUENCE: 8
ttaaaagcga tatgcgacac cgatgctcac gatagtgggg tccacttcca cttctgcctg      60
aacaggggcc gggcctaggt taccggtgat atccgctttg aagggtgcat atctaacgtc     120
aaaatttgcc gaccagttat tgtgtatcct ccagcgaaaa ccagcctgaa tcgcagggc      180
ccatgtatct tcgacgtcga agtcggttag tgcgcgatcc ttctcatcta aaagagaat     240
ccgtcctaca cccgctccaa agtacggaga gaagttgcta cccgttaaga catgatactg     300
aagcgaaaga attaccggac cataatctgt ttgaccaaga aaagaccgg agagagactc     360
ttcgccctgg aggtccgcac tagcgggaat gccgccaaaa atgttaaatg ccagctgatt     420
actcagaaaa tacgacacgt cgaatgaaac ggtcgtatcg ttgttaatag acaggttgga     480
atttggaacg ggggcacccc ccgcagaggc tgatcgcaaa tcttcatcgg ttaaaactct     540
agtggcattc agtccaacca cccagtcgcc tctactgtaa accggctcag attgagcgtt     600
ggccaggctc gcagcaagtg aaagtaaaag gaacgccact aacgagactt tactaattat     660
tttaggttc atttttttat tatccttttt ggtattaaaa caaattggct ttaggtaaaa     720
ctgcaatttt tcgtaacaca a                                              741

<210> SEQ ID NO 9
<211> LENGTH: 223
<212> TYPE: PRT
<213> ORGANISM: Marinobacter manganoxydans MnI7-9

<400> SEQUENCE: 9

Met Lys Pro Lys Ile Ile Ser Lys Val Ser Leu Val Ala Phe Leu Leu
1               5                   10                  15

Leu Ser Leu Ala Ala Ser Leu Ala Asn Ala Gln Ser Glu Pro Val Tyr
            20                  25                  30

Ser Arg Gly Asp Trp Val Val Gly Leu Asn Ala Thr Arg Val Leu Thr
        35                  40                  45

Asp Glu Asp Leu Arg Ser Ala Ser Ala Gly Ser Ala Pro Val Pro Asn
    50                  55                  60

Ser Asn Leu Ser Ile Asn Asn Asp Thr Thr Val Ser Phe Asp Val Ser
65                  70                  75                  80

Tyr Phe Leu Ser Asn Gln Leu Ala Phe Asn Ile Phe Gly Gly Ile Pro
                85                  90                  95

Ala Ser Ala Asp Leu Gln Gly Glu Glu Ser Leu Ser Gly Leu Phe Leu
            100                 105                 110

Gly Gln Thr Asp Tyr Gly Pro Val Ile Leu Ser Leu Gln Tyr His Val
            115                 120                 125

Leu Thr Gly Ser Asn Phe Ser Pro Tyr Phe Gly Ala Gly Val Gly Arg
        130                 135                 140

Ile Leu Phe Leu Asp Glu Lys Asp Arg Ala Leu Thr Asp Phe Asp Val
145                 150                 155                 160

Glu Asp Thr Trp Ala Pro Ala Val Gln Ala Gly Phe Arg Trp Arg Ile
                165                 170                 175

His Asn Asn Trp Ser Ala Asn Phe Asp Val Arg Tyr Ala Pro Phe Glu
            180                 185                 190

Ala Asp Ile Thr Gly Asn Leu Gly Pro Ala Pro Val Gln Ala Lys Val
        195                 200                 205

Glu Val Asp Pro Thr Ile Val Ser Ile Gly Val Ala Tyr Arg Phe
210                 215                 220

<210> SEQ ID NO 10
<211> LENGTH: 687
<212> TYPE: DNA
<213> ORGANISM: Marinobacter manganoxydans MnI7-9

<400> SEQUENCE: 10
atgaaacaat ctaatgtaaa atccaagggg cctttgcct cgaagtttgt gttaatcacg      60
atgatcggtg cttttcgtc gttcagcgtc gcaaatgcgg aaccgcttta ctccaagggc    120
gactggcttt ttggcctgaa tgcggcgaaa gtattcacga acgaaacgtt ggattcaatc    180
agcgcgggcg gtgcgccaat acccggggct ggtgtcaata tcaccgatga caccacgctg    240
agtttcgacg tttcctattt tttgaattca tctgtagcgt tgaacttctt tggtggtttg    300
cctgccagcg ctaatcttgc agggagcggc agtttggcag gactgcctgt tggagagacg    360
gaatatggcc ctgctgtttt gtcgcttcaa tatcactttt cgactaattc atccgttagc    420
ccttatgttg gtgccggtat cgctcgaatc ttgtttctgg aagaacaagg ggatgcactc    480
gcggacttcg acttgaaaga cgcctgggcg cccgctgtcc aagttggaat gcgctatcaa    540
atgagcgata ttggtttgc caatgccgat atacgttaca cgccattcga aacagatatc    600
tctgggacac tcggcggggc gccagtcaga ggcaagattt cggtggaccc aacaattctc    660
aatatcggta ttgcctaccg gttttaa                                         687

<210> SEQ ID NO 11
<211> LENGTH: 227
<212> TYPE: PRT
<213> ORGANISM: Caulobacter sp. K31

<400> SEQUENCE: 11

Met Arg Lys Asn Gly Ala Tyr Met Tyr Ala Arg Leu Ala Gln Tyr Ala
1               5                   10                  15

Thr Ala Leu Ala Val Leu Ser Val Phe Pro Gln Ala Ala Leu Ala Gln
            20                  25                  30

Asn Ser Glu Gly Phe Lys Leu Trp Ala Val Ser Leu Asn Ala Thr Arg
        35                  40                  45

Val Phe Val Asp Glu Asp Ala Pro Asp Ile Thr Leu Ala Gly Gly Pro
    50                  55                  60

Val Pro Gly Ser Asn Val Arg Ile Gly Asp Ala Thr Ser Ala Thr Ile
65                  70                  75                  80

Asp Ile Gly Tyr Phe Phe Thr Pro Asn Val Ala Gly Asn Leu Phe Leu
                85                  90                  95

Gly Val Pro Ala Thr Ala Gln Ile Asp Gly Ala Gly Ser Leu Glu Pro
            100                 105                 110

Leu Gly Thr Leu Ala Lys Val Asn Tyr Gly Pro Ile Ile Leu Ser Ala
        115                 120                 125

Gln Tyr His Phe Asn Asn Leu Gly Lys Val His Pro Tyr Leu Gly Val
    130                 135                 140

Gly Val Gly Arg Ile Val Phe Leu Asn Glu Arg Asp Arg Ala Leu Leu
145                 150                 155                 160

Asn Phe Ser Ile Asp Asp Ser Trp Ala Pro Ala Ala Gln Val Gly Val
                165                 170                 175

Arg Tyr Glu Leu Gly Ala Glu Trp Met Leu Asn Ala Asp Val Arg Tyr
            180                 185                 190

Val Pro Phe Ser Thr His Ala Thr Gly Ser Leu Gly Gly Ala Pro Val
        195                 200                 205

Arg Thr Arg Leu Asp Ile Asp Pro Ile Leu Thr Ser Ala Gly Val Thr
    210                 215                 220

Tyr Arg Phe
225

<210> SEQ ID NO 12
<211> LENGTH: 684
<212> TYPE: DNA
<213> ORGANISM: Caulobacter sp. K31

<400> SEQUENCE: 12
atgagaaaaa atggagcata tatgtatgca aggcttgcgc aatacgccac cgcgctcgcc    60
gtcttgagcg tcttccccca ggctgcattg gcccagaatt cggaaggatt caagctgtgg   120
gccgtaagtc tgaatgcaac tagggtcttc gtggatgagg atgcgcccga catcaccttg   180
gctggagggc ctgttccggg ctcgaatgtg aggatcgggg atgccacgtc ggcgaccatt   240
gatatcggat atttcttcac gcccaatgtt gctggtaatt tgtttctcgg cgtgccggcg   300
accgcgcaaa ttgacggcgc tgggtcactt gagccgctcg gaactctagc caaggtcaac   360
tatggaccca tcatcttgtc ggcccagtac catttcaaca atcttggcaa ggttcatccc   420
tatctgggag tgggcgtcgg gcggatcgtc tttctgaatg agcgtgacag agctttgctt   480
aatttcagta tcgacgacag ttgggcgcct gcggctcagg tgggtgttcg gtacgagctt   540
ggcgcagaat ggatgctgaa cgctgacgtt cgatacgttc ccttctccac gcacgctacc   600
ggttcactgg gtggagcgcc tgtccggaca cgtttggaca tcgacccgat cctgacgagc   660
gccggagtga cttaccggtt ttag                                          684

<210> SEQ ID NO 13
<211> LENGTH: 410
<212> TYPE: PRT
<213> ORGANISM: Alcanivorax borkumensis SK2

<400> SEQUENCE: 13

Met Glu Asn Glu Lys Gln Asp Ala Thr Val Ile Val Gly Gly Gly His
1               5                   10                  15

Ala Ala Gly Ala Leu Met Thr Ala Leu Ile Gln Lys Lys Tyr Pro His
            20                  25                  30

Glu Val Val Leu Val Gly Glu Glu Pro Tyr Pro Pro Tyr Gln Arg Pro
        35                  40                  45

Pro Leu Ser Lys Thr Tyr Leu Ser Gly Glu Val Asn Glu Glu Ser Leu
    50                  55                  60

Tyr Leu Lys Pro Arg Ser Val Tyr Glu Gly Ala Gly His Gln Leu Arg
65                  70                  75                  80

Leu Gly Val Arg Val Glu Asn Ile Asp Arg Asp Asn Lys Thr Leu Thr
                85                  90                  95

Leu Ser Asp Gln Ser Thr Leu Lys Tyr Gly Arg Leu Ile Leu Ala Thr
            100                 105                 110

Gly Ser His Val Arg Arg Leu Asn Ala Pro Gly Ser Glu Leu Lys Gly
            115                 120                 125

Ile His Tyr Leu His Asp Ile Ala Asp Thr Asp Thr Leu Arg Asp Gln
130                 135                 140

Leu Ser Pro Gly Ala Arg Leu Val Ile Val Gly Gly Tyr Ile Gly
145                 150                 155                 160

Leu Glu Val Ala Ala Ser Ala Ser Lys Lys Gly Val Asn Val Thr Val
                165                 170                 175

Leu Glu Gly Ala Glu Arg Leu Met Gln Arg Val Thr Gly Val Glu Met
            180                 185                 190

Ser Ser Phe Leu Tyr Ala Lys His Ser Gly Ser Gly Val Asp Val Arg
        195                 200                 205

Leu Asn Thr Ala Val Thr Gly Phe Lys Ala Gly Asp Gln Gly Arg Val
210                 215                 220

Ala Gly Val Thr Leu Ala Asn Gly Glu Thr Val Asp Ala Asp Val Val
225                 230                 235                 240

Leu Val Ser Ile Gly Val Ile Pro Glu Thr Ala Leu Ala Glu Ala Ala
                245                 250                 255

Gly Leu Ser Cys Glu Asp Gly Ile Leu Val Asp Glu Tyr Val Arg Thr
            260                 265                 270

Ser Asp Pro Ser Ile Leu Ala Ile Gly Asp Cys Thr Arg His Arg Asn
        275                 280                 285

Leu Phe Phe Glu Lys Met Gln Arg Leu Glu Ser Val Ala Asn Ala Val
290                 295                 300

Asp Gln Ala Arg Thr Ala Ala Thr Leu Met Gly Glu Asp Lys Pro
305                 310                 315                 320

Tyr Asp Ser Ala Pro Trp Phe Trp Ser Asn Gln Tyr Asp Val Arg Leu
                325                 330                 335

Gln Met Val Gly Leu Ser Gln Asp His Asp Glu Arg Val Met Arg Gly
            340                 345                 350

Ser Thr Glu Asp Lys Ala Phe Ala Val Phe Tyr Leu Arg Glu Gly Cys
        355                 360                 365

Val Ile Ala Val Asp Ala Val Asn Met Pro Ile Ala Phe Met Val Gly
370                 375                 380

Lys Gln Leu Val Gln His Arg Lys Ser Ile Ser Ala Asp Val Leu Ser
385                 390                 395                 400

Asp Leu Asp Val Glu Leu Lys Ser Leu Ile
                405                 410

<210> SEQ ID NO 14
<211> LENGTH: 1233
<212> TYPE: DNA
<213> ORGANISM: Alcanivorax borkumensis SK2

<400> SEQUENCE: 14
atggaaaacg aaaacaaga tgccactgtc atcgttggag gcgggcacgc agcaggtgcg    60
ttgatgacag ccttgataca aagaaatat ccacacgagg tggttctggt gggcgaagag   120

```
ccttatccgc ctaccagcg cccgccttta tccaaaacgt atctgtcagg agaggttaac      180
gaggaatctc tctatttgaa accgcgctcg gtgtatgaag gtgcggggca tcagttgcga      240
cttggtgtgc gcgttgagaa cattgatcga gacaacaaaa cccttacatt gtcagatcag      300
agcacactga atatggccg actgattctt gccacaggtt cacacgttag gcgtcttaat       360
gcgcctggat ctgaattaaa aggcatccat tatctgcatg acattgctga tacggataca      420
ttgcgcgatc aactgtcacc aggtgcccgt ttggttattg tcggtggcgg ctacattggc      480
cttgaggttg cagccagtgc gagcaagaaa ggcgttaatg ttacggtgct ggaaggcgct      540
gagcgtctaa tgcagcgagt tacgggcgtt gagatgtctt cgttcctgta tgctaagcac      600
agtggttctg gcgtggacgt gcgtcttaat actgctgtca ccggcttcaa agctggagat      660
caggggcgag tggctggcgt aacgttagca aatggcgaaa cggttgacgc agatgttgtg      720
cttgtctcga ttggcgttat acccgaaacg gctttggctg aggctgccgg cctatcctgt      780
gaagacggta tcctggtgga cgaatatgtc cgcacttctg acccaagcat cctggcgata      840
ggtgattgca ctcgtcaccg aaaccttttc ttcgagaaaa tgcagaggct cgagtccgtt      900
gctaacgctg tcgatcaagc acgtactgcg gcagcgacct tgatgggaga ggataagccc      960
tacgatagcg ctccatggtt ttggtcgaat caatatgatg ttcgtttgca atggtgggg     1020
ctctcgcagg accatgatga acgagtcatg cgtggcagca cggaagacaa agcgtttgcg     1080
gtgttctatc tccgtgaggg ctgtgtgatt gccgttgatg cggtgaatat gcccattgcg     1140
tttatggttg gaaagcagtt ggttcagcac cgtaagagta ttagcgctga cgtgttgagt     1200
gatctggatg ttgaattaaa gtctttgatc tga                                  1233
```

<210> SEQ ID NO 15
<211> LENGTH: 106
<212> TYPE: PRT
<213> ORGANISM: Alcanivorax borkumensis SK2

<400> SEQUENCE: 15

```
Met Gly Lys Ile Thr Phe Ile Glu Asn Asp Lys Thr Glu His Val Thr
1               5                   10                  15
Glu Phe Glu Ala Gly Ile Thr Leu Met Gln Val Ala Leu Asp Asn Ala
            20                  25                  30
Val Pro Gly Ile Asp Gly Asp Cys Gly Gly Glu Cys Ala Cys Gly Thr
        35                  40                  45
Cys His Leu Ile Val Pro Glu Glu Trp Phe Asp Lys Thr Gly Pro Ile
    50                  55                  60
Asn Asp Ala Glu Glu Gln Met Leu Ser Met Thr Pro Glu Arg Ala Lys
65                  70                  75                  80
Thr Ser Arg Leu Gly Cys Gln Val Lys Ala Thr Glu Ala Met Asp Gly
                85                  90                  95
Met Thr Val Gln Leu Pro Glu Phe Gln Met
            100                 105
```

<210> SEQ ID NO 16
<211> LENGTH: 321
<212> TYPE: DNA
<213> ORGANISM: Alcanivorax borkumensis SK2

<400> SEQUENCE: 16

```
gtgggaaaaa tcacctttat tgagaatgat aaaactgaac atgtaacaga atttgaggca       60
ggtattactt tgatgcaagt tgccttagac aacgccgttc ccggtattga tggggattgc      120
```

```
ggcggggagt gtgcctgtgg tacctgtcac ctgattgttc cagaagaatg gttcgataaa    180
accgggccga ttaatgatgc tgaagaacaa atgttgtcca tgacacctga gcgtgcaaaa    240
acctctcggt tggggtgtca ggttaaggcc actgaggcaa tggacggaat gactgttcaa    300
ttgccagaat ttcaaatgta a                                              321

<210> SEQ ID NO 17
<211> LENGTH: 336
<212> TYPE: PRT
<213> ORGANISM: Escherichia coli

<400> SEQUENCE: 17

Met Lys Ala Ala Val Val Thr Lys Asp His His Val Asp Val Thr Tyr
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                85                  90                  95

Ser Gly Asn Glu Thr Leu Cys Arg Ser Val Lys Asn Ala Gly Tyr Ser
            100                 105                 110

Val Asp Gly Gly Met Ala Glu Glu Cys Ile Val Val Ala Asp Tyr Ala
        115                 120                 125

Val Lys Val Pro Asp Gly Leu Asp Ser Ala Ala Ala Ser Ser Ile Thr
    130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
        195                 200                 205

Leu Ala Ile Asn Ser His Thr Glu Asp Ala Ala Lys Ile Val Gln Glu
    210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335
```

<210> SEQ ID NO 18
<211> LENGTH: 1011
<212> TYPE: DNA
<213> ORGANISM: Escherichia coli

<400> SEQUENCE: 18

| | | | | | |
|---|---|---|---|---|---|
| atgaaggctg | cagttgttac | gaaggatcat | catgttgacg | ttacgtataa | aacactgcgc | 60 |
| tcactgaaac | atggcgaagc | cctgctgaaa | atggagtgtt | gtggtgtatg | tcataccgat | 120 |
| cttcatgtta | agaatggcga | ttttggtgac | aaaaccggcg | taattctggg | ccatgaaggc | 180 |
| atcggtgtgg | tggcagaagt | gggtccaggt | gtcacctcat | aaaaccagg | cgatcgtgcc | 240 |
| agcgtggcgt | ggttctacga | aggatgcggt | cattgcgaat | actgtaacag | tggtaacgaa | 300 |
| acgctctgcc | gttcagttaa | aaatgccgga | tacagcgttg | atggcgggat | ggcggaagag | 360 |
| tgcatcgtgg | tcgccgatta | cgcggtaaaa | gtgccagatg | gtctggactc | ggcggcggcc | 420 |
| agcagcatta | cctgtgcggg | agtcaccacc | tacaaagccg | ttaagctgtc | aaaaattcgt | 480 |
| ccagggcagt | ggattgctat | ctacggtctt | ggcggtctgg | gtaacctcgc | cctgcaatac | 540 |
| gcgaagaatg | tctttaacgc | caaagtgatc | gccattgatg | tcaatgatga | gcagttaaaa | 600 |
| ctggcaaccg | aaatgggcgc | agatttagcg | attaactcac | acaccgaaga | cgccgccaaa | 660 |
| attgtgcagg | agaaaactgg | tgcgctcac | gctgcggtgg | taacagcggt | agctaaagct | 720 |
| gcgtttaact | cggcagttga | tgctgtccgt | gcaggcggtc | gtgttgtggc | tgtcggtcta | 780 |
| ccgccggagt | ctatgagcct | ggatatccca | cgtcttgtgc | tggatggtat | tgaagtggtc | 840 |
| ggttcgctgg | tcggcacgcg | ccaggattta | actgaagcct | tccagtttgc | cgccgaaggt | 900 |
| aaagtggtgc | cgaaagtcgc | cctgcgtccg | ttagcggaca | tcaacaccat | ctttactgag | 960 |
| atggaagaag | gcaaaatccg | tggccgcatg | gtgattgatt | ccgtcacta | a | 1011 |

<210> SEQ ID NO 19
<211> LENGTH: 470
<212> TYPE: PRT
<213> ORGANISM: Alcanivorax borkumensis SK2

<400> SEQUENCE: 19

Met Ser Thr Ser Ser Thr Ser Asn Asp Ile Gln Ala Lys Ile Ile
1               5                   10                  15

Asn Ala Thr Ser Lys Val Val Pro Met His Leu Gln Ile Lys Ala Leu
                20                  25                  30

Lys Asn Leu Met Lys Val Lys Arg Lys Thr Ile Gly Thr Ser Arg Pro
            35                  40                  45

Gln Val His Phe Val Glu Thr Asp Leu Pro Asp Val Asn Asp Leu Ala
        50                  55                  60

Ile Glu Asp Ile Asp Thr Ser Asn Pro Phe Leu Tyr Arg Gln Gly Lys
65                  70                  75                  80

Ala Asn Ala Tyr Phe Lys Arg Leu Arg Asp Glu Ala Pro Val His Tyr
                85                  90                  95

Gln Lys Asn Ser Ala Phe Gly Pro Phe Trp Ser Val Thr Arg Tyr Glu
            100                 105                 110

Asp Ile Val Phe Val Asp Lys Ser His Asp Leu Phe Ser Ala Glu Pro
        115                 120                 125

Gln Ile Ile Leu Gly Asp Pro Pro Glu Gly Leu Ser Val Glu Met Phe
    130                 135                 140

Ile Ala Met Asp Pro Pro Lys His Asp Val Gln Arg Arg Ala Val Gln
145                 150                 155                 160

Gly Val Val Ala Pro Lys Asn Leu Lys Glu Met Glu Gly Leu Ile Arg
            165                 170                 175

Lys Arg Thr Gly Asp Val Leu Asp Ser Leu Pro Leu Asp Thr Pro Phe
            180                 185                 190

Asn Trp Val Pro Val Ser Lys Glu Leu Thr Gly Arg Met Leu Ala
            195                 200                 205

Ser Leu Leu Asp Phe Pro Tyr Asp Glu Arg Glu Lys Leu Val Gly Trp
        210                 215                 220

Ser Asp Arg Leu Ser Gly Ala Ser Ser Ala Thr Gly Gly Glu Phe Thr
225                 230                 235                 240

Asn Glu Asp Val Phe Phe Asp Ala Ala Asp Met Ala Trp Ala Phe
            245                 250                 255

Ser Lys Leu Trp Arg Asp Lys Glu Ala Arg Gln Lys Ala Gly Glu Glu
            260                 265                 270

Pro Gly Phe Asp Leu Ile Ser Met Leu Gln Ser Asn Glu Asp Thr Lys
            275                 280                 285

Asp Leu Ile Asn Arg Pro Leu Glu Phe Ile Gly Asn Leu Ala Leu Leu
            290                 295                 300

Ile Val Gly Gly Asn Asp Thr Thr Arg Asn Ser Met Ser Gly Gly Val
305                 310                 315                 320

Leu Ala Leu Asn Gln Phe Pro Glu Gln Phe Glu Lys Leu Lys Ala Asn
            325                 330                 335

Pro Lys Leu Ile Pro Asn Met Val Ser Glu Ile Ile Arg Trp Gln Thr
            340                 345                 350

Pro Leu Ala Tyr Met Arg Arg Val Ala Lys Gln Asp Val Glu Leu Asn
            355                 360                 365

Gly Gln Thr Ile Lys Lys Gly Asp Arg Val Leu Met Trp Tyr Ala Ser
        370                 375                 380

Gly Asn Gln Asp Glu Arg Lys Phe Glu Asn Pro Glu Gln Phe Ile Ile
385                 390                 395                 400

Asp Arg Lys Asp Thr Arg Asn His Val Ser Phe Gly Tyr Gly Val His
            405                 410                 415

Arg Cys Met Gly Asn Arg Leu Ala Glu Leu Gln Leu Arg Ile Leu Trp
            420                 425                 430

Glu Glu Leu Leu Pro Arg Phe Glu Asn Ile Glu Val Ile Gly Glu Pro
            435                 440                 445

Glu Arg Val Gln Ser Asn Phe Val Arg Gly Tyr Ser Lys Met Met Val
        450                 455                 460

Lys Leu Thr Ala Lys Lys
465                 470

<210> SEQ ID NO 20
<211> LENGTH: 1413
<212> TYPE: DNA
<213> ORGANISM: Alcanivorax borkumensis SK2

<400> SEQUENCE: 20
atgtcaacga gttcaagtac aagtaatgac atccaggcaa aataattaa cgccacatcc      60 aaagtcgtgc caatgcatct acagatcaag gcactaaaaa acttgatgaa ggtgaagcgg     120
aagaccattg cacttcccg ccctcaggtg cactttgttg aaaccgattt gcctgacgtc      180
aatgatttgg cgatagaaga tatcgatacg agtaacccct tttataccg acaaggtaag      240 gcgaatgcgt actttaagcg gttgcgtgat gaagcgccgg tgcactatca aagaacagt      300

```
gctttcgggc cgttctggtc ggtaacacgc tacgaagata tcgtcttcgt ggacaagagc    360
catgatttgt tttccgccga accccaaatt atcttgggtg atcctccgga aggcctgtcg    420
gttgaaatgt tcatcgctat ggatcctccc aagcacgacg tacagcgtcg ggcagtccag    480
ggtgttgttg cgcccaagaa cctgaaagaa atggaaggac tgatccgcaa gcgcaccggg    540
gacgtactgg atagcctgcc gttggacact ccgttcaact gggtgccggt ggtgtcgaaa    600
gagctgaccg gcgcatgct agcctcactg ttagatttcc cgtatgacga acgcgaaaaa    660
ctggttggct ggtcggatcg attgtccggc gcgtcctcgg caaccggcgg cgagtttacg    720
aatgaagatg tgttttttga tgacgcggca gatatggcgt gggctttctc caagctttgg    780
cgtgataaag aagcccgtca aaagcaggt gaagagccgg gtttcgattt gatcagcatg    840
cttcagtcca atgaagacac aaaagatctg atcaatcgtc ctttggaatt cattggtaat    900
ctcgcgttgt tgattgttgg cggtaatgac accacgcgta actcaatgag cgggggggtg    960
ctggctttaa atcagttccc agagcaattc gagaagctaa aggcgaaccc aaagcttatc   1020
cccaatatgg tctctgaaat cattcgctgg caaacgccgc ttgcgtatat cgccgggtt   1080 gccaagcagg atgtggagct gaacggacag accatcaaga agggtgatcg cgtgctgatg   1140
tggtatgcgt cgggcaacca ggatgagaga aaatttgaga tcctgagca attcatcatc    1200 gaccgcaaag atacgcgtaa ccatgtgtcg tttggttatg gggttcaccg ttgtatgggc   1260
aaccgccttg ccgaactgca gctgcgtatt ctgtgggaag agcttctccc tcgctttgaa   1320
aacatcgaag tgatcggtga gccggagcgc gtgcaatcga ctttgtgcg gggctattcc    1380 aagatgatgg ttaagttgac ggctaaaaaa taa                                1413
```

<210> SEQ ID NO 21
<211> LENGTH: 12
<212> TYPE: PRT
<213> ORGANISM: Artificial Sequence
<220> FEATURE:
<223> OTHER INFORMATION: Synthetic sequence motif from CYP153
<220> FEATURE:
<221> NAME/KEY: MOD_RES
<222> LOCATION: (3)..(3)
<223> OTHER INFORMATION: Ile or Leu
<220> FEATURE:
<221> NAME/KEY: MOD_RES
<222> LOCATION: (4)..(4)
<223> OTHER INFORMATION: Ile or Val

<400> SEQUENCE: 21

Leu Leu Xaa Xaa Gly Gly Asn Asp Thr Thr Arg Asn
1               5                   10

<210> SEQ ID NO 22
<211> LENGTH: 378
<212> TYPE: PRT
<213> ORGANISM: Bacillus subtilis subsp. subtilis str. 168

<400> SEQUENCE: 22

Met Ile Ile Gly Val Pro Lys Glu Ile Lys Asn Asn Glu Asn Arg Val
1               5                   10                  15

Ala Leu Thr Pro Gly Gly Val Ser Gln Leu Ile Ser Asn Gly His Arg
            20                  25                  30

Val Leu Val Glu Thr Gly Ala Gly Leu Gly Ser Gly Phe Glu Asn Glu
        35                  40                  45

Ala Tyr Glu Ser Ala Gly Ala Glu Ile Ile Ala Asp Pro Lys Gln Val
    50                  55                  60

Trp Asp Ala Glu Met Val Met Lys Val Lys Glu Pro Leu Pro Glu
 65                  70                  75                  80

Tyr Val Tyr Phe Arg Lys Gly Leu Val Leu Phe Thr Tyr Leu His Leu
                 85                  90                  95

Ala Ala Glu Pro Glu Leu Ala Gln Ala Leu Lys Asp Lys Gly Val Thr
            100                 105                 110

Ala Ile Ala Tyr Glu Thr Val Ser Glu Gly Arg Thr Leu Pro Leu Leu
        115                 120                 125

Thr Pro Met Ser Glu Val Ala Gly Arg Met Ala Ala Gln Ile Gly Ala
    130                 135                 140

Gln Phe Leu Glu Lys Pro Lys Gly Gly Lys Gly Ile Leu Leu Ala Gly
145                 150                 155                 160

Val Pro Gly Val Ser Arg Gly Lys Val Thr Ile Ile Gly Gly Gly Val
                165                 170                 175

Val Gly Thr Asn Ala Ala Lys Met Ala Val Gly Leu Gly Ala Asp Val
            180                 185                 190

Thr Ile Ile Asp Leu Asn Ala Asp Arg Leu Arg Gln Leu Asp Asp Ile
        195                 200                 205

Phe Gly His Gln Ile Lys Thr Leu Ile Ser Asn Pro Val Asn Ile Ala
    210                 215                 220

Asp Ala Val Ala Glu Ala Asp Leu Leu Ile Cys Ala Val Leu Ile Pro
225                 230                 235                 240

Gly Ala Lys Ala Pro Thr Leu Val Thr Glu Glu Met Val Lys Gln Met
                245                 250                 255

Lys Pro Gly Ser Val Ile Val Asp Val Ala Ile Asp Gln Gly Gly Ile
            260                 265                 270

Val Glu Thr Val Asp His Ile Thr Thr His Asp Gln Pro Thr Tyr Glu
        275                 280                 285

Lys His Gly Val Val His Tyr Ala Val Ala Asn Met Pro Gly Ala Val
    290                 295                 300

Pro Arg Thr Ser Thr Ile Ala Leu Thr Asn Val Thr Val Pro Tyr Ala
305                 310                 315                 320

Leu Gln Ile Ala Asn Lys Gly Ala Val Lys Ala Leu Ala Asp Asn Thr
                325                 330                 335

Ala Leu Arg Ala Gly Leu Asn Thr Ala Asn Gly His Val Thr Tyr Glu
            340                 345                 350

Ala Val Ala Arg Asp Leu Gly Tyr Glu Tyr Val Pro Ala Glu Lys Ala
        355                 360                 365

Leu Gln Asp Glu Ser Ser Val Ala Gly Ala
    370                 375

<210> SEQ ID NO 23
<211> LENGTH: 1137
<212> TYPE: DNA
<213> ORGANISM: Bacillus subtilis subsp. subtilis str. 168

<400> SEQUENCE: 23
atgatcatcg gcgtccctaa agaaatcaaa acaacgaaa accgcgtggc actgaccccg      60
ggtggtgtgt cccaattgat cagcaacggc accgtgtct tggtcgaaac cggcgctggt      120
ctgggtagcg gctttgagaa cgaggcatac gagtcggcag gtgcggagat tattgccgat      180
cctaagcagg tgtgggacgc cgagatggtt atgaaagtga agaaccgct gccggaagaa      240 tacgtttact ttcgcaaagg tctggttctg ttcacctatc tgcacttggc cgctgagccg      300
gagctggcac aagcgctgaa ggataagggc gttacggcga tcgcgtatga aacggtgtct      360

```
gagggccgta ccctgccgct gctgaccccg atgagcgagg ttgccggtcg tatggcagcc    420
cagatcggtg cgcagttcct ggagaaaccg aaaggtggca agggcattct gctggcgggt    480
gtcccgggtg tttctcgtgg taaggtcact atcattggcg gtggcgtggt cggtaccaac    540
gcggcgaaga tggcggttgg cctgggtgct gacgttacga ttatcgactt gaacgctgat    600
cgcctgcgtc aattggacga catctttggc caccagatca agaccttgat ctccaatccg    660
gtgaatatcg cggacgcggt ggcggaggcg gatctgctga tttgcgcagt tctgattcct    720
ggcgcgaagg cgccgaccct ggtcacggaa gaaatggtga acaaatgaa accgggtagc     780 gtgattgttg acgtagcgat tgatcagggt ggtatcgtgg aaactgttga ccacatcacg    840
actcatgatc agccgacgta cgagaaacat ggtgttgttc actatgcagt tgcaaatatg    900
ccgggtgcgg tcccgcgtac tagcacgatt gccctgacca atgtgaccgt tccgtatgca    960
ctgcaaattg caaataaggg tgcggtgaag gctttggcgg acaacaccgc gctgcgtgct    1020
ggtctgaata ccgcgaacgg tcatgtgacc tatgaggcgg tcgacgtgaa cctgggttat    1080
gagtacgtgc tgcagagaa ggcactgcag gacgagagct ccgtggcagg tgcgtaa       1137
```

<210> SEQ ID NO 24
<211> LENGTH: 459
<212> TYPE: PRT
<213> ORGANISM: Chromobacterium violaceum ATCC 12472

<400> SEQUENCE: 24

```
Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240
```

| | | | | | | | | | | | |
|---|---|---|---|---|---|---|---|---|---|---|---|
|Tyr|Trp|Pro|Glu|Ile|Glu|Arg|Ile|Cys|Arg|Lys|Tyr Asp Val Leu Leu|
| | | |245| | |250| | | |255| |

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
            290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
            325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
            405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 25
<211> LENGTH: 1380
<212> TYPE: DNA
<213> ORGANISM: Chromobacterium violaceum ATCC 12472

<400> SEQUENCE: 25

```
atgcagaaac agcgtaccac ctctcagtgg cgtgaactgg atcgcggcgca tcatctgcat     60
ccgtttaccg ataccgcgag cctgaatcag gcgggtgcgc gtgtgatgac ccgtggcgaa    120
ggcgtgtatc tgtgggatag cgaaggcaac aaaattattg atggcatggc gggcctgtgg    180
tgcgtgaacg tgggctatgg ccgtaaagat tttgcggaag cggcgcgtcg tcagatggaa    240
gaactgccgt ttataaacac cttctttaaa ccacccatc cggcggtggt ggaactgagc    300
agcctgctgg ccgaagttac cccggcaggt tttgatcgtg tgttttatac caacagcggc    360
agcgaaagcg tggataccat gattcgtatg gtgcgtcgtt attgggatgt gcagggcaaa    420
ccggaaaaaa aaaccctgat ggccgttgg aacggctatc acggcagcac cattggcggt    480
gcgagcctgg gcggcatgaa atatatgcat gaacagggcg atctgccgat tccgggcatg    540
gcgcatattg aacagccgtg gtggtataaa catggcaaag atatgacccc ggatgaattt    600
ggcgtggttg cggcgcgttg gctggaagaa aaaattctgg aaatcggcgc ggataaagtg    660
gcggcgtttg tgggcgaacc gattcagggt gcgggcggtg tgattgttcc gccggcaacc    720
tattggccgg aaattgaacg tatttgccgc aaatatgatg tgctgctggt tgcggatgaa    780
gtgatttgcg gctttggccg taccggcgaa tggtttggcc atcagcattt tggctttcag    840
```

-continued

```
ccggacctgt ttaccgcggc gaaaggcctg agcagcggct atctgccgat ggcgcggtg      900
tttgtgggca aacgtgttgc ggaaggtctg attgcgggcg gtgattttaa ccatggcttt      960
acctatagcg gccatccggt gtgtgcggcg gtggcgcatg cgaatgttgc ggcgctgcgt     1020
gatgaaggca ttgtgcagcg tgtgaaagat gatattggcc gtatatgca gaaacgttgg     1080
cgtgaaacct ttagccgttt tgaacatgtg gatgatgtgc gtggcgtggg catggtgcag     1140
gcgtttaccc tggtgaaaaa caaagcgaaa cgtgaactgt tccggatttt ggcgaaatt      1200
ggcaccctgt gccgcgatat tttttttcgc aacaacctga ttatgcgtgc gtgcggcgat     1260
cacattgtgt ctgcaccgcc gctggttatg acccgtgcgg aagtggatga atgctggcc      1320
gtggcggaac gttgcctgga agaatttgaa cagaccctga agcgcgtggg cctggcctaa     1380
```

<210> SEQ ID NO 26
<211> LENGTH: 552
<212> TYPE: PRT
<213> ORGANISM: Pseudomonas oleovorans

<400> SEQUENCE: 26

```
Met Tyr Asp Tyr Ile Ile Val Gly Ala Gly Ser Ala Gly Cys Val Leu
1               5                   10                  15

Ala Asn Arg Leu Ser Ala Asp Pro Ser Lys Arg Val Cys Leu Leu Glu
            20                  25                  30

Ala Gly Pro Arg Asp Thr Asn Pro Leu Ile His Met Pro Leu Gly Ile
        35                  40                  45

Ala Leu Leu Ser Asn Ser Lys Lys Leu Asn Trp Ala Phe Gln Thr Ala
    50                  55                  60

Pro Gln Gln Asn Leu Asn Gly Arg Ser Leu Phe Trp Pro Arg Gly Lys
65                  70                  75                  80

Thr Leu Gly Gly Ser Ser Ile Asn Ala Met Val Tyr Ile Arg Gly
                85                  90                  95

His Glu Asp Asp Tyr His Ala Trp Glu Gln Ala Ala Gly Arg Tyr Trp
            100                 105                 110

Gly Trp Tyr Arg Ala Leu Glu Leu Phe Lys Arg Leu Glu Cys Asn Gln
        115                 120                 125

Arg Phe Asp Lys Ser Glu His His Gly Val Asp Gly Glu Leu Ala Val
    130                 135                 140

Ser Asp Leu Lys Tyr Ile Asn Pro Leu Ser Lys Ala Phe Val Gln Ala
145                 150                 155                 160

Gly Met Glu Ala Asn Ile Asn Phe Asn Gly Asp Phe Asn Gly Glu Tyr
                165                 170                 175

Gln Asp Gly Val Gly Phe Tyr Gln Val Thr Gln Lys Asn Gly Gln Arg
            180                 185                 190

Trp Ser Ser Ala Arg Ala Phe Leu His Gly Val Leu Ser Arg Pro Asn
        195                 200                 205

Leu Asp Ile Ile Thr Asp Ala His Ala Ser Lys Ile Leu Phe Glu Asp
    210                 215                 220

Arg Lys Ala Val Gly Val Ser Tyr Ile Lys Lys Asn Met His His Gln
225                 230                 235                 240

Val Lys Thr Thr Ser Gly Gly Glu Val Leu Ser Leu Gly Ala Val
                245                 250                 255

Gly Thr Pro His Leu Leu Met Leu Ser Gly Val Gly Ala Ala Ala Glu
            260                 265                 270

Leu Lys Glu His Gly Val Ser Leu Val His Asp Leu Pro Glu Val Gly
        275                 280                 285
```

```
Lys Asn Leu Gln Asp His Leu Asp Ile Thr Leu Met Cys Ala Ala Asn
            290                 295                 300

Ser Arg Glu Pro Ile Gly Val Ala Leu Ser Phe Ile Pro Arg Gly Val
305                 310                 315                 320

Ser Gly Leu Phe Ser Tyr Val Phe Lys Arg Glu Gly Phe Leu Thr Ser
                325                 330                 335

Asn Val Ala Glu Ser Gly Gly Phe Val Lys Ser Ser Pro Asp Arg Asp
            340                 345                 350

Arg Pro Asn Leu Gln Phe His Phe Leu Pro Thr Tyr Leu Lys Asp His
        355                 360                 365

Gly Arg Lys Ile Ala Gly Gly Tyr Gly Tyr Thr Leu His Ile Cys Asp
    370                 375                 380

Leu Leu Pro Lys Ser Arg Gly Arg Ile Gly Leu Lys Ser Ala Asn Pro
385                 390                 395                 400

Leu Gln Pro Pro Leu Ile Asp Pro Asn Tyr Leu Ser Asp His Glu Asp
                405                 410                 415

Ile Lys Thr Met Ile Ala Gly Ile Lys Ile Gly Arg Ala Ile Leu Gln
            420                 425                 430

Ala Pro Ser Met Ala Lys His Phe Lys His Glu Val Val Pro Gly Gln
        435                 440                 445

Ala Val Lys Thr Asp Asp Glu Ile Ile Glu Asp Ile Arg Arg Arg Ala
    450                 455                 460

Glu Thr Ile Tyr His Pro Val Gly Thr Cys Arg Met Gly Lys Asp Pro
465                 470                 475                 480

Ala Ser Val Val Asp Pro Cys Leu Lys Ile Arg Gly Leu Ala Asn Ile
                485                 490                 495

Arg Val Val Asp Ala Ser Ile Met Pro His Leu Val Ala Gly Asn Thr
            500                 505                 510

Asn Ala Pro Thr Ile Met Ile Ala Glu Asn Ala Ala Glu Ile Ile Met
        515                 520                 525

Arg Asn Leu Asp Val Glu Ala Leu Glu Ala Ser Ala Glu Phe Ala Arg
    530                 535                 540

Glu Gly Ala Glu Leu Glu Leu Ala
545                 550

<210> SEQ ID NO 27
<211> LENGTH: 1656
<212> TYPE: DNA
<213> ORGANISM: Pseudomonas oleovorans

<400> SEQUENCE: 27
atgtacgact atataatcgt tggtgctgga tctgcaggat gtgtgcttgc taatcgtctt      60
tcggccgacc cctctaaaag agtttgttta cttgaagctg ggccgcgaga tacgaatccg     120
ctaattcata tgccgttagg tattgctttg ctttcaaata gtaaaaagtt gaattgggct     180
tttcaaactg cgccacagca aaatctcaac ggccggagcc ttttctggcc acaggaaaa      240 acgttaggtg gttcaagctc aatcaacgca atggtctata tccgagggca tgaagacgat     300
taccacgcat gggagcaggc ggccggccgc tactgggggtt ggtaccgggc tcttgagttg     360
ttcaaaaggc ttgaatgcaa ccagcgattc gataagtccg agcaccatgg ggttgacgga     420
gaattagctg ttagtgattt aaaatatatc aatccgctta gcaaagcatt cgtgcaagcc     480
ggcatggagg ccaatattaa tttcaacgga gatttcaacg cgagtaccag gacggcgta      540 gggttctatc aagtaaccca aaaaaatgga caacgctgga gctcggcgcg tgcattcttg     600
```

```
cacggtgtac tttccagacc aaatctagac atcattactg atgcgcatgc atcaaaaatt    660 cttttttgaag accgtaaggc ggttggtgtt tcttatataa agaaaaatat gcaccatcaa    720
gtcaagacaa cgagtggtgg tgaagtactt cttagtcttg gcgcagtcgg cacgcctcac    780
cttctaatgc tttctggtgt tggggctgca gccgagctta aggaacatgg tgtttctcta    840
gtccatgatc ttcctgaggt ggggaaaaat cttcaagatc atttggacat cacattgatg    900
tgcgcagcaa attcgagaga gccgataggt gttgctcttt cttttcatccc tcgtggtgtc    960 tcgggtttgt tttcatatgt gtttaagcgc gagggggttc tcactagtaa cgtggcagag   1020
tcgggtggtt ttgtaaaaag ttctcctgat cgtgatcggc ccaatttgca gtttcatttc   1080
cttccaactt atcttaaaga tcacggtcga aaaatagcgg gtggttatgg ttatacgcta   1140
catatatgtg atcttttgcc taagagccga ggcagaattg gcctaaaaag cgccaatcca   1200
ttacagccgc ctttaattga cccgaactat cttagcgatc atgaagatat taaaaccatg   1260
attgcgggta ttaagatagg gcgcgctatt ttgcaggccc catcgatggc gaagcatttt   1320
aagcatgaag tagtaccggg ccaggctgtt aaaactgatg atgaaataat cgaagatatt   1380
cgtaggcgag ctgagactat ataccatccg gtaggtactt gtaggatggg taaagatcca   1440
gcgtcagttg ttgatccgtg cctgaagatc cgtgggttgg caaatattag agtcgttgat   1500
gcgtcaatta tgccgcactt ggtcgcgggt aacacaaacg ctccaactat tatgattgca   1560
gaaaatgcgg cagaaataat tatgcggaat cttgatgtgg aagcattaga ggctagcgct   1620
gagtttgctc gcgagggtgc agagctagag ttggcc                              1656

<210> SEQ ID NO 28
<211> LENGTH: 535
<212> TYPE: PRT
<213> ORGANISM: Alcanivorax borkumensis str. SK2

<400> SEQUENCE: 28

Met Tyr Asp Tyr Ile Ile Val Gly Ala Gly Ser Ala Gly Cys Val Leu
1               5                   10                  15

Ala Asn Arg Leu Ser Ala Asp Thr Ser Lys Arg Val Ala Leu Ile Glu
            20                  25                  30

Ala Gly Pro Arg Asp Lys Asn Pro Leu Ile His Met Pro Ile Gly Ile
        35                  40                  45

Ala Leu Leu Ala Asn Asn Arg Lys Leu Asn Trp Ala Leu Glu Thr Glu
    50                  55                  60

Pro Gln Glu His Leu Lys Gly Arg Gln Leu Phe Trp Pro Arg Gly Lys
65                  70                  75                  80

Thr Leu Gly Gly Ser Ser Ile Asn Ala Met Val Tyr Ile Arg Gly
                85                  90                  95

His Lys Ala Asp Tyr Asp His Trp Gly Gln Val Ala Gly Asn Asn Asn
            100                 105                 110

Leu Trp Gly Trp Asp Arg Ala Leu Thr Leu Phe Arg Arg Val Glu Asp
        115                 120                 125

Asn Gln Arg Leu Gly Ala Asp Pro Tyr His Gly Lys Asp Gly Glu Leu
    130                 135                 140

Thr Val Ser Glu Leu Lys Ser Ile Asn Pro Leu Ser Arg Asp Phe Val
145                 150                 155                 160

Arg Ala Ala Pro His Val Asp Leu Pro Val Asn Thr Asp Phe Asn Gly
                165                 170                 175

Lys Ser Gln Asp Gly Leu Gly Leu Tyr Gln Val Thr Gln Lys Asn Gly
```

180                 185                 190
Gln Arg Trp Ser Ser Ala Gln Ala Phe Leu Arg Ala Ala Glu Ser Arg
            195                 200                 205

Ser Asn Leu Asp Val Leu Thr Asp Ala Arg Val Thr Arg Val Ala Met
        210                 215                 220

Glu Gly Lys Arg Ala Val Gly Val Thr Leu Lys Gln Gly Ser Glu Tyr
225                 230                 235                 240

Arg Gln Leu Arg Leu Asn Ala Gly Gly Glu Val Ile Leu Ser Gly Gly
                245                 250                 255

Ala Val Asn Ser Pro Gln Leu Leu Leu Ser Gly Ile Gly Asp Ser
            260                 265                 270

Lys Glu Leu Ala Lys His Gly Ile Pro Leu Val His His Leu Pro Glu
        275                 280                 285

Val Gly Gln Asn Leu Ala Asp His Leu Asp Ile Thr Ile Met His Thr
    290                 295                 300

Ala Asn Ser Arg Leu Pro Ile Gly Val Ala Pro Ser Phe Leu Phe Arg
305                 310                 315                 320

Gly Val Ser Ala Leu Phe Ser Tyr Ile Phe Ala Arg Arg Gly Phe Leu
                325                 330                 335

Thr Ser Asn Val Ala Glu Ser Gly Gly Phe Val Lys Ser Asp Pro Ser
            340                 345                 350

Ser Glu Arg Pro Asn Val Gln Phe His Phe Leu Pro Thr Tyr Leu Lys
        355                 360                 365

Asp His Gly Arg Lys Val Met Ala Gly Tyr Gly Tyr Thr Leu His Ile
    370                 375                 380

Cys Asp Leu Leu Pro Lys Ser Arg Gly Phe Ile Gly Leu Gln Ser Pro
385                 390                 395                 400

Asp Pro Leu Ala Asn Pro Leu Ile Gln Pro Asn Tyr Leu Ser Asp Pro
                405                 410                 415

Glu Asp Ile Lys Thr Met Ile Ser Ala Ile Lys Phe Gly Arg Arg Ile
            420                 425                 430

Leu Gly Ala Pro Thr Met Ala Leu His Ser Lys Arg Glu Val Met Pro
        435                 440                 445

Gly Glu Ser Val Ser Thr Asp Ala Gln Leu Ala Asp Phe Ile Arg Glu
    450                 455                 460

Asn Ala Glu Thr Ile Tyr His Pro Val Gly Thr Cys Arg Met Gly Ala
465                 470                 475                 480

Asp Pro Asp Ser Val Val Asp Pro Glu Leu Lys Val Arg Gly Val Glu
                485                 490                 495

Gly Leu Arg Val Val Asp Ala Ser Ile Met Pro Ser Leu Val Ala Gly
            500                 505                 510

Asn Thr Asn Ala Pro Thr Met Met Ile Ala Glu Asn Ala Ala Asp Ile
        515                 520                 525

Leu Leu Gly Lys Val Gln Val
    530                 535

<210> SEQ ID NO 29
<211> LENGTH: 1608
<212> TYPE: DNA
<213> ORGANISM: Alcanivorax borkumensis str. SK2

<400> SEQUENCE: 29
atgtacgatt acattattgt aggagccggg tcggctggct gtgtgttggc taaccgcctt     60
agtgcggata cttcaaaacg cgtagcgctg atcgaagccg gcccacggga taaaaatccc    120

```
ctaattcaca tgcctattgg catcgctctc ctcgccaaca atagaaaact caactgggcg    180
ctagaaaccg agcctcaaga acacttgaaa gggcgccaac tgttttggcc ccgcggaaag    240
acgcttggtg gctcttcttc tattaatgcc atggtgtata tcaggggcca taaagccgac    300
tacgatcatt ggggccaagt tgccggtaac aacaacctct ggggttggga tcgtgcatta    360
acattatttc gtcgggtgga agacaaccaa cgccttggcg cagacccata ccacggcaaa    420
gatggtgagc tcactgtaag cgaattaaaa tcgatcaacc cgctgagccg tgattttgtt    480
cgagcagcgc ctcacgtaga cctgcccgtg aacacagact taacggcaa atcacaagac     540
ggattggggc tttaccaagt aacgcagaaa atggccagc gctggagttc agcgcaagca     600
ttttgcgtg ccgctgagag ccgctctaat cttgacgtgc taaccgatgc tcgagtaacc     660
cgcgtggcta tggagggtaa gcgagcggtt ggcgtgaccc tgaaacaggg aagtgaatat    720
cgccagctga gactcaatgc cggcggcgaa gtcatcctgt ctggtggtgc agttaattca    780
ccacagctcc tcctgctgtc tggcatcggg gatagtaaag agcttgcgaa cacggcatt     840
ccgctagttc atcaccttcc cgaagtcggc cagaatttgg ccgatcatct ggacatcacg    900
atcatgcaca cggcgaactc tcgtttgccc attggcgttg cacccagctt cttattccgt    960
ggggtgagcg cacttttctc ctatatcttt gcgcgacgtg gttttcttac cagtaatgtt   1020
gccgagtctg gcggctttgt gaaatcggac ccttcgtctg agcgacccaa tgtgcaattt   1080
cactttttgc ccacttacct gaaggatcat ggccgaaaag taatggcagg ctatggctac   1140
actttgcaca tttgcgattt gttgccgaaa agccgaggct tcattggatt gcaaagccct   1200
gacccattgg ccaatccgct gattcagcct aactatctga gcgaccccga agatatcaaa   1260
acaatgatat ccgccattaa gtttgggcga cgcattctcg gagcaccaac aatggcgctt   1320
catagtaaac gggaagttat gccgggagag tccgtatcta cggacgctca actagcagac   1380
tttatccgtg aaaatgctga aaccatctac caccctgttg gcacttgtcg tatgggggcc   1440
gaccctgatt ccgttgtcga tccggaactg aaagtcagag gcgttgaagg gctaagagtt   1500
gtcgatgcct cgataatgcc cagcttggtg gcgggtaaca cgaacgcacc cacaatgatg   1560
attgccgaaa atgcggccga catcctgctg ggaaaggtcc aagtgtaa                1608
```

<210> SEQ ID NO 30
<211> LENGTH: 416
<212> TYPE: PRT
<213> ORGANISM: Marinobacter aquaeolei VT8

<400> SEQUENCE: 30

```
Met Val Ser Lys Arg Lys Glu Arg Thr Val Ile Val Gly Gly Gly His
1               5                   10                  15

Ala Ala Gly Ala Leu Leu Thr Ala Leu Leu Gln Lys Lys Tyr Gln His
                20                  25                  30

Glu Val Val Leu Val Gly Asn Glu Pro His Pro Tyr His Arg Pro
            35                  40                  45

Pro Leu Ser Lys Asn Tyr Leu Thr Gly Asp Val Asp Gln Glu Ser Leu
        50                  55                  60

Tyr Leu Lys Pro Arg Ser Val Tyr Glu Asn Ala Gly His Gln Leu Arg
65                  70                  75                  80

Leu Gly Val Arg Val Glu Gln Ile Asp Arg Asp Ser Ser Thr Ile Ser
                85                  90                  95

Leu Ser Asp Gln Ser Arg Leu Gln Tyr Asp Arg Leu Val Leu Ala Thr
            100                 105                 110
```

Gly Ser His Leu Arg His Leu Asn Ala Pro Gly Ala Asp Leu Asn Gly
        115                 120                 125

Ile His Tyr Leu His Asp Ile Ala Asp Ser Glu Val Leu Arg Glu Gln
        130                 135                 140

Leu Val Ala Gly Lys Arg Leu Val Val Gly Gly Tyr Ile Gly
145                 150                 155                 160

Leu Glu Val Ala Ala Ser Ala Asn Lys Lys Gly Val Asn Val Thr Val
                165                 170                 175

Leu Glu Ala Ala Glu Arg Leu Met Gln Arg Val Thr Gly Pro Glu Ile
                180                 185                 190

Ser Ala Phe Leu Tyr Asp Lys His Arg Gly Ala Gly Val Asp Val Arg
        195                 200                 205

Leu Asn Thr Ala Val Thr Gly Phe Glu Ala Gly Asp Gln Gly His Val
        210                 215                 220

Ala Gly Val Thr Leu Ala Asp Gly Ser Thr Val Pro Ala Asp Ile Val
225                 230                 235                 240

Leu Val Ser Ile Gly Ile Ile Pro Glu Thr Ala Leu Ala Lys Asp Ala
                245                 250                 255

Gly Leu Pro Cys Asp Asn Gly Ile Ile Val Asp Glu Phe Thr Arg Thr
        260                 265                 270

Glu Asp Pro Ala Ile Leu Ala Ile Gly Asp Cys Thr Arg His Arg Asn
        275                 280                 285

Leu Phe Phe Glu Lys Met Gln Arg Leu Glu Ser Val Ala Asn Ala Val
        290                 295                 300

Asp Gln Ala Arg Thr Ala Ala Thr Leu Met Gly Glu Glu Lys Pro
305                 310                 315                 320

Tyr Asp Ser Val Pro Trp Phe Trp Ser Asn Gln Tyr Asp Val Arg Leu
                325                 330                 335

Gln Met Val Gly Leu Ser Gln Asn His Asp Gln Arg Val Val Arg Gly
        340                 345                 350

Thr Pro Glu Asp Lys Gly Phe Ala Val Phe Tyr Leu Arg Glu Gly Cys
        355                 360                 365

Val Ile Ala Val Asp Ala Val Asn Leu Pro Leu Ala Phe Leu Val Gly
        370                 375                 380

Lys Thr Leu Val Gln Gln Arg Arg Thr Ile Asn Pro Glu Leu Ile Glu
385                 390                 395                 400

Asp Pro Asp Thr Glu Leu Lys Ser Leu Val Asn Gly Arg Leu Gln Ser
                405                 410                 415

<210> SEQ ID NO 31
<211> LENGTH: 1251
<212> TYPE: DNA
<213> ORGANISM: Marinobacter aquaeolei VT8

<400> SEQUENCE: 31
atggtaagca aacgtaaaga gaggacggtc attgttggcg gtgggcacgc agcaggtgcc     60
ctcctgacag ccttactcca aaaaaaatat caacatgagg tcgttctggt ggggaatgaa    120
cctcatccgc cctaccatcg accgccgctg tccaagaatt acctgacagg agacgttgat    180
caggagtcgc tgtacctgaa accgcgctcg gtatacgaga acgcaggcca tcagttgcgg    240
ctcggtgtgc gcgtcgaaca aattgatcgg gacagtagca ccatcagctt gtcggatcag    300
agcaggctgc aatacgatcg actggtcctg gccaccgggt cacaccttcg acacctgaac    360
gcgcccgggg ctgacttaaa tggcattcat tacctgcacg acatagctga ttcagaggta    420

```
ctgcgtgaac agttagttgc tggaaagcgc ctggtcgtcg tgggtggtgg ttacatcggc    480
cttgaggtgg cggccagtgc aacaaaaaa ggtgttaatg tcacggtgct agaagccgcc    540
gaacgtctta tgcagcgcgt tacgggcccg gaaatatcag cgttccttta cgacaaacac    600
cgtggcgccg cgtggacgt acgtctgaac acagcggtaa ccggcttcga agcgggcgat    660
caggggcatg tggctggcgt gacgttggcg gacggaagca ccgtaccggc cgacatcgtc    720
cttgtgtcga tcggcattat cccggaaacc gctctggcta aggacgccgg cctgccctgt    780
gataacggta ttattgttga cgaatttacc cgtaccgagg accccgccat cttggcgatc    840
ggtgactgca cccggcaccg gaatcttttc ttcgagaaga tgcaacgact cgagtctgtc    900
gccaatgctg tcgatcaggc tcgtacagcc gcggcaaccc tgatgggtga ggagaaaccc    960
tatgatagcg ttccatggtt ctggtcaaac cagtacgatg ttcgtctgca gatggtagga   1020
ttgtcgcaaa atcatgatca gcgagtggtt cgaggcaccc ccgaggataa aggatttgcc   1080
gtgttctatc tccgcgaagg ctgtgttatt gctgttgacg cggtcaacct gccccttgct   1140
tttttggtag gcaagacact cgttcaacaa cgcagaacga tcaacccgga actaatagag   1200
gatccggata ctgaactgaa atctttggtg aacggaaggc tccagagttg a            1251
```

<210> SEQ ID NO 32
<211> LENGTH: 404
<212> TYPE: PRT
<213> ORGANISM: Acinetobacter sp. OC4

<400> SEQUENCE: 32

```
Met Gln Thr Ile Val Ile Ile Gly Ala Ser His Ala Ala Gln Leu
1               5                   10                  15

Ala Ala Ser Leu Arg Pro Asp Gly Trp Gln Gly Glu Ile Val Val Ile
            20                  25                  30

Gly Asp Glu Pro Tyr Leu Pro Tyr His Arg Pro Leu Ser Lys Thr
            35                  40                  45

Phe Leu Arg Gly Ala Gln Leu Val Asp Glu Leu Leu Ile Arg Pro Ala
50                  55                  60

Ala Phe Tyr Gln Lys Asn Gln Ile Glu Phe Arg His Gly Arg Val Val
65                  70                  75                  80

Ala Ile Asp Arg Ala Ala Arg Ser Val Thr Leu Gln Asp Gly Ser Thr
                85                  90                  95

Leu Ala Tyr Asp Gln Leu Ala Leu Cys Thr Gly Ala Arg Val Arg Thr
            100                 105                 110

Val Ser Leu Ala Gly Ser Asp Leu Ala Gly Val His Tyr Leu Arg Asn
            115                 120                 125

Ile Ser Asp Val Gln Ala Ile Gln Pro Phe Val Gln Pro Asn Gly Lys
130                 135                 140

Ala Val Val Ile Gly Gly Gly Tyr Ile Gly Leu Glu Thr Ala Ala Ala
145                 150                 155                 160

Leu Thr Glu Gln Gly Met Gln Val Val Leu Glu Ala Ala Glu Arg
                165                 170                 175

Ile Leu Gln Arg Val Thr Ala Pro Glu Val Ser Asp Phe Tyr Thr Arg
            180                 185                 190

Ile His Arg Glu Gln Gly Val Thr Ile His Thr Gly Val Ser Val Thr
            195                 200                 205

Ala Ile Thr Gly Glu Gly Arg Ala Gln Ala Val Leu Cys Ala Asp Gly
210                 215                 220
```

```
Ser Met Phe Asp Ala Asp Leu Val Ile Ile Gly Val Gly Val Val Pro
225                 230                 235                 240

Asn Ile Glu Leu Ala Leu Asp Ala Gly Leu Gln Val Asp Asn Gly Ile
            245                 250                 255

Val Ile Asp Glu Tyr Cys Arg Thr Ser Ala Pro Glu Ile Val Ala Ile
        260                 265                 270

Gly Asp Cys Ala Asn Ala Phe Asn Pro Ile Tyr Gln Arg Arg Met Arg
    275                 280                 285

Leu Glu Ser Val Pro Asn Ala Asn Glu Gln Ala Lys Ile Ala Ser Ala
290                 295                 300

Thr Leu Cys Gly Leu Gln Arg Thr Ser Lys Ser Leu Pro Trp Phe Trp
305                 310                 315                 320

Ser Asp Gln Tyr Asp Leu Lys Leu Gln Ile Ala Gly Leu Ser Gln Gly
                325                 330                 335

Tyr Asp Gln Ile Val Ile Arg Gly Asp Val Gln Arg Arg Ser Phe
            340                 345                 350

Ala Ala Phe Tyr Leu Gln Ala Gly Arg Leu Ile Ala Ala Asp Cys Val
        355                 360                 365

Asn Arg Pro Gln Glu Phe Met Leu Ser Lys Lys Leu Ile Thr Ala Gly
370                 375                 380

Thr Ala Val Asp Pro Leu Arg Leu Ala Asp Glu Ser Ile Ala Val Gln
385                 390                 395                 400

Ala Leu Met Gly

<210> SEQ ID NO 33
<211> LENGTH: 1215
<212> TYPE: DNA
<213> ORGANISM: Acinetobacter sp. OC4

<400> SEQUENCE: 33
atgcagacca tcgtaatcat cggcgccagc cacgcagcag cccaactggc cgcgagcttg      60
cgtccggatg gttggcaggg tgagatcgtt gtcatcggtg atgaaccgta tctgccatac     120
caccgtccgc cgctgagcaa aaccttcctg cgtggtgcac aactggttga tgaactgctg     180
attcgtcctg ccgctttta ccaaaagaac cagattgagt tccgtcacgg tcgtgtggtc     240
gcaattgatc gtgcagcgcg tagcgttacc ctgcaagacg gtagcaccct ggcttatgat     300
cagctggcac tgtgcactgg tgcacgtgtg cgtaccgtta gcttggctgg cagcgacctg     360
gctggtgttc actacctgcg caacattagc gatgtccaag caatccagcc gttcgtgcaa     420
ccgaatggta aagcggttgt gattggtggc ggctacatcg tctggaaac ggctgcggcc     480
ctgacggaac aaggcatgca ggtggttgtt ttggaggcgg ctgagcgcat cctgcaacgc     540
gttacggcgc tgaagttag cgacttttac acccgtattc accgtgaaca gggcgttacc     600
attcacacgg tgtctcggt gacggccatt accggcgaag gtcgtgcgca ggcggtgctg     660
tgcgcggatg gtagcatgtt tgatgctgat ttggttatca ttggtgtcgg cgtcgtcccg     720
aatatcgagc tggctctgga tgcgggtctg caggtggata atggcatcgt catcgacgag     780
tactgtcgca cctctgcgcc ggagatcgtc gccattggtg actgcgcgaa tgctttcaac     840
ccgatctacc agcgtcgtat gcgcttggaa tcggtgccga cgcgaacga acaagcaaag     900
attgcaagcg caaccctgtg cggtctgcag cgtaccagca atccctgcc gtggttttgg     960
agcgatcaat atgatctgaa actgcaaatt gctggcctga gccaaggtta tgaccaaatt    1020
gtgattcgtg gcgacgttca acaacgccgc agcttcgcgg cgttctacct gcaggcgggt    1080
```

-continued

```
cgtctgatcg cggcagattg tgtaaatcgt ccgcaggagt ttatgctgag caagaagctg    1140
attaccgctg gtacggcggt ggacccgctg cgtctggctg acgagagcat cgctgtacag    1200
gcgctgatgg gctga                                                     1215
```

<210> SEQ ID NO 34
<211> LENGTH: 470
<212> TYPE: PRT
<213> ORGANISM: Marinobacter aquaeolei VT8

<400> SEQUENCE: 34

```
Met Pro Thr Leu Pro Arg Thr Phe Asp Asp Ile Gln Ser Arg Leu Ile
1               5                   10                  15

Asn Ala Thr Ser Arg Val Val Pro Met Gln Arg Gln Ile Gln Gly Leu
            20                  25                  30

Lys Phe Leu Met Ser Ala Lys Arg Lys Thr Phe Gly Pro Arg Arg Pro
        35                  40                  45

Met Pro Glu Phe Val Glu Thr Pro Ile Pro Asp Val Asn Thr Leu Ala
    50                  55                  60

Leu Glu Asp Ile Asp Val Ser Asn Pro Phe Leu Tyr Arg Gln Gly Gln
65                  70                  75                  80

Trp Arg Ala Tyr Phe Lys Arg Leu Arg Asp Glu Ala Pro Val His Tyr
                85                  90                  95

Gln Lys Asn Ser Pro Phe Gly Pro Phe Trp Ser Val Thr Arg Phe Glu
            100                 105                 110

Asp Ile Leu Phe Val Asp Lys Ser His Asp Leu Phe Ser Ala Glu Pro
        115                 120                 125

Gln Ile Ile Leu Gly Asp Pro Pro Glu Gly Leu Ser Val Glu Met Phe
    130                 135                 140

Ile Ala Met Asp Pro Pro Lys His Asp Val Gln Arg Ser Ser Val Gln
145                 150                 155                 160

Gly Val Val Ala Pro Lys Asn Leu Lys Glu Met Glu Gly Leu Ile Arg
                165                 170                 175

Ser Arg Thr Gly Asp Val Leu Asp Ser Leu Pro Thr Asp Lys Pro Phe
            180                 185                 190

Asn Trp Val Pro Ala Val Ser Lys Glu Leu Thr Gly Arg Met Leu Ala
        195                 200                 205

Thr Leu Leu Asp Phe Pro Tyr Glu Glu Arg His Lys Leu Val Glu Trp
    210                 215                 220

Ser Asp Arg Met Ala Gly Ala Ala Ser Ala Thr Gly Gly Glu Phe Ala
225                 230                 235                 240

Asp Glu Asn Ala Met Phe Asp Asp Ala Ala Asp Met Ala Arg Ser Phe
                245                 250                 255

Ser Arg Leu Trp Arg Asp Lys Glu Arg Arg Ala Ala Gly Glu Glu
            260                 265                 270

Pro Gly Phe Asp Leu Ile Ser Leu Leu Gln Ser Asn Lys Glu Thr Lys
        275                 280                 285

Asp Leu Ile Asn Arg Pro Met Glu Phe Ile Gly Asn Leu Thr Leu Leu
    290                 295                 300

Ile Val Gly Gly Asn Asp Thr Thr Arg Asn Ser Met Ser Gly Gly Leu
305                 310                 315                 320

Val Ala Met Asn Glu Phe Pro Arg Glu Phe Glu Lys Leu Lys Ala Lys
                325                 330                 335

Pro Glu Leu Ile Pro Asn Met Val Ser Glu Ile Ile Arg Trp Gln Thr
            340                 345                 350
```

```
Pro Leu Ala Tyr Met Arg Arg Ile Ala Lys Gln Asp Val Glu Leu Gly
        355                 360                 365

Gly Gln Thr Ile Lys Lys Gly Asp Arg Val Val Met Trp Tyr Ala Ser
    370                 375                 380

Gly Asn Arg Asp Glu Arg Lys Phe Asp Asn Pro Asp Gln Phe Ile Ile
385                 390                 395                 400

Asp Arg Lys Asp Ala Arg Asn His Met Ser Phe Gly Tyr Gly Val His
                405                 410                 415

Arg Cys Met Gly Asn Arg Leu Ala Glu Leu Gln Leu Arg Ile Leu Trp
            420                 425                 430

Glu Glu Ile Leu Lys Arg Phe Asp Asn Ile Glu Val Val Glu Glu Pro
        435                 440                 445

Glu Arg Val Gln Ser Asn Phe Val Arg Gly Tyr Ser Arg Leu Met Val
    450                 455                 460

Lys Leu Thr Pro Asn Ser
465                 470

<210> SEQ ID NO 35
<211> LENGTH: 1413
<212> TYPE: DNA
<213> ORGANISM: Marinobacter aquaeolei VT8

<400> SEQUENCE: 35
atgccaacac tgcccagaac atttgacgac attcagtccc gactgattaa cgccacctcc      60
agggtggtgc cgatgcagag gcaaattcag ggactgaaat tcttaatgag cgccaagagg     120
aagaccttcg gcccacgccg accgatgccc gaattcgttg aaacacccat cccggacgtt     180
aacacgctgg cccttgagga catcgatgtc agcaatccgt ttttataccg gcagggtcag     240
tggcgcgcct atttcaaacg gttgcgtgat gaggcgccgg tccattacca gaagaacagc     300
cctttcggcc cctctggtc ggtaactcgg tttgaagaca tcctgttcgt ggataagagt      360
cacgacctgt tttccgccga ccgcaaatc attctcggtg accctccgga ggggctgtcg      420
gtggaaatgt tcatagcgat ggatccgccg aaacacgatg tgcagcgcag ctcggtgcag     480
ggagtagtgg caccgaaaaa cctgaaggag atggaggggc tgatccgatc acgcaccggc     540
gatgtgcttg acagcctgcc tacagacaaa ccctttaact gggtacctgc tgtttccaag     600
gaactcacag gccgcatgct ggcgacgctt ctggattttc cttacgagga acgccacaag     660
ctggttgagt ggtcggacag aatggcaggt gcagcatcgg ccaccggcgg ggagtttgcc     720
gatgaaaatg ccatgtttga cgacgcggca gacatggccc ggtctttctc caggctttgg     780
cgggacaagg aggcgcgccg cgcagcaggc gaggagcccg gtttcgattt gatcagcctg     840
ttgcagagca caaagaaac gaaagacctg atcaatcggc cgatggagtt atccggtaat      900
ttgacgctgc tcatagtcgg cggcaacgat acgacgcgca actcgatgag tggtggcctg     960
gtggccatga cgaattccc caggaatt gaaaaattga aggcaaaacc ggagttgatt       1020
ccgaacatgg tgtcggaaat catccgctgg caaacgccgc tggcctatat gccgaatc      1080 gccaagcagg atgtcgaact gggcggccag accatcaaga agggtgatcg agttgtcatg     1140
tggtacgcgt cgggtaaccg ggacgagcgc aaatttgaca ccccgatca gttcatcatt     1200 gatcgcaagg acgcacgaaa ccacatgtcg ttcggctatg ggttcaccg ttgcatgggc    1260 aaccgtctgg ctgaactgca actgcgcatc tctgggaag aaatactcaa gcgttttgac     1320
aacatcgaag tcgtcgaaga gcccgagcgg gtgcagtcca acttcgtgcg gggctattcc    1380
```
aggttgatgg tcaaactgac accgaacagt taa                            1413

<210> SEQ ID NO 36
<211> LENGTH: 106
<212> TYPE: PRT
<213> ORGANISM: Acinetobacter sp. OC4

<400> SEQUENCE: 36

Met Gly Gln Ile Thr Phe Ile Ala His Asp Gly Ala Gln Thr Ser Val
1               5                   10                  15

Ala Ile Glu Ala Gly Lys Ser Leu Met Gln Leu Ala Val Glu Asn Gly
            20                  25                  30

Val Ala Gly Ile Asp Gly Asp Cys Gly Gly Glu Cys Ala Cys Gly Thr
        35                  40                  45

Cys His Val Ile Val Ser Ala Glu Trp Ser Asp Val Ala Gly Thr Ala
    50                  55                  60

Gln Ala Asn Glu Gln Gln Met Leu Glu Met Thr Pro Glu Arg Ala Ala
65                  70                  75                  80

Thr Ser Arg Leu Ala Cys Cys Ile Gln Val Thr Asp Ala Met Asp Gly
                85                  90                  95

Met Thr Val His Leu Pro Glu Phe Gln Met
            100                 105

<210> SEQ ID NO 37
<211> LENGTH: 321
<212> TYPE: DNA
<213> ORGANISM: Acinetobacter sp. OC4

<400> SEQUENCE: 37
atgggccaaa ttactttcat cgcacacgac ggcgcacaga cgagcgttgc gatcgaggcg     60
ggtaagtctt tgatgcagct ggcggtagaa aacggtgtcg ccggcatcga tggcgactgc    120
ggtggcgagt gtgcgtgtgg cacctgtcat gtcattgtct ctgcggagtg gagcgatgtg    180
gccggtaccg cgcaagccaa tgagcagcag atgctggaga tgactccgga gcgtgcggcc    240
accagccgtc tggcatgttg catccaagtg acggacgcga tggatggtat gaccgtccat    300
ctgccggaat tcagatgta a                                              321

<210> SEQ ID NO 38
<211> LENGTH: 542
<212> TYPE: PRT
<213> ORGANISM: Caulobacter sp. K31

<400> SEQUENCE: 38

Met Phe Asp Tyr Ile Ile Val Gly Ala Gly Ser Ala Gly Cys Leu Leu
1               5                   10                  15

Ala Glu Arg Leu Ser Ala Asn Pro Arg Thr Arg Val Cys Leu Leu Glu
            20                  25                  30

Ala Gly Pro Pro Asp Arg Ser Pro Leu Ile His Met Pro Ile Gly Ile
        35                  40                  45

Ala Leu Leu Ser Lys Ser Lys Ile Leu Asn Trp Ala Phe Glu Thr Gln
    50                  55                  60

Pro Gln Ala Asn Leu Asp Gly Arg Arg Leu Phe Trp Pro Arg Gly Lys
65                  70                  75                  80

Thr Leu Gly Gly Ser Ser Ser Ile Asn Ala Met Val Tyr Ile Arg Gly
                85                  90                  95

His Arg Asp Asp Tyr Asp Ser Trp Gly Glu Ala Ala Asp Pro Ile Trp
            100                 105                 110

```
Ser Tyr Asp Asn Val Leu Pro Leu Phe Lys Ala Met Glu Ser Asn Glu
            115                 120                 125

Arg Phe Gly Thr Asp Ala Phe His Gly Gly Asp Gly Glu Leu His Val
130                 135                 140

Ser Asp Leu Arg Thr Arg Asn Pro Leu Ser Asp Ala Phe Val Glu Ala
145                 150                 155                 160

Gly Gln Gln Ala Gln Phe Pro His Ala Val Asp Phe Asn Gly Lys Met
                165                 170                 175

Gln Asp Gly Val Gly Leu Tyr Gln Val Thr Gln His Lys Gly Arg Arg
            180                 185                 190

Trp Ser Ser Ala Arg Ala Phe Leu Ser Lys Ala Lys Gly Arg Pro Asn
            195                 200                 205

Leu Arg Ile Val Thr Gly Ala Arg Ala Thr Arg Ile Ile Leu Glu Gly
            210                 215                 220

Arg Lys Ala Val Gly Val Thr Tyr Ala Ala Gly Gly Lys Leu Val Asp
225                 230                 235                 240

Val Arg Thr Arg Gly Gly Glu Val Ile Leu Ser Gly Gly Ala Val Asn
                245                 250                 255

Ser Pro Gln Leu Leu Leu Ser Gly Ile Gly Gly Ala Ala Glu Leu
                260                 265                 270

Asn Ala Leu Gly Ile Pro Val Val Asp Leu Pro Ala Val Gly Lys
            275                 280                 285

Asn Leu Gln Asp His Leu Asp Ile Thr Ile Met His Glu Ala Asn Asp
            290                 295                 300

Arg Thr Pro Ile Gly Ile Ala Pro Ser Phe Ile Pro Arg Ala Leu Ser
305                 310                 315                 320

Gly Ala Leu Ser Tyr Ala Phe Leu Arg Lys Gly Phe Leu Thr Ser Asn
                325                 330                 335

Val Ala Glu Ala Gly Gly Phe Val Lys Ser Thr Pro Ser Arg Ser Arg
                340                 345                 350

Pro Asn Leu Gln Phe His Phe Leu Pro Thr Leu Leu Lys Asp His Gly
            355                 360                 365

Arg Glu Met Ala Phe Gly Tyr Gly Tyr Thr Leu His Val Cys Asp Leu
370                 375                 380

Leu Pro Lys Ser Arg Gly Arg Ile Gly Leu Thr Ser Pro Asp Pro Leu
385                 390                 395                 400

Asp Asp Pro Leu Ile Asp Pro Asn Tyr Leu Ser Ala Pro Glu Asp Ile
                405                 410                 415

Glu Thr Met Val Ala Ala Val Lys Ile Gly Arg Gln Ile Leu Ser Ala
                420                 425                 430

Pro Ser Met Ala Ala Phe Ser Lys Thr Glu Leu Val Pro Gly Pro Ser
            435                 440                 445

Val Gln Ser Lys Ala Asp Ile Met Ala Asp Ile Arg Arg Arg Ala Glu
            450                 455                 460

Thr Ile Tyr His Pro Val Gly Thr Cys Arg Met Gly Arg Asp Pro Gln
465                 470                 475                 480

Ser Val Val Asp Pro Ser Leu Arg Val Arg Gly Val Gln Gly Leu Arg
                485                 490                 495

Val Val Asp Ala Ser Val Met Pro Thr Leu Val Ala Gly Asn Thr Asn
            500                 505                 510

Ala Pro Thr Met Met Ile Ala Glu Arg Ala Ala Glu Leu Ile Leu Gly
            515                 520                 525
```

Lys Thr Lys Leu Ala Leu Ser Ala Asn Ile Glu Ala Phe Arg
        530                 535                 540

<210> SEQ ID NO 39
<211> LENGTH: 1629
<212> TYPE: DNA
<213> ORGANISM: Caulobacter sp. K31

<400> SEQUENCE: 39

| | |
|---|---|
| atgtttgact atattattgt tggagcgggg tctgccggat gcttgttggc ggagcgcttg | 60 |
| tcagccaatc ccaggacgcg ggtctgtctg cttgaggcgg gcccgcccga ccgcagcccg | 120 |
| ctgatccaca tgcccattgg gatagcgctt ctgtcaaaga gcaaaattct caattgggca | 180 |
| ttcgagacgc agccacaggc caatctcgat ggtcgacggc tgttttggcc gcgcggcaaa | 240 |
| acccttggcg gatcgagttc gatcaatgcg atggtctata tccgcgggca ccgggatgac | 300 |
| tatgactcct ggggcgaggc agccgatccg atctggtcct atgacaatgt gctcccgctg | 360 |
| ttcaaggcga tggagtccaa cgagagattt ggaaccgacg cgtttcatgg cggcgatggt | 420 |
| gagcttcacg tcagcgacct gcgaacccgc aaccccttga gcgatgcctt cgtcgaggcc | 480 |
| ggacaacagg cccagtttcc gcatgccgtc gatttcaatg gaagatgca ggacggcgtc | 540 |
| ggcctgtacc aggtcaccca gcacaaaggc cggcgctgga gttccgcgcg cgcctttctt | 600 |
| tccaaggcca aggccggcc caatctacgg atagtcacgg gcgcgcgggc tacccggatc | 660 |
| attctggagg gccgcaaagc ggtcggcgtg acctatgccg caggcggcaa gctggtcgat | 720 |
| gtgcgaacca ggggcggcga ggtcattctt tcgggcggcg ccgtcaattc cccgcaactg | 780 |
| ctgctgctttt ccggcatcgg cggcgcggcc gagctgaacg cactcggcat tccggtggtc | 840 |
| gtcgaccttc cggcagttgg aaaaaatctg caggatcacc tcgatatcac aatcatgcat | 900 |
| gaggcgaacg atcgtacacc gatcggcatc gcaccgtcat tcatcccgcg ggcgctgtcc | 960 |
| ggagcgctat cctacgcctt ccttcgaaag ggtttcttga cgagcaacgt cgccgaggcg | 1020 |
| ggcggcttcg tcaaaagcac accttcgcgg agtcggccga atctacagtt tcatttcctc | 1080 |
| cccacgcttt tgaaggacca tgggcgcgaa atgcgcttcg ggtatggcta tacattgcat | 1140 |
| gtctgcgatc ttctgcccaa gagccgaggc cgcatcgggc tcacaagccc cgaccgctc | 1200 |
| gacgatccgc tgatcgatcc aaactatctc tcggcccccg aagacattga ccatggtc | 1260 |
| gcggcggtga agatcggccg gcaaattctg tcggcgccgt caatggcggc cttctcgaaa | 1320 |
| accgaactgg tccctgggcc atcggtccag agcaaggcgg atatcatggc ggatatccgt | 1380 |
| cggcgagcgg agacgatcta tcatccggtg ggaacatgcc ggatgggacg agaccctcag | 1440 |
| tcggttgtcg atccgtcact ccgagtgcgt ggcgtgcaag gccttcgcgt cgtcgacgcc | 1500 |
| tcggtcatgc cgacgctggt cgccggaaac accaacgccc cgacgatgat gattgcgaa | 1560 |
| agagctgccg agctcattct tgggaagacg aaactcgcac tcagcgccaa cattgaggca | 1620 |
| ttccgctaa | 1629 |

<210> SEQ ID NO 40
<211> LENGTH: 704
<212> TYPE: PRT
<213> ORGANISM: Candida tropicalis

<400> SEQUENCE: 40

Met Ala Pro Phe Leu Pro Asp Gln Val Asp Tyr Lys His Val Asp Thr
1               5                   10                  15

Leu Met Leu Leu Cys Asp Gly Ile Ile His Glu Thr Thr Val Asp Glu

```
                     20                  25                  30
      Ile Lys Asp Val Ile Ala Pro Asp Phe Pro Ala Asp Lys Tyr Glu Glu
                 35                  40                  45

Tyr Val Arg Thr Phe Thr Lys Pro Ser Glu Thr Pro Gly Phe Arg Glu
                 50                  55                  60

Thr Val Tyr Asn Thr Val Asn Ala Asn Thr Met Asp Ala Ile His Gln
       65                  70                  75                  80

Phe Ile Ile Leu Thr Asn Val Leu Gly Ser Arg Val Leu Ala Pro Ala
                         85                  90                  95

Leu Thr Asn Ser Leu Thr Pro Ile Lys Asp Met Ser Leu Glu Asp Arg
                    100                 105                 110

Glu Lys Leu Leu Ala Ser Trp Arg Asp Ser Pro Ile Ala Ala Lys Arg
                    115                 120                 125

Lys Leu Phe Arg Leu Val Ser Thr Leu Thr Leu Val Thr Phe Thr Arg
                    130                 135                 140

Leu Ala Asn Glu Leu His Leu Lys Ala Ile His Tyr Pro Gly Arg Glu
      145                 150                 155                 160

Asp Arg Glu Lys Ala Tyr Glu Thr Gln Glu Ile Asp Pro Phe Lys Tyr
                    165                 170                 175

Gln Phe Leu Glu Lys Pro Lys Phe Tyr Gly Ala Glu Leu Tyr Leu Pro
                    180                 185                 190

Asp Ile Asp Val Ile Ile Gly Ser Gly Ala Gly Ala Gly Val Val
                    195                 200                 205

Ala His Thr Leu Thr Asn Asp Gly Phe Lys Ser Leu Val Leu Glu Lys
                    210                 215                 220

Gly Arg Tyr Phe Ser Asn Ser Glu Leu Asn Phe Asp Asp Lys Asp Gly
      225                 230                 235                 240

Val Gln Glu Leu Tyr Gln Ser Gly Gly Thr Leu Thr Thr Val Asn Gln
                    245                 250                 255

Gln Leu Phe Val Leu Ala Gly Ser Thr Phe Gly Gly Thr Thr Val
                    260                 265                 270

Asn Trp Ser Ala Cys Leu Lys Thr Pro Phe Lys Val Arg Lys Glu Trp
                    275                 280                 285

Tyr Asp Glu Phe Gly Val Asp Phe Ala Ala Asp Glu Ala Tyr Asp Lys
                    290                 295                 300

Ala Gln Asp Tyr Val Trp Gln Gln Met Gly Ala Ser Thr Glu Gly Ile
      305                 310                 315                 320

Thr His Ser Leu Ala Asn Glu Ile Ile Ile Glu Gly Gly Lys Lys Leu
                    325                 330                 335

Gly Tyr Lys Ala Lys Val Leu Asp Gln Asn Ser Gly Gly His Pro His
                    340                 345                 350

His Arg Cys Gly Phe Cys Tyr Leu Gly Cys Lys His Gly Ile Lys Gln
                    355                 360                 365

Gly Ser Val Asn Asn Trp Phe Arg Asp Ala Ala His Gly Ser Gln
                    370                 375                 380

Phe Met Gln Gln Val Arg Val Leu Gln Ile Leu Asn Lys Lys Gly Ile
      385                 390                 395                 400

Ala Tyr Gly Ile Leu Cys Glu Asp Val Val Thr Gly Ala Lys Phe Thr
                    405                 410                 415

Ile Thr Gly Pro Lys Lys Phe Val Val Ala Ala Gly Ala Leu Asn Thr
                    420                 425                 430

Pro Ser Val Leu Val Asn Ser Gly Phe Lys Asn Lys Asn Ile Gly Lys
                    435                 440                 445
```

```
Asn Leu Thr Leu His Pro Val Ser Val Val Phe Gly Asp Phe Gly Lys
    450                 455                 460

Asp Val Gln Ala Asp His Phe His Asn Ser Ile Met Thr Ala Leu Cys
465                 470                 475                 480

Ser Glu Ala Ala Asp Leu Asp Gly Lys Gly His Gly Cys Arg Ile Glu
                485                 490                 495

Thr Ile Leu Asn Ala Pro Phe Ile Gln Ala Ser Phe Leu Pro Trp Arg
            500                 505                 510

Gly Ser Asn Glu Ala Arg Arg Asp Leu Leu Arg Tyr Asn Asn Met Val
        515                 520                 525

Ala Met Leu Leu Leu Ser Arg Asp Thr Thr Ser Gly Ser Val Ser Ser
    530                 535                 540

His Pro Thr Lys Pro Glu Ala Leu Val Val Glu Tyr Asp Val Asn Lys
545                 550                 555                 560

Phe Asp Arg Asn Ser Ile Leu Gln Ala Leu Leu Val Thr Ala Asp Leu
                565                 570                 575

Leu Tyr Ile Gln Gly Ala Lys Arg Ile Leu Ser Pro Gln Pro Trp Val
            580                 585                 590

Pro Ile Phe Glu Ser Asp Lys Pro Lys Asp Lys Arg Ser Ile Lys Asp
        595                 600                 605

Glu Asp Tyr Val Glu Trp Arg Ala Lys Val Ala Lys Ile Pro Phe Asp
    610                 615                 620

Thr Tyr Gly Ser Pro Tyr Gly Ser Ala His Gln Met Ser Ser Cys Arg
625                 630                 635                 640

Met Ser Gly Lys Gly Pro Lys Tyr Gly Ala Val Asp Thr Asp Gly Arg
                645                 650                 655

Leu Phe Glu Cys Ser Asn Val Tyr Val Ala Asp Ala Ser Leu Leu Pro
            660                 665                 670

Thr Ala Ser Gly Ala Asn Pro Met Val Thr Thr Met Thr Leu Ala Arg
        675                 680                 685

His Val Ala Leu Gly Leu Ala Asp Ser Leu Lys Thr Lys Ala Lys Leu
    690                 695                 700

<210> SEQ ID NO 41
<211> LENGTH: 2115
<212> TYPE: DNA
<213> ORGANISM: Candida tropicalis

<400> SEQUENCE: 41
atggctccat ttttgcccga ccaggtcgac tacaaacacg tcgacaccct tatgttatta      60
tgtgacggga tcatccacga aaccaccgtg gacgaaatca agacgtcat tgcccctgac     120 ttccccgccg acaaatacga ggagtacgtc aggacattac ccaaaccctc cgaaacccca     180
gggttcaggg aaaccgtcta caacaccgtc aacgcaaaca ccatggatgc aatccaccag     240
ttcattatct tgaccaatgt tttgggatca agggtcttgg caccagcttt gaccaactcg     300
ttgactccta tcaaggacat gagcttggaa gaccgtgaaa agttgttagc ctcgtggcgt     360 gactcccta tgctgctaa aaggaagttg ttcaggttgg tttctacgct taccttggtc     420
acgttcacga gattggccaa tgagttgcat ttgaaagcca ttcattatcc aggaagagaa     480
gaccgtgaaa aggcttatga aacccaggag attgaccctt taagtacca gttttggaa     540 aaaccgaagt tttacggcgc tgagttgtac ttgccagata ttgatgtgat cattattgga     600 tctgggggccg gtgctggtgt cgtggcccac actttgacca cgacggctt caagagtttg     660
```

```
gttttggaaa agggcagata ctttagcaac tccgagttga actttgatga caaggacggg    720
gttcaagaat ataccaaag tggaggtact tgaccaccg tcaaccagca gttgtttgtt      780
cttgctggtt ccactttgg tggtggtacc actgtcaatt ggtcggcctg tcttaaaacg    840
ccattcaagg tgcgtaagga atggtatgat gagtttggcg ttgactttgc tgccgatgaa    900
gcctacgaca aagcacagga ttatgtttgg cagcaaatgg gagcttctac cgaaggcatc    960
acccactctt tggctaacga gattattatt gaaggtggca agaaattagg ttacaaggcc   1020
aaggtattag accaaaacag cggtggtcat cctcatcaca gatgcggttt ctgttatttg   1080
ggttgtaagc acggtatcaa gcagggctct gttaataact ggtttagaga cgcagctgcc   1140
cacggttctc agttcatgca acaggttaga gttttgcaaa tccttaacaa gaagggcatc   1200
gcttatggta tcttgtgtga ggatgttgta accggtgcca agttcaccat tactggcccc   1260
aaaaagtttg ttgttgccgc cggcgcctta acactccat ctgtgttggt caactccgga   1320
ttcaagaaca agaacatcgg taagaactta actttgcatc cagtttctgt cgtgtttggt   1380
gattttggca aagacgttca agcagatcac ttccacaact ccatcatgac tgctctttgt   1440
tcagaagccg ctgatttaga cggcaagggt catggatgca gaattgaaac catcttgaac   1500
gctccattca tccaggcttc attcttacca tggagaggta gtaacgaggc tagacgagac   1560
ttgttgcgtt acaacaacat ggtggccatg ttacttctta gtcgtgatac caccagtggt   1620
tccgtttcgt cccatccaac taaacctgaa gcattagttg tcgagtacga cgtgaacaag   1680
tttgacagaa actccatctt gcaggcattg ttggtcactg ctgacttgtt gtacattcaa   1740
ggtgccaaga gaatccttag tccccaacca tgggtgccaa ttttttgaatc cgacaagcca   1800
aaggataaga gatcaatcaa ggacgaggac tatgtcgaat ggagagccaa ggttgccaag   1860
attccttttg acacctacgg ctcgcccttat ggttcggcgc atcaaatgtc ttcttgtcgt   1920
atgtcaggta agggtcctaa atacggtgct gttgataccg atggtagatt gtttgaatgt   1980
tcgaatgttt atgttgctga cgctagtctt ttgccaactg ctagcggtgc taatcctatg   2040
gtcaccacca tgactcttgc aagacatgtt gcgttaggtt tggcagactc cttgaagacc   2100
aaggccaagt gtag                                                     2115
```

<210> SEQ ID NO 42
<211> LENGTH: 470
<212> TYPE: PRT
<213> ORGANISM: Marinobacter aquaeolei VT8

<400> SEQUENCE: 42

```
Met Pro Thr Leu Pro Arg Thr Phe Asp Asp Ile Gln Ser Arg Leu Ile
1               5                   10                  15

Asn Ala Thr Ser Arg Val Val Pro Met Gln Arg Gln Ile Gln Gly Leu
            20                  25                  30

Lys Phe Leu Met Ser Ala Lys Arg Lys Thr Phe Gly Pro Arg Arg Pro
        35                  40                  45

Met Pro Glu Phe Val Glu Thr Pro Ile Pro Asp Val Asn Thr Leu Ala
    50                  55                  60

Leu Glu Asp Ile Asp Val Ser Asn Pro Phe Leu Tyr Arg Gln Gly Gln
65                  70                  75                  80

Trp Arg Ala Tyr Phe Lys Arg Leu Arg Asp Glu Ala Pro Val His Tyr
                85                  90                  95

Gln Lys Asn Ser Pro Phe Gly Pro Phe Trp Ser Val Thr Arg Phe Glu
            100                 105                 110
```

```
Asp Ile Leu Phe Val Asp Lys Ser His Asp Leu Phe Ser Ala Glu Pro
            115                 120                 125

Gln Ile Ile Leu Gly Asp Pro Pro Glu Gly Leu Ser Val Glu Met Phe
        130                 135                 140

Ile Ala Met Asp Pro Pro Lys His Asp Val Gln Arg Ser Ser Val Gln
145                 150                 155                 160

Gly Val Val Ala Pro Lys Asn Leu Lys Glu Met Glu Gly Leu Ile Arg
                165                 170                 175

Ser Arg Thr Gly Asp Val Leu Asp Ser Leu Pro Thr Asp Lys Pro Phe
            180                 185                 190

Asn Trp Val Pro Ala Val Ser Lys Glu Leu Thr Gly Arg Met Leu Ala
        195                 200                 205

Thr Leu Leu Asp Phe Pro Tyr Glu Glu Arg His Lys Leu Val Glu Trp
    210                 215                 220

Ser Asp Arg Met Ala Gly Ala Ala Ser Ala Thr Gly Gly Glu Phe Ala
225                 230                 235                 240

Asp Glu Asn Ala Met Phe Asp Asp Ala Ala Asp Met Ala Arg Ser Phe
                245                 250                 255

Ser Arg Leu Trp Arg Asp Lys Glu Ala Arg Ala Ala Gly Glu Glu
            260                 265                 270

Pro Gly Phe Asp Leu Ile Ser Leu Leu Gln Ser Asn Lys Glu Thr Lys
        275                 280                 285

Asp Leu Ile Asn Arg Pro Met Glu Phe Ile Gly Asn Leu Thr Leu Leu
    290                 295                 300

Ile Val Gly Gly Asn Asp Thr Thr Arg Asn Ser Met Ser Gly Gly Leu
305                 310                 315                 320

Val Ala Met Asn Glu Phe Pro Arg Glu Phe Glu Lys Leu Lys Ala Lys
                325                 330                 335

Pro Glu Leu Ile Pro Asn Met Val Ser Glu Ile Ile Arg Trp Gln Thr
            340                 345                 350

Pro Leu Ala Tyr Met Arg Arg Ile Ala Lys Gln Asp Val Glu Leu Gly
        355                 360                 365

Gly Gln Thr Ile Lys Lys Gly Asp Arg Val Val Met Trp Tyr Ala Ser
370                 375                 380

Gly Asn Arg Asp Glu Arg Lys Phe Asp Asn Pro Asp Gln Phe Ile Ile
385                 390                 395                 400

Asp Arg Lys Asp Ala Arg Asn His Met Ser Phe Gly Tyr Gly Val His
                405                 410                 415

Arg Cys Met Gly Asn Arg Leu Ala Glu Leu Gln Leu Arg Ile Leu Trp
            420                 425                 430

Glu Glu Ile Leu Lys Arg Phe Asp Asn Ile Glu Val Val Glu Glu Pro
        435                 440                 445

Glu Arg Val Gln Ser Asn Phe Val Arg Gly Tyr Ser Arg Leu Met Val
    450                 455                 460

Lys Leu Thr Pro Asn Ser
465                 470

<210> SEQ ID NO 43
<211> LENGTH: 1413
<212> TYPE: DNA
<213> ORGANISM: Marinobacter aquaeolei VT8

<400> SEQUENCE: 43
atgccaacac tgcccagaac atttgacgac attcagtccc gactgattaa cgccacctcc      60
```

```
agggtggtgc cgatgcagag gcaaattcag ggactgaaat tcttaatgag cgccaagagg      120
aagaccttcg gcccacgccg accgatgccc gaattcgttg aaacacccat cccggacgtt      180
aacacgctgg cccttgagga catcgatgtc agcaatccgt ttttataccg gcagggtcag      240
tggcgcgcct atttcaaacg gttgcgtgat gaggcgccgg tccattacca gaagaacagc      300
cctttcggcc ccttctggtc ggtaactcgg tttgaagaca tcctgttcgt ggataagagt      360
cacgacctgt tttccgccga gccgcaaatc attctcggtg accctccgga ggggctgtcg      420
gtggaaatgt tcatagcgat ggatccgccg aaacacgatg tgcagcgcag ctcggtgcag      480
ggagtagtgg caccgaaaaa cctgaaggag atggaggggc tgatccgatc acgcaccggc      540
gatgtgcttg acagcctgcc tacagacaaa ccctttaact gggtacctgc tgtttccaag      600
gaactcacag gccgcatgct ggcgacgctt ctggattttc cttacgagga acgccacaag      660
ctggttgagt ggtcggacag aatggcaggt gcagcatcgg ccaccggcgg ggagtttgcc      720
gatgaaaatg ccatgtttga cgacgcggca gacatggccc ggtctttctc caggctttgg      780
cgggacaagg aggcgcgccg cgcagcaggc gaggagcccg ttccgatttt gatcagcctg      840
ttgcagagca acaaagaaac gaaagacctg atcaatcggc cgatggagtt tatcggtaat      900
ttgacgctgc tcatagtcgg cggcaacgat acgacgcgca actcgatgag tggtggcctg      960
gtggccatga acgaattccc cagggaattt gaaaaattga aggcaaaacc ggagttgatt     1020
ccgaacatgg tgtcggaaat catccgctgg caaacgccgc tggcctatat gccgaatc      1080 gccaagcagg atgtcgaact gggcggccag accatcaaga agggtgatcg agttgtcatg     1140
tggtacgcgt cgggtaaccg ggacgagcgc aaatttgaca ccccgatca gttcatcatt     1200 gatcgcaagg acgcacgaaa ccacatgtcg ttcggctatg gggttcaccg ttgcatgggc     1260
aaccgtctgg ctgaactgca actgcgcatc ctctgggaag aaatactcaa gcgttttgac     1320
aacatcgaag tcgtcgaaga gcccgagcgg gtgcagtcca acttcgtgcg gggctattcc     1380
aggttgatgg tcaaactgac accgaacagt taa                                 1413
```

<210> SEQ ID NO 44
<211> LENGTH: 497
<212> TYPE: PRT
<213> ORGANISM: Acinetobacter sp. OC4

<400> SEQUENCE: 44

```
Met Asn Ser Val Ala Glu Ile Phe Glu Lys Ile Thr Gln Thr Val Thr
1               5                   10                  15

Ser Thr Ala Ala Asp Val Ala Thr Thr Val Thr Asp Lys Val Lys Ser
            20                  25                  30

Asn Glu Gln Phe Gln Thr Gly Lys Gln Phe Leu His Gly Gln Val Thr
        35                  40                  45

Arg Phe Val Pro Leu His Thr Gln Val Arg Gly Ile Gln Trp Met Gln
    50                  55                  60

Lys Ala Lys Phe Arg Val Phe Asn Val Gln Glu Phe Pro Ala Phe Ile
65                  70                  75                  80

Glu Gln Pro Ile Pro Glu Val Ala Thr Leu Ala Leu Ala Glu Ile Asp
                85                  90                  95

Val Ser Asn Pro Phe Leu Tyr Lys Gln Lys Lys Trp Gln Ser Tyr Phe
            100                 105                 110

Lys Arg Leu Arg Asp Glu Ala Pro Val His Tyr Gln Ala Asn Ser Pro
        115                 120                 125

Phe Gly Ala Phe Trp Ser Val Thr Arg Tyr Asp Asp Ile Val Tyr Val
```

```
                130                 135                 140
Asp Lys Asn His Glu Ile Phe Ser Ala Glu Pro Val Ile Ala Ile Gly
145                 150                 155                 160

Asn Thr Pro Pro Gly Leu Gly Ala Glu Met Phe Ile Ala Met Asp Pro
                165                 170                 175

Pro Lys His Asp Val Gln Arg Gln Ala Val Gln Asp Val Val Ala Pro
                180                 185                 190

Lys Asn Leu Lys Glu Leu Glu Gly Leu Ile Arg Leu Arg Val Gln Glu
                195                 200                 205

Val Leu Asp Gln Leu Pro Thr Asp Gln Pro Phe Asp Trp Val Gln Asn
210                 215                 220

Val Ser Ile Glu Leu Thr Ala Arg Met Leu Ala Thr Leu Phe Asp Phe
225                 230                 235                 240

Pro Tyr Glu Lys Arg His Lys Leu Val Glu Trp Ser Asp Leu Met Ala
                245                 250                 255

Gly Thr Ala Glu Ala Thr Gly Gly Thr Val Thr Asn Leu Asp Glu Ile
                260                 265                 270

Phe Asp Ala Ala Val Asp Ala Ala Lys His Phe Ala Glu Leu Trp His
                275                 280                 285

Arg Lys Ala Ala Gln Lys Ser Ala Gly Ala Glu Met Gly Tyr Asp Leu
290                 295                 300

Ile Ser Leu Met Gln Ser Asn Glu Ala Thr Lys Asp Leu Ile Tyr Arg
305                 310                 315                 320

Pro Met Glu Phe Met Gly Asn Leu Val Leu Ile Val Gly Gly Asn
                325                 330                 335

Asp Thr Thr Arg Asn Ser Met Thr Gly Gly Val Tyr Ala Leu Asn Leu
                340                 345                 350

Phe Pro Asn Glu Phe Val Lys Leu Lys Asn Asn Pro Ser Leu Ile Pro
                355                 360                 365

Asn Met Val Ser Glu Ile Ile Arg Trp Gln Thr Pro Leu Ala Tyr Met
                370                 375                 380

Arg Arg Ile Ala Lys Gln Asp Val Glu Leu Asn Gly Gln Thr Ile Lys
385                 390                 395                 400

Lys Gly Asp Lys Val Val Met Trp Tyr Val Ser Gly Asn Arg Asp Glu
                405                 410                 415

Arg Val Ile Glu Arg Pro Asp Glu Leu Ile Ile Asp Arg Lys Gly Ala
                420                 425                 430

Arg Asn His Leu Ser Phe Gly Phe Gly Val His Arg Cys Met Gly Asn
                435                 440                 445

Arg Leu Ala Glu Met Gln Leu Arg Ile Leu Trp Glu Glu Leu Leu Gln
                450                 455                 460

Arg Phe Glu Asn Ile Glu Val Leu Gly Glu Pro Glu Ile Val Gln Ser
465                 470                 475                 480

Asn Phe Val Arg Gly Tyr Ala Lys Met Met Val Lys Leu Thr Ala Lys
                485                 490                 495

Ala
```

<210> SEQ ID NO 45
<211> LENGTH: 1494
<212> TYPE: DNA
<213> ORGANISM: Acinetobacter sp. OC4

<400> SEQUENCE: 45
atgaacagcg tagcagaaat cttcgagaaa atcacccaga ccgtcacgag caccgcagcc    60

```
gacgttgcaa ccactgtcac cgacaaggtc aaatccaacg agcaattcca aacgggtaag    120 cagttttgc acggccaggt tacgcgtttt gtgccgttgc atacgcaggt ccgtggtatt    180
cagtggatgc agaaagccaa gtttcgcgtg ttcaatgtcc aggagttccc ggcctttatt    240
gaacaaccga ttccggaagt ggcaaccctg gcgctggcgg aaattgatgt cagcaacccg    300
ttcctgtaca aacagaaaaa gtggcaaagc tacttcaaac gtctgcgtga cgaggcgcca    360
gtgcattatc aagctaacag cccgttcggt gccttttggt ctgtgacccg ttacgacgac    420
atcgtttatg ttgacaaaaa tcatgaaatc ttctccgcag aaccggtgat tgctattggt    480 aatacccgc caggcctggg tgcggaaatg ttcatcgcaa tggaccctcc gaagcacgac    540
gtccagcgcc aagcggtgca ggacgtagtt gcgccgaaga acttgaagga actggagggt    600 ctgatccgc tgcgtgtgca ggaagtcctg gatcagctgc cgacggatca gccgtttgac    660
tgggtgcaga acgtgtcgat tgaactgacc gcacgcatgc tggcgaccct gttcgacttt    720
ccgtatgaaa aacgtcataa actggtggaa tggtccgatc tgatggcagg tacggctgag    780
gccaccggcg gtactgtgac caatctggat gagattttg atgcggcggt tgacgcagcc    840
aagcacttcg ctgagctgtg caccgcaaa gcggctcaaa agagcgccgg tgcggagatg    900
ggctacgatc tgatttccct gatgcaaagc aacgaggcga cgaaagacct gatctatcgc    960
ccgatggagt tcatgggtaa cctggtcctg ctgattgttg gtggcaatga caccacccgt   1020
aatagcatga cggcggtgt ttatgcactg aacttgtttc gaatgagtt tgtcaaactg   1080 aagaataacc cgagcctgat ccctaacatg gttagcgaga ttatccgctg gcagacgccg   1140
ctggcttaca tgcgccgcat tgccaagcaa gacgtcgagc tgaacggtca aaccatcaaa   1200
aagggcgata aggtcgtgat gtggtacgtc agcggtaacc gcgacgaacg tgtgattgaa   1260
cgcccggacg aactgatcat tgatcgcaag ggtgcgcgta accacctgtc cttcggcttt   1320
ggcgtgcatc gctgcatggg taatcgtttg gccgagatgc aactgcgtat cctgtgggag   1380
gaactgttgc aacgcttcga gaatatcgaa gttctgggcg aaccggagat tgttcagtcc   1440
aatttcgtgc gtggctatgc gaagatgatg gttaaactga cggcgaaagc ctaa          1494
```

<210> SEQ ID NO 46
<211> LENGTH: 558
<212> TYPE: PRT
<213> ORGANISM: Pseudomonas putida

<400> SEQUENCE: 46

```
Met Tyr Asp Tyr Ile Ile Val Gly Ala Gly Ser Ala Gly Cys Val Leu
1               5                   10                  15

Ala Asn Arg Leu Ser Ala Asp Pro Ser Lys Arg Val Cys Leu Leu Glu
            20                  25                  30

Ala Gly Pro Arg Asp Thr Asn Pro Leu Ile His Met Pro Leu Gly Ile
        35                  40                  45

Ala Leu Leu Ser Asn Ser Lys Lys Leu Asn Trp Ala Phe Gln Thr Ala
    50                  55                  60

Pro Gln Gln Asn Leu Asn Gly Arg Ser Leu Phe Trp Pro Arg Gly Lys
65                  70                  75                  80

Thr Leu Gly Gly Ser Ser Ser Ile Asn Ala Met Val Tyr Ile Arg Gly
                85                  90                  95

His Glu Asp Asp Tyr His Ala Trp Glu Gln Ala Ala Gly Arg Tyr Trp
            100                 105                 110

Gly Trp Tyr Arg Ala Leu Glu Leu Phe Lys Arg Leu Glu Cys Asn Gln
```

```
            115                 120                 125
Arg Phe Asp Lys Ser Glu His His Gly Val Asp Gly Glu Leu Ala Val
    130                 135                 140

Ser Asp Leu Lys Tyr Ile Asn Pro Leu Ser Lys Ala Phe Val Gln Ala
145                 150                 155                 160

Gly Met Glu Ala Asn Ile Asn Phe Asn Gly Asp Phe Asn Gly Glu Tyr
                165                 170                 175

Gln Asp Gly Val Gly Phe Tyr Gln Val Thr Gln Lys Asn Gly Gln Arg
            180                 185                 190

Trp Ser Ser Ala Arg Ala Phe Leu His Gly Val Leu Ser Arg Pro Asn
        195                 200                 205

Leu Asp Ile Ile Thr Asp Ala His Ala Ser Lys Ile Leu Phe Glu Asp
    210                 215                 220

Arg Lys Ala Val Gly Val Ser Tyr Ile Lys Lys Asn Met His His Gln
225                 230                 235                 240

Val Lys Thr Thr Ser Gly Gly Glu Val Leu Leu Ser Leu Gly Ala Val
                245                 250                 255

Gly Thr Pro His Leu Leu Met Leu Ser Gly Val Gly Ala Ala Ala Glu
            260                 265                 270

Leu Lys Glu His Gly Val Ser Leu Val His Asp Leu Pro Glu Val Gly
        275                 280                 285

Lys Asn Leu Gln Asp His Leu Asp Ile Thr Leu Met Cys Ala Ala Asn
    290                 295                 300

Ser Arg Glu Pro Ile Gly Val Ala Leu Ser Phe Ile Pro Arg Gly Val
305                 310                 315                 320

Ser Gly Leu Phe Ser Tyr Val Phe Lys Arg Glu Gly Phe Leu Thr Ser
                325                 330                 335

Asn Val Ala Glu Ser Gly Gly Phe Val Lys Ser Pro Asp Arg Asp
            340                 345                 350

Arg Pro Asn Leu Gln Phe His Phe Leu Pro Thr Tyr Leu Lys Asp His
        355                 360                 365

Gly Arg Lys Ile Ala Gly Gly Tyr Gly Tyr Thr Leu His Ile Cys Asp
    370                 375                 380

Leu Leu Pro Lys Ser Arg Gly Arg Ile Gly Leu Lys Ser Ala Asn Pro
385                 390                 395                 400

Leu Gln Pro Pro Leu Ile Asp Pro Asn Tyr Leu Ser Asp His Glu Asp
                405                 410                 415

Ile Lys Thr Met Ile Ala Gly Ile Lys Ile Gly Arg Ala Ile Leu Gln
            420                 425                 430

Ala Pro Ser Met Ala Lys His Phe Lys His Glu Val Val Pro Gly Gln
        435                 440                 445

Ala Val Lys Thr Asp Asp Glu Ile Ile Glu Asp Ile Arg Arg Arg Ala
    450                 455                 460

Glu Thr Ile Tyr His Pro Val Gly Thr Cys Arg Met Gly Lys Asp Pro
465                 470                 475                 480

Ala Ser Val Val Asp Pro Cys Leu Lys Ile Arg Gly Leu Ala Asn Ile
                485                 490                 495

Arg Val Val Asp Ala Ser Ile Met Pro His Leu Val Ala Gly Asn Thr
            500                 505                 510

Asn Ala Pro Thr Ile Met Ile Ala Glu Asn Ala Ala Glu Ile Ile Met
        515                 520                 525

Arg Asn Leu Asp Val Glu Ala Leu Glu Ala Ser Ala Glu Phe Ala Arg
    530                 535                 540
```

Glu Gly Ala Glu Leu Glu Leu Ala Met Ile Ala Val Cys Met
545                 550                 555

<210> SEQ ID NO 47
<211> LENGTH: 1677
<212> TYPE: DNA
<213> ORGANISM: Pseudomonas putida

<400> SEQUENCE: 47

| | | | | | |
|---|---|---|---|---|---|
| atgtacgact | atataatcgt | tggtgctgga | tctgcaggat | gtgtgcttgc | taatcgtctt | 60 |
| tcggccgacc | cctctaaaag | agtttgttta | cttgaagctg | ggccgcgaga | tacgaatccg | 120 |
| ctaattcaca | tgccgttagg | tattgctttg | ctttcaaata | gtaaaaagtt | gaattgggct | 180 |
| tttcaaactg | cgccacagca | aaatctcaac | ggccggagcc | ttttctggcc | acgaggaaaa | 240 |
| acgttaggtg | gttcaagctc | aatcaacgca | atggtctata | tccgagggca | tgaagacgat | 300 |
| taccacgcat | gggagcaggc | ggccggccgc | tactggggtt | ggtaccgggc | tcttgagttg | 360 |
| ttcaaaaggc | ttgaatgcaa | ccagcgattc | gataagtccg | agcaccatgg | ggttgacgga | 420 |
| gaattagctg | ttagtgattt | aaaatatatc | aatccgctta | gcaaagcatt | cgtgcaagcc | 480 |
| ggcatggagg | ccaatattaa | tttcaacgga | gatttcaacg | gcgagtacca | ggacggcgta | 540 |
| gggttctatc | aagtaaccca | aaaaaatgga | caacgctgga | gctcggcgcg | tgcattcttg | 600 |
| cacggtgtac | tttccagacc | aaatctagac | atcattactg | atgcgcatgc | atcaaaaatt | 660 |
| cttttttgaag | accgtaaggc | ggttggtgtt | tcttatataa | agaaaaatat | gcaccatcaa | 720 |
| gtcaagacaa | cgagtggtgg | tgaagtactt | cttagtcttg | gcgcagtcgg | cacgcctcac | 780 |
| cttctaatgc | tttctggtgt | tggggctgca | gccgagctta | aggaacatgg | tgtttctcta | 840 |
| gtccatgatc | ttcctgaggt | ggggaaaaat | cttcaagatc | atttggacat | cacattgatg | 900 |
| tgcgcagcaa | attcgagaga | gccgataggt | gttgctcttt | cttcatccc | tcgtggtgtc | 960 |
| tcgggtttgt | tttcgtatgt | gtttaagcgc | gaggggtttc | tcactagtaa | cgtggcagag | 1020 |
| tcgggtggtt | ttgtaaaaag | ttctcctgat | cgtgatcggc | ccaatttgca | gtttcatttc | 1080 |
| cttccaactt | atcttaaaga | tcacggtcga | aaaatagcgg | gtggttatgg | ttatacgcta | 1140 |
| catatatgtg | atcttttgcc | taagagccga | ggcagaattg | gcctaaaaag | cgccaatcca | 1200 |
| ttacagccgc | ctttaattga | cccgaactat | cttagcgatc | atgaagatat | taaaaccatg | 1260 |
| attgcgggta | ttaagatagg | gcgcgctatt | ttgcaggccc | catcgatggc | gaagcatttt | 1320 |
| aagcatgaag | tagtaccggg | ccaggctgtt | aaaactgatg | atgaaataat | cgaagatatt | 1380 |
| cgtaggcgag | ctgagactat | ataccatccg | gtaggtactt | gtaggatggg | taaagatcca | 1440 |
| gcttcagttg | ttgatccgtg | cctgaagatc | cgtgggttgg | caaatattag | agtcgttgat | 1500 |
| gcgtcaatta | tgccgcactt | ggtcgcgggt | aacacaaacg | ctccaactat | tatgattgca | 1560 |
| gaaaatgcgg | cagaaataat | tatgcggaat | cttgatgtgg | aagcattaga | ggctagcgct | 1620 |
| gagtttgctc | gcgagggtgc | agagctagag | ttggccatga | tagctgtctg | catgtaa | 1677 |

<210> SEQ ID NO 48
<211> LENGTH: 452
<212> TYPE: PRT
<213> ORGANISM: Pseudomonas putida

<400> SEQUENCE: 48

Met Ser Glu Gln Asn Ser Gln Thr Leu Ala Trp Gln Ser Met Ser Arg
1               5                   10                  15

-continued

```
Asp His His Leu Ala Pro Phe Ser Asp Val Lys Gln Leu Ala Glu Lys
             20                  25                  30
Gly Pro Arg Ile Ile Thr Ser Ala Lys Gly Val Tyr Leu Trp Asp Ser
         35                  40                  45
Glu Gly Asn Lys Ile Leu Asp Gly Met Ala Gly Leu Trp Cys Val Ala
 50                  55                  60
Val Gly Tyr Gly Arg Asp Glu Leu Ala Glu Val Ala Ser Gln Gln Met
 65                  70                  75                  80
Lys Gln Leu Pro Tyr Tyr Asn Leu Phe Phe Gln Thr Ala His Pro Pro
                 85                  90                  95
Ala Leu Glu Leu Ala Lys Ala Ile Ala Asp Val Ala Pro Gln Gly Met
            100                 105                 110
Asn His Val Phe Phe Thr Gly Ser Gly Ser Glu Gly Asn Asp Thr Val
            115                 120                 125
Leu Arg Met Val Arg His Tyr Trp Ala Leu Lys Gly Lys Lys Asn Lys
        130                 135                 140
Asn Val Ile Ile Gly Arg Ile Asn Gly Tyr His Gly Ser Thr Val Ala
145                 150                 155                 160
Gly Ala Ala Leu Gly Gly Met Ser Gly Met His Gln Gln Gly Gly Val
                165                 170                 175
Ile Pro Asp Ile Val His Ile Pro Gln Pro Tyr Trp Phe Gly Glu Gly
            180                 185                 190
Gly Asp Met Thr Glu Ala Asp Phe Gly Val Trp Ala Ala Glu Gln Leu
        195                 200                 205
Glu Lys Lys Ile Leu Glu Val Gly Val Asp Asn Val Ala Ala Phe Ile
210                 215                 220
Ala Glu Pro Ile Gln Gly Ala Gly Gly Val Ile Pro Pro Gln Thr
225                 230                 235                 240
Tyr Trp Pro Lys Val Lys Glu Ile Leu Ala Arg Tyr Asp Ile Leu Phe
                245                 250                 255
Val Ala Asp Glu Val Ile Cys Gly Phe Gly Arg Thr Gly Glu Trp Phe
            260                 265                 270
Gly Thr Asp Tyr Tyr Asp Leu Lys Pro Asp Leu Met Thr Ile Ala Lys
        275                 280                 285
Gly Leu Thr Ser Gly Tyr Ile Pro Met Gly Gly Val Ile Val Arg Asp
    290                 295                 300
Glu Val Ala Lys Val Ile Ser Glu Gly Gly Asp Phe Asn His Gly Phe
305                 310                 315                 320
Thr Tyr Ser Gly His Pro Val Ala Ala Val Gly Leu Glu Asn Leu
                325                 330                 335
Arg Ile Leu Arg Asp Glu Gln Ile Ile Gln Gln Val His Asp Lys Thr
            340                 345                 350
Ala Pro Tyr Leu Gln Gln Arg Leu Arg Glu Leu Ala Asp His Pro Leu
        355                 360                 365
Val Gly Glu Val Arg Gly Leu Gly Met Leu Gly Ala Ile Glu Leu Val
    370                 375                 380
Lys Asp Lys Ala Thr Arg Ala Arg Tyr Glu Gly Lys Gly Val Gly Met
385                 390                 395                 400
Ile Cys Arg Gln His Cys Phe Asp Asn Gly Leu Ile Met Arg Ala Val
                405                 410                 415
Gly Asp Thr Met Ile Ile Ala Pro Pro Leu Val Ile Ser Ile Glu Glu
            420                 425                 430
Ile Asp Glu Leu Val Glu Lys Ala Arg Lys Cys Leu Asp Leu Thr Tyr
```

Glu Ala Val Arg
    450

<210> SEQ ID NO 49
<211> LENGTH: 1359
<212> TYPE: DNA
<213> ORGANISM: Pseudomonas putida

<400> SEQUENCE: 49

```
atgagcgaac aaaactccca aaccctggcc tggcagagca tgagccgcga tcaccatctg      60
gcgccgttca gcgatgtcaa gcaattggct gaaaaaggtc cgcgcattat cacgtccgcg     120
aaaggcgtgt acctgtggga ttccgaaggt aacaaaatcc tggatggtat ggcgggtctg     180
tggtgtgtgg cggtcggtta cggtcgtgat gaactggctg aggtcgccag ccaacaaatg     240
aagcaactgc cgtactacaa cctgttcttc caaacggccc atccgccagc actggagctg     300
gcaaaagcca ttgccgacgt agctccgcaa ggtatgaacc atgttttctt caccggttct     360
ggcagcgaag gcaatgatac cgtgctgcgt atggtacgcc actattgggc cctgaaaggt     420
aagaagaaca gaatgtcat cattggtcgt atcaacggtt accacggtag cacccgtcgct     480
ggtgcggcgc tgggtggcat gagcggcatg caccagcagg tggtgtcat tccggacatt     540
gtccacattc cgcagccgta ttggtttggt gaaggcggtg acatgacgga agcggacttc     600
ggtgtgtggg ctgccgagca attggagaag aagatcctgg aggttggcgt tgataatgtt     660
gcggcgttca ttgcggaacc gatccaaggc gctggcggtg ttatcatccc gccacagacg     720
tattggccaa aggtgaaaga gatcctggcg cgctacgata tcttgttcgt tgctgacgag     780
gtgatctgcg gttttggtcg caccggcgaa tggtttggca ccgattacta cgacctgaaa     840
ccggatctga tgaccatcgc caaaggtctg accagcggct acattccgat gggtggtgtc     900
attgtccgtg atgaggttgc caaggttatc agcgagggcg tgactttaa ccacggcttt     960
acctacagcg gccatccggt ggcggcagcg gtcggtctgg aaaatctgcg tattctgcgt    1020
gacgagcaga tcatccaaca agttcacgac aagaccgctc cgtatctgca acagcgcctg    1080
cgcgaactgg cggaccatcc gctggttggc gaagtccgtg gcttgggcat gctgggtgcg    1140
attgaactgg ttaaagacaa ggcaacccgt gcacgttatg agggtaaggg cgtgggcatg    1200
atctgccgtc agcactgttt cgacaacggt ctgattatgc gtgcggttgg cgataccatg    1260
attatcgcac cgccgttggc catcagcatc gaagaaatcg acgaattggt agagaaagcg    1320
cgtaagtgtc tggatctgac gtatgaggct gtgcgctaa                            1359
```

<210> SEQ ID NO 50
<211> LENGTH: 143
<212> TYPE: DNA
<213> ORGANISM: Artificial Sequence
<220> FEATURE:
<223> OTHER INFORMATION: Synthetic isolated AlkB-Promoter

<400> SEQUENCE: 50

```
aactacccgt aggtgtagtt ggcgcaagcg tccgattagc tcaggtttaa gatgtcgaga      60
gtgagagtgg gcggcttaac tttctcagtt aggcataaaa ttacgtctta aatctcgtag     120
cgactaattt aataaaaatt gga                                             143
```

<210> SEQ ID NO 51
<211> LENGTH: 40
<212> TYPE: DNA

```
<213> ORGANISM: Artificial Sequence
<220> FEATURE:
<223> OTHER INFORMATION: Synthetic Primer

<400> SEQUENCE: 51
ttaataaaaa ttggagtaca gactttggt aggagaatgc                               40

<210> SEQ ID NO 52
<211> LENGTH: 32
<212> TYPE: DNA
<213> ORGANISM: Artificial Sequence
<220> FEATURE:
<223> OTHER INFORMATION: Synthetic Primer

<400> SEQUENCE: 52
ccttgggctt atttttttagc cgtcaactta ac                                     32

<210> SEQ ID NO 53
<211> LENGTH: 32
<212> TYPE: DNA
<213> ORGANISM: Artificial Sequence
<220> FEATURE:
<223> OTHER INFORMATION: Synthetic Primer

<400> SEQUENCE: 53
aaaaataagc ccaaggcaca gataaagaga ga                                      32

<210> SEQ ID NO 54
<211> LENGTH: 32
<212> TYPE: DNA
<213> ORGANISM: Artificial Sequence
<220> FEATURE:
<223> OTHER INFORMATION: Synthetic Primer

<400> SEQUENCE: 54
tagatccttc agatcaaaga ctttaattca ac                                      32

<210> SEQ ID NO 55
<211> LENGTH: 32
<212> TYPE: DNA
<213> ORGANISM: Artificial Sequence
<220> FEATURE:
<223> OTHER INFORMATION: Synthetic Primer

<400> SEQUENCE: 55
tgatctgaag gatctaggaa ccaaggagag tg                                      32

<210> SEQ ID NO 56
<211> LENGTH: 40
<212> TYPE: DNA
<213> ORGANISM: Artificial Sequence
<220> FEATURE:
<223> OTHER INFORMATION: Synthetic Primer

<400> SEQUENCE: 56
cttggctgca ggtcgattag aaaacatatg acgcaccaag                              40

<210> SEQ ID NO 57
<211> LENGTH: 7675
<212> TYPE: DNA
<213> ORGANISM: Artificial Sequence
<220> FEATURE:
<223> OTHER INFORMATION: Synthetic Vector

<400> SEQUENCE: 57
atcgattgga tgcccgaggc atagactgta caaaaaaaca gtcataacaa gccatgaaaa        60
```

-continued

```
ccgccactgc gccgttacca ccgctgcgtt cggtcaaggt tctggaccag ttgcgtgagc    120
gcatacgcta cttgcattac agtttacgaa ccgaacaggc ttatgtcaat tcgcctctca    180
ggcgccgctg gtgccgctgg ttggacgcca agggtgaatc cgcctcgata ccctgattac    240
tcgcttcctg cgccctctca ggcggcgata ggggactggt aaaacgggga ttgcccagac    300
gcctcccccg cccctccagg ggcacaaatg cggccccaac ggggccacgt agtggtgcgt    360
tttttgcgtt tccacccttt tcttcctttt cccttttaaa ccttttagga cgtctacagg    420
ccacgtaatc cgtggcctgt agagtttaaa aagggacgga tttgttgcca ttaagggacg    480
gatttgttgt taagaaggga cggatttgtt gttgtaaagg gacggatttg ttgtattgtg    540
ggacgcagat acagtgtccc cttatacaca aggaatgtcg aacgtggcct cacccccaat    600
ggtttacaaa agcaatgccc tggtcgaggc cgcgtatcgc ctcagtgttc aggaacagcg    660
gatcgttctg gcctgtatta gccaggtgaa gaggagcgag cctgtcaccg atgaagtgat    720
gtattcagtg acggcggagg acatagcgac gatggcgggt gtccctatcg aatcttccta    780
caaccagctc aaagaagcgg ccctgcgcct gaaacggcgg gaagtccggt taacccaaga    840
gcccaatggc aaggggaaaa gaccgagtgt gatgattacc ggctgggtgc aaacaatcat    900
ctaccgggag ggtgagggcc gtgtagaact caggttcacc aaagacatgc tgccgtacct    960
gacggaactc accaaacagt tcaccaaata cgccttggct gacgtggcca agatggacag   1020
cacccacgcg atcaggcttt acgagctgct catgcaatgg gacagcatcg ccagcgcga   1080 aatagaaatt gaccagctgc gaaagtggtt tcaactggaa ggccggtatc cctcgatcaa   1140
ggacttcaag ttgcgagtgc ttgatccagc cgtgacgcag atcaacgagc acagcccgct   1200
acaggtggag tgggcgcagc gaaagaccgg gcgcaaggtc acacatctgt tgttcagttt   1260
tggaccgaag aagcccgcca aggcggtggg taaggcccca gcgaagcgca aggccgggaa   1320
gatttcagat gctgagatcg cgaaacaggc tcgccctggt gagacatggg aagcggcccg   1380
cgctcgacta acccagatgc cgctggatct ggcctagagg ccgtggccac cacggcccgg   1440
cctgcctttc aggctgcatt attgaagcat ttatcagggt tatttgtctca tgagcggata   1500 catatttgaa tgtatttaga aaaataaaca aaagagtttg tagaaacgca aaaaggccat   1560
ccgtcaggat ggccttctgc ttaatttgat gcctggcagt ttatgcgggg cgtcctgccc   1620
gccaccctcc gggccgttgc ttcgcaacgt tcaaatccgc tcccggcgga tttgtcctac   1680
tcaggagagc gttcaccgac aaacaacaga taaaacgaaa ggcccagtct ttcgactgag   1740
cctttcgttt tatttgatgc ctggcagttc cctactctcg catggggaga ccccacacta   1800
ccatcggcgc tacggcgttt cacttctgag ttcggcatgg ggtcaggtgg gaccaccgcg   1860
ctactgcccg caggcaaatt ctgttttatc agaccgcttc tgcgttctga tttaatctgt   1920
atcaggctga aaatcttctc tcatccgcca aaacagaagc ttggctgcag gtcgacggat   1980
cccgggcgcg ccaagcatat ggaattctcc aattttttatt aaattagtcg ctacgagatt   2040
taagacgtaa ttttatgcct aactgagaaa gttaagccgc ccactctcac tctcgacatc   2100
ttaaacctga gctaatcgga cgcttgcgcc aactacacct acgggtagtt tttgctccgt   2160
cgtctgctgg aaaaacacga gctggccgca agcatgccag gtaccgcgag ctactcgcga   2220
cggctgaaag caccgaaatg agcgagctat ctggtcgatt ttgacccggt gccgtcttc   2280 aaaatcggcg aaggccgaag tcggccgaaa atagcggcct acttcagacc ttccctagta   2340 aatatttttgc accaccgatc atgccgacta cacttaagtg tagttttaat atttaacacc   2400
```

```
gtaacctatg gtgaaaattt ccagtcagct ggcgcgagaa tagcataatg aaaataataa    2460
taaataatga tttcccggtc gctaaggtcg gagcggatca aattacgact ctagtaagtg    2520
ccaaagttca tagttgcata tatcggccaa gattgagtat cgcggatgga gccgctccca    2580
gagtatgcct ttacagagcc ccacctggat atgggaaaac cgttgctctt gcgttcgagt    2640
ggctacgcca cagaacagcc ggacgtcctg cagtgtggct ttctttaaga gccagttctt    2700
acagtgaatt tgatatctgc gcagagatta ttgagcagct tgaaactttc gaaatggtaa    2760
aattcagccg tgtgagagag ggtgtgagca agcctgcgct cttgcgagac cttgcatcta    2820
gtctttggca gagcacctcg aataacgaga tagaaacgct agtttgtttg gataatatta    2880
atcatgactt agacttgccg ttgttgcacg cacttatgga gtttatgtta aatacaccaa    2940
aaaatatcag gtttgcagtt gcaggcaata caataaaagg gttctcgcag cttaaacttg    3000
caggcgctat gcgggagtac accgagaaag acttggcctt tagcgcagaa gaggcggtgg    3060
cgttagcgga ggcagagtct gttcttggag ttcctgaaga acagatagag accttggtgc    3120
aagaagttga ggggtggcct gctcttgtag ttttttttgtt aaagcgtgag ttgccggcca    3180
agcatatttc agcagtagtt gaagtagaca attactttag ggatgaaata tttgaggcga    3240
ttcccgagcg ctatcgtgtt tttccttgcaa attcttcatt gctcgatttc gtgacgcctg    3300
atcaatacaa ttatgtattc aaatgcgtca atggggtctc atgtattaag tatttaagca    3360
ctaattacat gttgcttcgc catgtgagcg gtgagccagc gcagtttaca ctgcatccag    3420
tactgcgtaa ttttctacga gaaattactt ggactgaaaa tcctgctaaa agatcctacc    3480
tgcttaagcg tgcagctttc tggcattggc gtagaggtga ataccagtat gcaatacgaa    3540
tatccctacg ggcgaatgac tgtcgctggg cagtcagcat gtctgagaga ataattttag    3600
atttgtcatt tcgtcagggc gaaatagatg cgctgagaca gtggctgtta gagctgccga    3660
agcaggcctg gcaccaaaaa cccatagtgc ttattagtta cgcgtgggta ttgtatttca    3720
gtcagcaagg cgcgcgagca gagaagttaa ttaaagacct atcttcacaa tccgataaaa    3780
aaaataaatg gcaagaaaag gaatggctgc agcttgtgct tgcaataggt aaagcaacca    3840
aagatgaaat gctttcgagt gaggagctct gtaataagtg gattagttta tttggggatt    3900
caaacgcagt tggaaaaggg gccgcgctaa cctgtttggc ttttattttt gccagtgagt    3960
atagatttgc agagttggag aaggtgctgg ctcaggccca agccgtgaat aaatttgcaa    4020
aacaaaattt tgcttttggt tggctgtatg tcgcgaggtt tcaacaagcc ctagcaagcg    4080
gaaaaatggg ctgggcgagg cagattataa ctcaagcacg cacagacagt cgcgcgcaga    4140
tgatggaatc cgagtttact tcgaaaatgt ttgacgctct agagcttgag ttacattatg    4200
aattgcgctg cttggacacc tcagaagaaa agctctccaa aattttagag ttcatttcca    4260
atcacggggt gacagacgtg ttttttttccg tatgccgtgc tgtgtcagct ggcggcttg    4320
gaaggagtga cctaaatggc tccattgaga tattggagtg ggcgaaggcg catgcggttg    4380
aaaaaaatct accaagattg gaagttatga gccaaattga gatctatcag cgcttagtct    4440
gtcaaggcat aacgggcata ataattttaa aaactcttga agatcataag attttctccg    4500
gacagcactc agccccccta aaagcacgcc tgctgcttgt tcaatcacta gtgctttccc    4560
gagatcggaa cttttcatagt gccgcgcaca gagcgttatt ggctattcag caagcccgta    4620
aaattaacgc gggccagctg gaagtccgtg gattattgtg tttggccgga gcgcaggcag    4680
gtgccggtga tttaaaaaag gctcagctta acattgttta tgcagtggag atagcaaaac    4740
agcttcaatg ctttcaaaca gttcttgatg aagtatgttt aattgagcga ataataccgg    4800
```

```
cttcatgtga agccttcaca gcagttaatt tagatcaagc gattggggct tttagtcttc    4860
cgcgaatagt tgagattgga aagtccgcag agaataaagc tgacgcttta ttgacacgga    4920
agcagattgc tgtcttgagg cttgtaaaag aggggtgctc aaacaaacaa atagcaacaa    4980
atatgcatgt caccgaagat gctataaagt ggcacatgag gaaaatattt gccaccttga    5040
atgtagtgaa tcgcacgcaa gcaacaattg aagctgagcg tcaaggaatt atctaaaata    5100
atcggcatta agtgatatag tgaaaagtat actcgagctc atagtccacg acgcccgtga    5160
ttttgtagcc ctggccgacg gccagcaggt aggccgacag gctcatgccg gccgccgccg    5220 cctttcctc aatcgctctt cgttcgtctg gaaggcagta caccttgata ggtgggctgc     5280
ccttcctggt tggcttggtt tcatcagcca tccgcttgcc ctcatctgtt acgccggcgg    5340
tagccggcca gcctcgcaga gcaggattcc cgttgagcac cgccaggtgc gaataaggga    5400
cagtgaagaa ggaacacccg ctcgcgggtg ggcctacttc acctatcctg cccggctgac    5460
gccgttggat acaccaagga aagtctacac gaacccttg gcaaaatcct gtatatcgtg     5520
cgaaaaagga tggatatacc gaaaaaatcg ctataatgac cccgaagcag ggttatgcag    5580
cggaaaagcg ctgcttccct gctgttttgt ggaatatcta ccgactggaa acaggcaaat    5640
gcaggaaatt actgaactga ggggacaggc gagagaggat caatggctat ctgggggacc    5700
gagggctgtc gctgcgccaa ggcacgattg gagatcccct atgcggtgtg aaataccgca    5760
cagatgcgta aggagaaaat accgcatcag gcgctcttcc gcttcctcgc tcactgactc    5820
gctgcgctcg tcgttcggc tgcggcgagc ggtatcagct cactcaaagg cggtaatacg     5880
gttatccaca gaatcagggg ataacgcagg aaagaacatg tgagcaaaag gccagcaaaa    5940
ggccaggaac cgtaaaaagg ccgcgttgct ggcgttttc cataggctcc gcccccctga     6000
cgagcatcac aaaaatcgac gctcaagtca gaggtggcga aacccgacag gactataaag    6060
ataccaggcg tttccccctg gaagctccct cgtgcgctct cctgttccga cctgccgct     6120 taccggatac ctgtccgcct ttctcccttc gggaagcgtg gcgctttctc atagctcacg    6180
ctgtaggtat ctcagttcgg tgtaggtcgt tcgctccaag ctgggctgtg tgcacgaacc    6240
ccccgttcag cccgaccgct cgccttatc cggtaactat cgtcttgagt ccaacccggt     6300
aagacacgac ttatcgccac tggcagcagc cactggtaac aggattagca gagcgaggta    6360
tgtaggcggt gctacagagt tcttgaagtg gtggcctaac tacggctaca ctagaaggac    6420
agtatttggt atctgcgctc tgctgaagcc agttaccttc ggaaaaagag ttggtagctc    6480
ttgatccggc aaacaaacca ccgctggtag cggtggtttt tttgtttgca agcagcagat    6540
tacgcgcaga aaaaaggat ctcaagaaga tcctttgatc ttttctacgg ggtctgacgc     6600
tcagtggaac gaaaactcac gttaagggat tttggtcatg agattatcaa aaaggatctt    6660
cacctagatc cttttaaatt aaaaatgaag ttttaaatca atctaaagta tatatgagta    6720
aacttggtct gacagttacc aatcgattgg tcggtcattt cgaacccag agtcccgctc     6780 agaagaactc gtcaagaagg cgatagaagg cgatgcgctg cgaatcggga cggcgatac     6840 cgtaaagcac gaggaagcgg tcagcccatt cgccgccaag ctcttcagca atatcacggg    6900
tagccaacgc tatgtcctga tagcggtccg ccacacccag ccggcacag tcgatgaatc     6960 cagaaaagcg gccattttcc accatgatat tcggcaagca ggcatcgcca tgggtcacga    7020
cgagatcctc gccgtcggc atgcgcgcct tgagcctggc gaacagttcg gctgcgcga     7080 gcccctgatg ctcttcgtcc agatcatcct gatcgacaag accggcttcc atccgagtac    7140
```

| | |
|---|---|
| gtgctcgctc gatgcgatgt tccgcttggt ggtcgaatgg gcaggtagcc ggatcaagcg | 7200 |
| tatgcagccg ccgcattgca tcagccatga tggatacttt ctcggcagga gcaaggtgag | 7260 |
| atgacaggag atcctgcccc ggcacttcgc ccaatagcag ccagtccctt cccgcttcag | 7320 |
| tgacaacgtc gagcacagct gcgcaaggaa cgcccgtcgt ggccagccac gatagccgcg | 7380 |
| ctgcctcgtc ctgcagttca ttcagggcac cggacaggtc ggtcttgaca aaagaaccg | 7440 |
| ggcgccctg cgctgacagc cggaacacgg cggcatcaga gcagccgatt gtctgttgtg | 7500 |
| cccagtcata gccgaatagc ctctccaccc aagcggccgg agaacctgcg tgcaatccat | 7560 |
| cttgttcaat catgcgaaac gatcctcatc ctgtctcttg atcagatctt gatccctgc | 7620 |
| gccatcagat ccttggcggc aagaaagcca tccagtttac tttgcagggc ttccc | 7675 |

<210> SEQ ID NO 58
<211> LENGTH: 11401
<212> TYPE: DNA
<213> ORGANISM: Artificial Sequence
<220> FEATURE:
<223> OTHER INFORMATION: Synthetic Vector

<400> SEQUENCE: 58

| | |
|---|---|
| tgggaagccc tgcaaagtaa actggatggc tttcttgccg ccaaggatct gatggcgcag | 60 |
| gggatcaaga tctgatcaag agacaggatg aggatcgttt cgcatgattg aacaagatgg | 120 |
| attgcacgca ggttctccgg ccgcttgggt ggagaggcta ttcggctatg actgggcaca | 180 |
| acagacaatc ggctgctctg atgccgccgt gttccggctg tcagcgcagg ggcgcccggt | 240 |
| tctttttgtc aagaccgacc tgtccggtgc cctgaatgaa ctgcaggacg aggcagcgcg | 300 |
| gctatcgtgg ctggccacga cgggcgttcc ttgcgcagct gtgctcgacg ttgtcactga | 360 |
| agcgggaagg gactggctgc tattgggcga agtgccgggg caggatctcc tgtcatctca | 420 |
| ccttgctcct gccgagaaag tatccatcat ggctgatgca atgcggcggc tgcatacgct | 480 |
| tgatccggct acctgcccat tcgaccacca agcgaaacat cgcatcgagc gagcacgtac | 540 |
| tcggatggaa gccggtcttg tcgatcagga tgatctggac gaagagcatc aggggctcgc | 600 |
| gccagccgaa ctgttcgcca ggctcaaggc gcgcatgccc gacggcgagg atctcgtcgt | 660 |
| gacccatggc gatgcctgct tgccgaatat catggtggaa aatggccgct ttctggatt | 720 |
| catcgactgt ggccggctgg gtgtggcgga ccgctatcag gacatagcgt tggctacccg | 780 |
| tgatattgct gaagagcttg gcggcgaatg ggctgaccgc ttcctcgtgc tttacggtat | 840 |
| cgccgctccc gattcgcagc gcatcgcctt ctatcgcctt cttgacgagt tcttctgagc | 900 |
| gggactctgg ggttcgaaat gaccgaccaa gcgattggta actgtcagac caagtttact | 960 |
| catatatact ttagattgat ttaaaacttc atttttaatt taaaaggatc taggtgaaga | 1020 |
| tccttttga taatctcatg accaaaatcc cttaacgtga gttttcgttc cactgagcgt | 1080 |
| cagaccccgt agaaaagatc aaaggatctt cttgagatcc ttttttctg cgcgtaatct | 1140 |
| gctgcttgca acaaaaaaa ccaccgctac cagcggtggt ttgtttgccg gatcaagagc | 1200 |
| taccaactct ttttccgaag gtaactggct tcagcagagc gcagatacca aatactgtcc | 1260 |
| ttctagtgta gccgtagtta ggccaccact tcaagaactc tgtagcaccg cctacatacc | 1320 |
| tcgctctgct aatcctgtta ccagtggctg ctgccagtgg cgataagtcg tgtcttaccg | 1380 |
| ggttggactc aagacgatag ttaccggata aggcgcagcg gtcgggctga acggggggtt | 1440 |
| cgtgcacaca gcccagcttg gagcgaacga cctacaccga actgagatac ctacagcgtg | 1500 |
| agctatgaga aagcgccacg cttcccgaag ggagaaaggc ggacaggtat ccggtaagcg | 1560 |

```
gcagggtcgg aacaggagag cgcacgaggg agcttccagg gggaaacgcc tggtatcttt    1620
atagtcctgt cgggtttcgc cacctctgac ttgagcgtcg atttttgtga tgctcgtcag    1680
gggggcggag cctatggaaa aacgccagca acgcggcctt tttacggttc ctggccttt     1740 gctggccttt tgctcacatg ttctttcctg cgttatcccc tgattctgtg gataaccgta    1800
ttaccgcctt tgagtgagct gataccgctc gccgcagccg aacgaccgag cgcagcgagt    1860
cagtgagcga ggaagcggaa gagcgcctga tgcggtattt tctccttacg catctgtgcg    1920
gtatttcaca ccgcataggg gatctccaat cgtgccttgg cgcagcgaca gccctcggtc    1980
ccccagatag ccattgatcc tctctcgcct gtcccctcag ttcagtaatt tcctgcattt    2040
gcctgtttcc agtcggtaga tattccacaa acagcaggg aagcagcgct tttccgctgc     2100
ataaccctgc ttcggggtca ttatagcgat ttttcggta tatccatcct ttttcgcacg     2160
atatacagga ttttgccaaa gggttcgtgt agactttcct tggtgtatcc aacggcgtca    2220
gccgggcagg ataggtgaag taggcccacc cgcgagcggg tgttccttct tcactgtccc    2280
ttattcgcac ctggcggtgc tcaacgggaa tcctgctctg cgaggctggc cggctaccgc    2340
cggcgtaaca gatgagggca agcggatggc tgatgaaacc aagccaacca ggaagggcag    2400
cccacctatc aaggtgtact gccttccaga cgaacgaaga gcgattgagg aaaaggcggc    2460
ggcggccggc atgagcctgt cggcctacct gctggccgtc ggccagggct acaaaatcac    2520
gggcgtcgtg gactatgagc tcgagtatac ttttcactat atcacttaat gccgattatt    2580
ttagataatt ccttgacgct cagcttcaat tgttgcttgc gtgcgattca ctacattcaa    2640
ggtggcaaat attttcctca tgtgccactt tatagcatct tcggtgacat gcatatttgt    2700
tgctatttgt ttgtttgagc acccctcttt tacaagcctc aagacagcaa tctgcttccg    2760
tgtcaataaa gcgtcagctt tattctctgc ggactttcca atctcaacta ttcgcggaag    2820
actaaaagcc ccaatcgctt gatctaaatt aactgctgtg aaggcttcac atgaagccgg    2880
tattattcgc tcaattaaac atacttcatc aagaactgtt tgaaagcatt gaagctgttt    2940
tgctatctcc actgcataaa caatgttaag ctgagccttt tttaaatcac cggcacctgc    3000
ctgcgctccg gccaaacaca ataatccacg gacttccagc tggcccgcgt taattttacg    3060
ggcttgctga atagccaata acgtctctgtg cgcggcacta tgaaagttcc gatctcggga    3120
aagcactagt gattgaacaa gcagcaggcg tgcttttagg ggggctgagt gctgtccgga    3180
gaaaatctta tgatcttcaa gagttttaa attatttatg cccgttatgc cttgacagac     3240
taagcgctga tagatctcaa tttggctcat aacttccaat cttggtagat ttttttcaac    3300
cgcatgcgcc ttcgcccact ccaatatctc aatggagcca tttaggtcac tccttccaag    3360
ccgccaagct gacacagcac ggcatacgga aaaaacacg tctgtcaccc cgtgattgga    3420
aatgaactct aaaattttgg agagcttttc ttctgaggtg tccaagcagc gcaattcata    3480
atgtaactca agctctagag cgtcaaacat tttcgaagta aactcggatt ccatcatctg    3540
cgcgcgactg tctgtgcgtg cttgagttat aatctgcctc gcccagccca ttttccgct    3600 tgctagggct tgttgaaacc tcgcgacata cagccaacca aaagcaaaat tttgttttgc    3660
aaatttattc acggcttggg cctgagccag caccttctcc aactctgcaa atctatactc    3720
actggcaaaa ataaaagcca aacaggttag cgcggcccct tttccaactg cgtttgaatc    3780
cccaaataaa ctaatccact tattacagag ctcctcactc gaaagcattt catctttggt    3840
tgctttacct attgcaagca caagctgcag ccattccttt tcttgccatt tattttttt     3900
```

```
atcggattgt gaagataggt ctttaattaa cttctctgct cgcgcgcctt gctgactgaa    3960
atacaatacc cacgcgtaac taataagcac tatgggtttt tggtgccagg cctgcttcgg    4020
cagctctaac agccactgtc tcagcgcatc tatttcgccc tgacgaaatg acaaatctaa    4080
aattattctc tcagacatgc tgactgccca gcgacagtca ttcgcccgta gggatattcg    4140
tattgcatac tggtattcac ctctacgcca atgccagaaa gctgcacgct taagcaggta    4200
ggatctttta gcaggatttt cagtccaagt aatttctcgt agaaaattac gcagtactgg    4260
atgcagtgta aactgcgctg gctcaccgct cacatggcga agcaacatgt aattagtgct    4320
taaatactta atacatgaga ccccattgac gcatttgaat acataattgt attgatcagg    4380
cgtcacgaaa tcgagcaatg aagaatttgc aagaaaaaca cgatagcgct cgggaatcgc    4440
ctcaaatatt tcatccctaa agtaattgtc tacttcaact actgctgaaa tatgcttggc    4500
cggcaactca cgctttaaca aaaaaactac aagagcaggc caccccctcaa cttcttgcac    4560 caaggtctct atctgttctt caggaactcc aagaacagac tctgcctccg ctaacgccac    4620
cgcctcttct gcgctaaagg ccaagtcttt ctcggtgtac tcccgcatag cgcctgcaag    4680
tttaagctgc gagaaccctt ttattgtatt gcctgcaact gcaaacctga tattttttgg    4740
tgtatttaac ataaactcca taagtgcgtg caacaacggc aagtctaagt catgattaat    4800
attatccaaa caaactagcg tttctatctc gttattcgag gtgctctgcc aaagactaga    4860
tgcaaggtct cgcaagagcg caggcttgct cacaccctct ctcacacggc tgaattttac    4920
catttcgaaa gtttcaagct gctcaataat ctctgcgcag atatcaaatt cactgtaaga    4980
actggctctt aaagaaagcc acactgcagg acgtccggct gttctgtggc gtagccactc    5040
gaacgcaaga gcaacggttt tcccatatcc aggtggggct ctgtaaaggc atactctggg    5100
agcggctcca tccgcgatac tcaatcttgg ccgatatatg caactatgaa ctttggcact    5160
tactagagtc gtaatttgat ccgctccgac cttagcgacc gggaaatcat tatttattat    5220
tattttcatt atgctattct cgcgccagct gactggaaat tttcaccata ggttacggtg    5280
ttaaatatta aaactacact taagtgtagt cggcatgatc ggtggtgcaa aatatttact    5340
agggaaggtc tgaagtaggc cgctatttct ggccgacttc ggccttcgcc gattttgaag    5400
acgggcaccg ggtcaaaatc gaccagatag ctcgctcatt tcggtgcttt cagccgtcgc    5460
gagtagctcg cggtacctgg catgcttgcg gccagctcgt gttttttccag cagacgacgg    5520 agcaaaaact acccgtaggt gtagttggcg caagcgtccg attagctcag gtttaagatg    5580
tcgagagtga gagtgggcgg cttaactttc tcagttaggc ataaaattac gtcttaaatc    5640
tcgtagcgac taatttaata aaaattggag tacagacttt tggtaggaga atgcagctgt    5700
gggaaaaatc acctttattg agaatgataa aactgaacat gtaacagaat ttgaggcagg    5760
tattactttg atgcaagttg ccttagacaa cgccgttccc ggtattgatg gggattgcgg    5820
cggggagtgt gcctgtggta cctgtcacct gattgttcca gaagaatggt tcgataaaac    5880
cgggccgatt aatgatgctg aagaacaaat gttgtccatg cacctgagc gtgcaaaaac    5940 ctctcggttg gggtgtcagg ttaaggccac tgaggcaatg gacggaatga ctgttcaatt    6000
gccagaattt caaatgtaag tgcggagagc gacatgtcaa cgagttcaag tacaagtaat    6060
gacatccagg caaaaataat taacgccaca tccaaagtcg tgccaatgca tctacagatc    6120
aaggcactaa aaaacttgat gaaggtgaag cggaagacca ttggcacttc ccgccctcag    6180
gtgcactttg ttgaaaccga tttgcctgac gtcaatgatt tggcgataga agatatcgat    6240
acgagtaacc cttttttata ccgacaaggt aaggcgaatg cgtactttaa gcggttgcgt    6300
```

```
gatgaagcgc cggtgcacta tcagaagaac agtgctttcg ggccgttctg gtcggtaaca    6360
cgctacgaag atatcgtctt cgtggacaag agccatgatt tgttttccgc cgaaccccaa    6420
attatcttgg gtgatcctcc ggaaggcctg tcggttgaaa tgttcatcgc tatggatcct    6480
cccaagcacg acgtacagcg tcgggcagtc cagggtgttg ttgcgcccaa gaacctgaaa    6540
gaaatggaag gactgatccg caagcgcacc ggggacgtac tggatagcct gccgttggac    6600
actccgttca actgggtgcc ggtggtgtcg aaagagctga ccgggcgcat gctagcctca    6660
ctgttagatt tcccgtatga cgaacgcgaa aaactggttg gctggtcgga tcgattgtcc    6720
ggcgcgtcct cggcaaccgg cggcgagttt acgaatgaag atgtgttttt tgatgacgcg    6780
gcagatatgg cgtgggcttt ctccaagctt tggcgtgata agaagcccg tcaaaaagca     6840
ggtgaagagc cgggtttcga tttgatcagc atgcttcagt ccaatgaaga cacaaaagat    6900
ctgatcaatc gtcctttgga attcattggt aatctcgcgt tgttgattgt tggcggtaat    6960
gacaccacgc gtaactcaat gagcgggggg gtgctggctt taaatcagtt cccagagcaa    7020
ttcgagaagc taaggcgaa cccaaagctt atccccaata tggtctctga aatcattcgc     7080
tggcaaacgc cgcttgcgta tatgcgccgg gttgccaagc aggatgtgga gctgaacgga    7140
cagaccatca agaagggtga tcgcgtgctg atgtggtatg cgtcgggcaa ccaggatgag    7200
agaaaatttg agaatcctga gcaattcatc atcgaccgca agatacgcg taaccatgtg     7260
tcgtttggtt atggggttca ccgttgtatg ggcaaccgcc ttgccgaact gcagctgcgt    7320
attctgtggg aagagcttct ccctcgcttt gaaaacatcg aagtgatcgg tgagccggag    7380
cgcgtgcaat cgaactttgt gcggggctat tccaagatga tggttaagtt gacggctaaa    7440
aaataagccc aaggcacaga taagagaga agcatggaaa acgaaaaaca agatgccact     7500
gtcatcgttg gaggcgggca cgcagcaggt gcgttgatga cagccttgat acaaaagaaa    7560
tatccacacg aggtggttct ggtgggcgaa gagccttatc cgccctacca gcgcccgcct    7620
ttatccaaaa cgtatctgtc aggagaggtt aacgaggaat ctctctattt gaaaccgcgc    7680
tcggtgtatg aaggtgcggg gcatcagttg cgacttggtg tgcgcgttga gaacattgat    7740
cgagacaaca aaaccccttac attgtcagat cagagcacac tgaaatatgg ccgactgatt    7800
cttgccacag gttcacacgt taggcgtctt aatgcgcctg gatctgaatt aaaaggcatc    7860
cattatctgc atgacattgc tgatacggat acattgcgcg atcaactgtc accaggtgcc    7920
cgtttggtta ttgtcggtgg cggctacatt ggccttgagg ttgcagccag tgcgagcaag    7980
aaaggcgtta atgttacggt gctggaaggc gctgagcgtc taatgcagcg agttacgggc    8040
gttgagatgt cttcgttcct gtatgctaag cacagtggtt ctggcgtgga cgtgcgtctt    8100
aatactgctg tcaccggctt caaagctgga gatcaggggc gagtggctgg cgtaacgtta    8160
gcaaatggcg aaacggttga cgcagatgtt gtgcttgtct cgattggcgt tatacccgaa    8220
acggctttgg ctgaggctgc cggcctatcc tgtgaagacg gtatcctggt ggacgaatat    8280
gtccgcactt ctgacccaag catcctggcg ataggtgatt gcactcgtca ccgaaacctt    8340
ttcttcgaga aaatgcagag gctcgagtcc gttgctaacg ctgtcgatca agcacgtact    8400
gcggcagcga ccttgatggg agaggataag ccctacgata gcgctccatg gttttggtcg    8460
aatcaatatg atgttcgttt gcaaatggtg gggctctcgc aggaccatga tgaacgagtc    8520
atgcgtggca gcacggaaga caaagcgttt cggggtgttct atctccgtga gggctgtgtg    8580
attgccgttg atgcggtgaa tatgcccatt gcgtttatgg ttggaaagca gttggttcag    8640
```

```
caccgtaaga gtattagcgc tgacgtgttg agtgatctgg atgttgaatt aaagtctttg    8700
atctgaagga tctaggaacc aaggagagtg gcatatgagt ttttctaatt ataaagtaat    8760
cgcgatgccg gtgttggttg ctaattttgt tttggggggcg gccactgcat gggcgaatga   8820
aaattatccg gcgaaatctg ctggctataa tcagggtgac tgggtcgcta gcttcaattt    8880
ttctaaggtc tatgtgggtg aggagcttgg cgatctaaat gttggagggg gggctttgcc    8940
aaatgctgat gtaagtattg gtaatgatac aacacttacg tttgatatcg cctattttgt    9000
tagctcaaat atagcggtgg attttttttgt tggggtgcca gctagggcta aatttcaagg    9060
tgagaaatca atctcctcgc tgggaagagt cagtgaagtt gattacggcc ctgcaattct    9120
ttcgcttcaa tatcattacg atagctttga gcgactttat ccatatgttg gggttggtgt    9180
tggtcgggtg ctatttttttg ataaaaccga cggtgctttg agttcgtttg atattaagga    9240
taaatgggcg cctgctttttc aggttggcct tagatatgac cttggtaact catggatgct    9300
aaattcagat gtgcgttata ttccttttcaa aacggacgtc acaggtactc ttggcccggt    9360
tcctgttttct actaaaattg aggttgatcc tttcattctc agtcttggtg cgtcatatgt    9420
tttctaatcg acctgcagcc aagcttctgt tttggcggat gagagaagat tttcagcctg    9480
atacagatta aatcagaacg cagaagcggt ctgataaaac agaatttgcc tggcggcagt    9540
agcgcggtgg tcccacctga ccccatgccg aactcagaag tgaaacgccg tagcgccgat    9600
ggtagtgtgg ggtctcccca tgcgagagta gggaactgcc aggcatcaaa taaaacgaaa    9660
ggctcagtcg aaagactggg cctttcgttt tatctgttgt ttgtcggtga acgctctcct    9720
gagtaggaca atccgccgg gagcggattt gaacgttgcg aagcaacggc ccggagggtg    9780
gcgggcagga cgcccgccat aaactgccag gcatcaaatt aagcagaagg ccatcctgac    9840
ggatggcctt tttgcgtttc tacaaactct tttgtttatt tttctaaata cattcaaata    9900
tgtatccgct catgagacaa taaccctgat aaatgcttca ataatgcagc tgaaaggca    9960
ggccgggccg tggtggccac ggcctctagg ccagatccag cggcatctgg gttagtcgag  10020
cgcgggccgc ttcccatgtc tcaccagggc gagcctgttt cgcgatctca gcatctgaaa  10080
tcttcccggc cttgcgcttc gctggggcct tacccaccgc cttggcgggc ttcttcggtc  10140
caaaactgaa caacagatgt gtgaccttgc gcccggtctt tcgctgcgcc cactccacct  10200
gtagcgggct gtgctcgttg atctgcgtca cggctggatc aagcactcgc aacttgaagt  10260
ccttgatcga gggataccgg ccttccagtt gaaaccactt tcgcagctgg tcaatttcta  10320
tttcgcgctg gccgatgctg tcccattgca tgagcagctc gtaaagcctg atcgcgtggg  10380
tgctgtccat cttggccacg tcagccaagg cgtatttggt gaactgtttg gtgagttccg  10440
tcaggtacgg cagcatgtct ttggtgaacc tgagttctac acggccctca ccctcccggt  10500
agatgattgt ttgcacccag ccggtaatca tcacactcgg tcttttcccc ttgccattgg  10560
gctcttgggt taaccggact tcccgccgtt tcaggcgcag gccgcttct ttgagctggt   10620
tgtaggaaga ttcgataggg acaccgcca tcgtcgctat gtcctccgcc gtcactgaat   10680
acatcacttc atcggtgaca ggctcgctcc tcttcacctg gctaatacag gccagaacga  10740
tccgctgttc ctgaacactg aggcgatacg cggcctcgac cagggcattg cttttgtaaa  10800
ccattgggggg tgaggccacg ttcgacattc cttgtgtata agggacact gtatctgcgt   10860
cccacaatac aacaaatccg tcccttaca acaacaaatc cgtcccttct taacaacaaa   10920
tccgtccctt aatggcaaca aatccgtccc tttttaaact ctacaggcca cggattacgt   10980
ggcctgtaga cgtcctaaaa ggtttaaaag ggaaaaggaa gaaaagggtg gaaacgcaaa  11040
```

```
aaacgcacca ctacgtggcc ccgttggggc cgcatttgtg cccctgaagg ggcgggggag    11100
gcgtctgggc aatccccgtt ttaccagtcc cctatcgccg cctgagaggg cgcaggaagc    11160
gagtaatcag ggtatcgagg cggattcacc cttggcgtcc aaccagcggc accagcggcg    11220
cctgagaggc gaattgacat aagcctgttc ggttcgtaaa ctgtaatgca agtagcgtat    11280
gcgctcacgc aactggtcca gaaccttgac cgaacgcagc ggtggtaacg gcgcagtggc    11340
ggttttcatg gcttgttatg actgtttttt tgtacagtct atgcctcggg catccaatcg    11400
a                                                                    11401
```

<210> SEQ ID NO 59
<211> LENGTH: 523
<212> TYPE: PRT
<213> ORGANISM: Artificial Sequence
<220> FEATURE:
<223> OTHER INFORMATION: Synthetic Polypeptide

<400> SEQUENCE: 59

```
Met Ala Thr Gln Glu Ile Ile Asp Ser Val Leu Pro Tyr Leu Thr Lys
 1               5                  10                  15

Trp Tyr Thr Val Ile Thr Ala Ala Val Leu Val Phe Leu Ile Ser Thr
             20                  25                  30

Asn Ile Lys Asn Tyr Val Lys Ala Lys Lys Leu Lys Cys Val Asp Pro
         35                  40                  45

Pro Tyr Leu Lys Asp Ala Gly Leu Thr Gly Ile Ser Ser Leu Ile Ala
     50                  55                  60

Ala Ile Lys Ala Lys Asn Asp Gly Arg Leu Ala Asn Phe Ala Asp Glu
 65                  70                  75                  80

Val Phe Asp Glu Tyr Pro Asn His Thr Phe Tyr Leu Ser Val Ala Gly
                 85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125

Phe Ala Pro Leu Leu Gly Asp Gly Ile Phe Thr Leu Asp Gly Glu Gly
    130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285
```

```
Lys Ser Lys Ser Gly Tyr Val Phe Leu Tyr Glu Leu Val Lys Gln Thr
            290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Ile Thr Phe Glu
            355                 360                 365

Ala Leu Lys Arg Cys Glu Tyr Leu Lys Ala Ile Leu Asn Glu Thr Leu
370                 375                 380

Arg Met Tyr Pro Ser Val Pro Val Asn Phe Arg Thr Ala Thr Arg Asp
385                 390                 395                 400

Thr Thr Leu Pro Arg Gly Gly Ala Asn Gly Thr Asp Pro Ile Tyr
                405                 410                 415

Ile Pro Lys Gly Ser Thr Val Ala Tyr Val Val Tyr Thr His Arg
            420                 425                 430

Leu Glu Glu Tyr Tyr Gly Lys Asp Ala Asn Asp Phe Arg Pro Glu Arg
                435                 440                 445

Trp Phe Glu Pro Ser Thr Lys Lys Leu Gly Trp Ala Tyr Val Pro Phe
450                 455                 460

Asn Gly Gly Pro Arg Val Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Pro Lys Cys Ile His Leu Thr
            500                 505                 510

Met Ser His Asn Asp Gly Val Phe Val Lys Met
            515                 520

<210> SEQ ID NO 60
<211> LENGTH: 1572
<212> TYPE: DNA
<213> ORGANISM: Artificial Sequence
<220> FEATURE:
<223> OTHER INFORMATION: Synthetic Polypeptide for expression in E. coli

<400> SEQUENCE: 60
atggcgaccc aagaaatcat tgactctgtg ctgccatacc tgacgaagtg gtatactgtc      60
attaccgcgg ctgttctggt cttcctgatc tccactaaca tcaaaaacta cgttaaggct     120
aaaaagctga gtgcgttgat ccgccttac ctgaaggacg ctggcctgac cggtatttct     180
tctctgattg cggcaatcaa agccaaaaat gacggccgcc tggccaactt cgccgatgag     240
gtctttgacg agtatccgaa tcacaccttc tacctgtctg ttgccggtgc actgaagatc     300
gttatgactg ttgaccctga aaatatcaag gccgttctgg caactcaatt cacgacttc      360 tctctgggca cgcgtcacgc ccatttcgct ccgctgctgg gtgacggtat ctttacgctg     420
gacggtgagg gctggaaaca ctctcgcgca atgctgcgcc cacaaatttgc tcgtgaccag    480 attggtcatg taaaggcgct ggagccgcat atccagatta tggcaaaaca aatcaagctg     540
aatcagggta agaccttcga tattcaagaa ctgtttttc gctttacggt tgataccgcc     600
accgagtttc tgtttggtga atctgttcat tctctgtacg acgagaaact gggcattccg     660
actcctaatg aaatcccagg ccgtgaaaac tttgctgcgg cattcaatgt ctctcaacac     720
```

```
tacctggcaa cccgttctta ctctcagacg ttctattttc tgaccaaccc gaaggagttc    780
cgtgattgca acgctaaggt tcatcatctg gcgaaatact ttgtgaacaa agctctgaat    840
ttcaccccgg aggaactgga ggaaaaatct aaaagcggct acgttttcct gtatgagctg    900
gtgaaacaaa cccgtgatcc aaaagttctg caggaccagc tgctgaatat catggtggct    960
ggtcgtgaca ctactgcggg tctgctgtct tttgcgctgt tgaactggc gcgtcatccg    1020 gaaatgtggt ctaaactgcg tgaggaaatc gaggttaact cggtgttgg cgaggattct    1080 cgtgtggaag agatcacctt tgaagcgctg aaacgctgtg agtatctgaa agcgatcctg    1140
aacgaaacgc tgcgtatgta cccaagcgtt cctgttaatt ccgtaccgc gacgcgcgac    1200 accaccctgc cgcgtggtgg tggcgcgaat ggcacggacc caatctacat tcctaaaggc    1260
tctaccgttg cttacgttgt ttacaagacg caccgtctgg aagaatatta cggtaaagac    1320
gccaacgact tcgtccgga acgttggttc gagccttcta ccaagaagct gggttgggcg    1380
tacgtgccgt tcaacggtgg tccgcgtgtt tgcctgggcc agcagttcgc tctgacggaa    1440
gcctcctacg tcatcactcg tctggcgcag atgttcgaaa ccgttagctc cgaccctggt    1500
ctggagtacc cgcctccgaa atgcatccac ctgactatgt ctcacaacga tggtgttttc    1560
gtgaagatgt aa                                                       1572
```

<210> SEQ ID NO 61
<211> LENGTH: 517
<212> TYPE: PRT
<213> ORGANISM: Artificial Sequence
<220> FEATURE:
<223> OTHER INFORMATION: Synthetic isolated polypeptide

<400> SEQUENCE: 61

```
Met Ile Glu Gln Leu Leu Glu Tyr Trp Tyr Val Val Pro Val Leu
1               5                   10                  15

Tyr Ile Ile Lys Gln Leu Leu Ala Tyr Thr Lys Thr Arg Val Leu Met
            20                  25                  30

Lys Lys Leu Gly Ala Ala Pro Val Thr Asn Lys Leu Tyr Asp Asn Ala
        35                  40                  45

Phe Gly Ile Val Asn Gly Trp Lys Ala Leu Gln Phe Lys Lys Glu Gly
    50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Thr Leu Phe Lys Pro Leu Leu Gly
        115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205
```

Glu Ser Ile Gly Ile Asn Gln Asp Asp Ile Asp Phe Ala Gly Arg Lys
            210                 215                 220

Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                245                 250                 255

Asp Cys Thr Lys Ser Val His Lys Phe Thr Asn Tyr Val Gln Lys
            260                 265                 270

Ala Leu Asp Ala Ser Pro Glu Leu Glu Lys Gln Ser Gly Tyr Val
            275                 280                 285

Phe Leu Tyr Glu Leu Val Lys Gln Thr Arg Pro Asn Val Leu Arg
290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
            355                 360                 365

Leu Lys Ala Phe Leu Asn Glu Thr Leu Arg Ile Tyr Pro Ser Val Pro
370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Lys
            435                 440                 445

Lys Leu Gly Trp Ala Tyr Leu Pro Phe Asn Gly Gly Pro Arg Ile Cys
            450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Ser Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515

<210> SEQ ID NO 62
<211> LENGTH: 1554
<212> TYPE: DNA
<213> ORGANISM: Artificial Sequence
<220> FEATURE:
<223> OTHER INFORMATION: Synthetic isolated nucleic acid

<400> SEQUENCE: 62
atgatcgaac aactgctgga atactggtac gttgttgttc cggttctgta catcatcaaa      60
cagctgctgg cgtacaccaa acccgcgtt ctgatgaaaa aactgggtgc ggcgccggtt     120
accaacaaac tgtacgacaa cgcgttcggt atcgttaacg gttggaaagc gctgcagttc     180 aaaaagaag gtcgtgcgca ggaatacaac gactacaaat cgaccactc taaaaacccg     240 tctgttggta cctacgtttc tatcctgttc ggtacccgta tcgttgttac caaagacccg     300

-continued

```
gaaaacatca aagcgatcct ggcgacccag ttcggtgact tctctctggg taaacgtcac    360
accctgttca agccgctgct gggtgacggt atcttcaccc tggacggtga aggttggaaa    420
cactctcgcg cgatgctgcg tccgcagttc gcgcgtgaac aggttgcgca cgttacctct    480
ctggaaccgc acttccagct gctgaaaaag cacatcctga acacaaagg tgaatacttc     540 gacatccagg aactgttctt ccgtttcacc gttgactctg cgaccgaatt cctgttcggt    600
gaatctgttc actctctgaa agacgaatct atcggtatca accaggacga catcgacttc    660
gcgggtcgta aagacttcgc ggaatctttc aataaagcgc aggaatacct ggcgatccgt    720
accctggttc agaccttcta ctggctggtt aacaacaaag aattccgtga ctgcaccaaa    780
tctgttcaca aattcaccaa ctactacgtt cagaaagcgc tggacgcgtc tccggaagaa    840
ctggaaaaac agtctggtta cgtattcctg tacgaactgg ttaaacagac ccgtgacccg    900
aacgttctgc gtgaccagtc tctgaacatc ctgctggcgg tcgtgacac caccgcgggt    960 ctgctgtctt tcgcggtttt cgaactggcg cgtcacccgg aaatctgggc gaaactgcgt   1020
gaagaaatcg aacagcagtt cggtctgggt gaagactctc gtgttgaaga aatcaccttc   1080
gaatctctga acgttgcga ataccctgaaa gcgttcctga cgaaaccct gcgtatctac    1140 ccgtctgttc cgcgtaactt ccgtatcgcg accaaaaaca ccaccctgcc gcgtggtggt   1200
ggttctgacg gtacctctcc gatcctgatc cagaaaggtg aagcggtttc ttacggtatc   1260
aactctaccc acctggaccc ggtttactac ggtccggacg cggcggaatt ccgtccggaa   1320
cgttggttcg aaccgtctac caagaaactg ggttgggcgt acctgccgtt caacggtggt   1380
ccgcgtatct gcctgggtca gcagttcgcg ctgaccgaag cgggttacgt tctggttcgt   1440
ctggttcagg aattctctca cgttcgctct gacccggacg aagtttaccc gccgaaacgt   1500
ctgaccaacc tgaccatgtg cctgcaggac ggtgcgatcg ttaagttcga ctag          1554
```

<210> SEQ ID NO 63
<211> LENGTH: 680
<212> TYPE: PRT
<213> ORGANISM: Artificial Sequence
<220> FEATURE:
<223> OTHER INFORMATION: Synthetic Polypeptide

<400> SEQUENCE: 63

```
Met Ala Leu Asp Lys Leu Asp Leu Tyr Val Ile Ile Thr Leu Val Val
1               5                   10                  15

Ala Ile Ala Ala Tyr Phe Ala Lys Asn Gln Phe Leu Asp Gln Gln Gln
                20                  25                  30

Asp Thr Gly Phe Leu Asn Thr Asp Ser Gly Asp Gly Asn Ser Arg Asp
            35                  40                  45

Ile Leu Gln Ala Leu Lys Lys Asn Asn Lys Asn Thr Leu Leu Leu Phe
        50                  55                  60

Gly Ser Gln Thr Gly Thr Ala Glu Asp Tyr Ala Asn Lys Leu Ser Arg
65                  70                  75                  80

Glu Leu His Ser Arg Phe Gly Leu Lys Thr Met Val Ala Asp Phe Ala
                85                  90                  95

Asp Tyr Asp Phe Glu Asn Phe Gly Asp Ile Thr Glu Asp Ile Leu Val
            100                 105                 110

Phe Phe Ile Val Ala Thr Tyr Gly Glu Gly Glu Pro Thr Asp Asn Ala
        115                 120                 125

Asp Glu Phe His Thr Trp Leu Thr Glu Glu Ala Asp Thr Leu Ser Thr
    130                 135                 140
```

```
Leu Lys Tyr Thr Val Phe Gly Leu Gly Asn Ser Thr Tyr Glu Phe Phe
145                 150                 155                 160

Asn Ala Ile Gly Arg Lys Phe Asp Arg Leu Leu Gly Glu Lys Gly Gly
                165                 170                 175

Asp Arg Phe Ala Glu Tyr Gly Glu Gly Asp Asp Gly Thr Gly Thr Leu
            180                 185                 190

Asp Glu Asp Phe Leu Ala Trp Lys Asp Asn Val Phe Asp Ser Leu Lys
        195                 200                 205

Asn Asp Leu Asn Phe Glu Glu Lys Glu Leu Lys Tyr Glu Pro Asn Val
    210                 215                 220

Lys Leu Thr Glu Arg Asp Asp Leu Ser Gly Asn Asp Pro Asp Val Ser
225                 230                 235                 240

Leu Gly Glu Pro Asn Val Lys Tyr Ile Lys Ser Glu Gly Val Asp Leu
                245                 250                 255

Thr Lys Gly Pro Phe Asp His Thr His Pro Phe Leu Ala Arg Ile Val
            260                 265                 270

Lys Thr Lys Glu Leu Phe Thr Ser Glu Asp Arg His Cys Val His Val
        275                 280                 285

Glu Phe Asp Ile Ser Glu Ser Asn Leu Lys Tyr Thr Thr Gly Asp His
    290                 295                 300

Leu Ala Ile Trp Pro Ser Asn Ser Asp Glu Asn Ile Lys Gln Phe Ala
305                 310                 315                 320

Lys Cys Phe Gly Leu Glu Asp Lys Leu Asp Thr Val Ile Glu Leu Lys
                325                 330                 335

Ala Leu Asp Ser Thr Tyr Ser Ile Pro Phe Pro Asn Pro Ile Thr Tyr
            340                 345                 350

Gly Ala Val Ile Arg His His Leu Glu Ile Ser Gly Pro Val Ser Arg
        355                 360                 365

Gln Phe Phe Leu Ser Ile Ala Gly Phe Ala Pro Asp Glu Glu Thr Lys
    370                 375                 380

Lys Ser Phe Thr Arg Ile Gly Gly Asp Lys Gln Glu Phe Ala Ser Lys
385                 390                 395                 400

Val Thr Arg Arg Lys Phe Asn Ile Ala Asp Ala Leu Leu Phe Ala Ser
                405                 410                 415

Asn Asn Arg Pro Trp Ser Asp Val Pro Phe Glu Phe Leu Ile Glu Asn
            420                 425                 430

Val Gln His Leu Thr Pro Arg Tyr Tyr Ser Ile Ser Ser Ser Ser Leu
        435                 440                 445

Ser Glu Lys Gln Thr Ile Asn Val Thr Ala Val Val Glu Ala Glu Glu
    450                 455                 460

Glu Ala Asp Gly Arg Pro Val Thr Gly Val Val Thr Asn Leu Leu Lys
465                 470                 475                 480

Asn Ile Glu Ile Glu Gln Asn Lys Thr Gly Glu Thr Pro Met Val His
                485                 490                 495

Tyr Asp Leu Asn Gly Pro Arg Gly Lys Phe Ser Lys Phe Arg Leu Pro
            500                 505                 510

Val His Val Arg Arg Ser Asn Phe Lys Leu Pro Lys Asn Ser Thr Thr
        515                 520                 525

Pro Val Ile Leu Ile Gly Pro Gly Thr Gly Val Ala Pro Leu Arg Gly
    530                 535                 540

Phe Val Arg Glu Arg Val Gln Gln Val Lys Asn Gly Val Asn Val Gly
545                 550                 555                 560
```

```
Lys Thr Val Leu Phe Tyr Gly Cys Arg Asn Ser Glu Gln Asp Phe Leu
                565                 570                 575

Tyr Lys Gln Glu Trp Ser Glu Tyr Ala Ser Val Leu Gly Glu Asn Phe
            580                 585                 590

Glu Met Phe Asn Ala Phe Ser Arg Gln Asp Pro Thr Lys Lys Val Tyr
        595                 600                 605

Val Gln Asp Lys Ile Leu Glu Asn Ser Ala Leu Val Asp Glu Leu Leu
    610                 615                 620

Ser Ser Gly Ala Ile Ile Tyr Val Cys Gly Asp Ala Ser Arg Met Ala
625                 630                 635                 640

Arg Asp Val Gln Ala Ala Ile Ala Lys Ile Val Ala Lys Ser Arg Asp
                645                 650                 655

Ile His Glu Asp Lys Ala Ala Glu Leu Val Lys Ser Trp Lys Val Gln
            660                 665                 670

Asn Arg Tyr Gln Glu Asp Val Trp
        675                 680

<210> SEQ ID NO 64
<211> LENGTH: 2043
<212> TYPE: DNA
<213> ORGANISM: Artificial Sequence
<220> FEATURE:
<223> OTHER INFORMATION: Synthetic nucleic acid

<400> SEQUENCE: 64
atggcgctgg acaagctgga cctgtacgtt atcatcaccc tggttgttgc catcgcggcg      60
tacttcgcaa agaatcagtt cctggatcag cagcaggaca ccggcttcct gaacaccgac     120
tctggcgacg gcaattcccg tgatattctg caggcgctga gaaaaataa caaaaatacc      180 ctgctgctgt tcggttctca gaccggtacc gcggaagact acgcgaataa actgtctcgt     240
gaactgcact ctcgttttgg cctgaagacc atggttgcgg acttcgccga ctacgacttc     300
gaaaatttcg gtgacattac ggaagatatc ctggttttct tcatcgttgc gacctacggc     360
gaaggtgaac cgaccgacaa cgcggacgag ttccacacct ggctgaccga gaggcggat      420 accctgtcta ccctgaagta caccgtcttc ggcctgggta attctactta tgaattcttc     480
aacgccatcg tcgtaaatt cgaccgtctg ctgggtgaaa aggtggcga tcgtttcgcg       540 gagtacggtg agggtgacga cggtacgggt accctggacg aggactttct ggcgtggaaa     600
gacaatgttt tcgactccct gaaaaacgat ctgaactttg aggaaaaaga actgaaatac     660
gagccgaacg ttaaactgac cgaacgtgac gacctgtctg gtaatgaccc ggacgtttct     720
ctgggcgagc cgaatgttaa gtacatcaaa tctgaaggtg ttgacctgac gaaaggtccg     780
ttcgaccaca cccacccgtt cctggcacgt atcgttaaaa ccaaagagct gtttacctct     840
gaagaccgtc actgcgttca gtcgaattc gatatctctg aatctaacct gaaatacacc      900
acgggtgacc acctggcgat ctggccgtct aattctgacg aaaatatcaa acagttcgcg     960
aaatgcttcg gtctggaaga caactggat accgttatcg aactgaaagc gctggactct     1020
acgtactcca tcccgttccc gaacccgatc acctatggtg cggttatccg ccaccacctg    1080
gaaatctctg gtccggtttc tcgccagttc ttcctgtcta tcgcgggttt cgcgcctgac    1140
gaagagacga aaaatccctt cacccgtatc ggtggtgaca acaggaatt tgcgtctaag     1200 gttacccgtc gtaaattcaa catcgctgac gcgctgctgt ttgcgagcaa caatcgtccg    1260
tggtccgacg tgccattcga gtttctgatc gagaatgttc agcacctgac cccgcgttac    1320
tattctatct cctctagctc tctgtctgaa aacagacgra tcaacgttac cgctgttgta    1380
```

```
gaagcagaag aggaggcgga tggtcgtccg gttaccggtg ttgttaccaa tctgctgaaa    1440
aacatcgaaa tcgaacaaaa caaaaccggt gaaaccccga tggttcatta cgatctgaat    1500
ggtccgcgtg gtaagttctc taaattccgc ctgccggttc acgttcgtcg ttctaacttc    1560
aaactgccga aaaactccac taccccggtt attctgattg gtccgggtac tggtgttgcg    1620
ccgctgcgtg gtttcgttcg tgagcgtgtg caacaggtta aaaacggcgt taacgtcggt    1680
aagaccgtac tgttctacgg ttgccgtaac agcgaacagg actttctgta caaacaggaa    1740
tggtctgaat acgcatctgt actgggtgag aatttcgaga tgttcaacgc gttctctcgt    1800
caggacccga ccaaaaaagt ttacgttcaa gataaaatcc tggaaaactc tgcgctggtt    1860
gacgaactgc tgtcttctgg tgcaatcatt tacgtttgcg gtgatgcgtc ccgtatggcg    1920
cgtgacgttc aggcggcaat cgctaaaatc gttgctaaaa gccgtgatat ccatgaagat    1980
aaagcggcgg aactggttaa atcttggaaa gttcagaacc gctaccagga agacgtttgg    2040
taa                                                                  2043

<210> SEQ ID NO 65
<211> LENGTH: 12064
<212> TYPE: DNA
<213> ORGANISM: Artificial Sequence
<220> FEATURE:
<223> OTHER INFORMATION: Synthetic expression vector

<400> SEQUENCE: 65
atcgattgga tgcccgaggc atagactgta caaaaaaaca gtcataacaa gccatgaaaa     60
ccgccactgc gccgttacca ccgctgcgtt cggtcaaggt tctggaccag ttgcgtgagc    120
gcatacgcta cttgcattac agtttacgaa ccgaacaggc ttatgtcaat tcgcctctca    180
ggcgccgctg gtgccgctgg ttggacgcca agggtgaatc cgcctcgata ccctgattac    240
tcgcttcctg cgccctctca ggcggcgata ggggactgga aaacggggga ttgcccagac    300
gcctcccccg cccttcagg ggcacaaatg cggcccaac ggggccacgt agtggtgcgt    360
tttttgcgtt tccacccttt tcttcctttt ccttttaaa cctttttagga cgtctacagg    420 ccacgtaatc cgtggcctgt agagtttaaa aagggacgga tttgttgcca ttaagggacg    480
gatttgttgt taagaaggga cggatttgtt gttgtaaagg gacggatttg ttgtattgtg    540
ggacgcagat acagtgtccc cttatacaca aggaatgtcg aacgtggcct caccccaat    600 ggtttacaaa agcaatgccc tggtcgaggc cgcgtatcgc ctcagtgttc aggaacagcg    660
gatcgttctg gcctgtatta gccaggtgaa gaggagcgag cctgtcaccg atgaagtgat    720
gtattcagtg acggcggagg acatagcgac gatggcgggt gtccctatcg aatcttccta    780
caaccagctc aaagaagcgg ccctgcgcct gaaacggcgg gaagtccggt taacccaaga    840
gcccaatggc aagggggaaaa gaccgagtgt gatgattacc ggctgggtgc aaacaatcat    900
ctaccgggag ggtgagggcc gtgtagaact caggttcacc aaagacatgc tgccgtacct    960
gacggaactc accaaacagt tcaccaaata cgccttggct gacgtggcca agatggacag   1020
cacccacgcg atcaggcttt acgagctgct catgcaatgg gacagcatcg ccagcgcga   1080 aatagaaatt gaccagctgc gaaagtggtt tcaactggaa ggccggtatc cctcgatcaa   1140
ggacttcaag ttgcgagtgc ttgatccagc cgtgacgcag atcaacgagc acagcccgct   1200
acaggtggag tgggcgcagc gaaagaccgg gcgcaaggtc acacatctgt tgttcagttt   1260
tggaccgaag aagcccgcca aggcggtggg taaggcccca gcgaagcgca aggccgggaa   1320
```

```
gatttcagat gctgagatcg cgaaacaggc tcgccctggt gagacatggg aagcggcccg   1380
cgctcgacta acccagatgc cgctggatct ggcctagagg ccgtggccac cacggcccgg   1440
cctgcctttc aggctgcatt attgaagcat ttatcagggt tattgtctca tgagcggata   1500
catatttgaa tgtatttaga aaataaaca aaagagtttg tagaaacgca aaaaggccat    1560
ccgtcaggat ggccttctgc ttaatttgat gcctggcagt ttatggcggg cgtcctgccc   1620
gccaccctcc gggccgttgc ttcgcaacgt tcaaatccgc tcccggcgga tttgtcctac   1680
tcaggagagc gttcaccgac aaacaacaga taaaacgaaa ggcccagtct ttcgactgag   1740
cctttcgttt tatttgatgc ctggcagttc cctactctcg catggggaga ccccacacta   1800
ccatcggcgc tacggcgttt cacttctgag ttcggcatgg ggtcaggtgg gaccaccgcg   1860
ctactgccgc caggcaaatt ctgttttatc agaccgcttc tgcgttctga tttaatctgt   1920
atcaggctga aaatcttctc tcatccgcca aaacagaagc ttggctgcag gtcgacagaa   1980
gcttggctgc aggtcgatta gaaaacatat gacgcaccaa gactgagaat gaaaggatca   2040
acctcaattt tagtagaaac aggaaccggg ccaagagtac ctgtgacgtc cgttttgaaa   2100
ggaatataac gcacatctga atttagcatc catgagttac caaggtcata tctaaggcca   2160
acctgaaaag caggcgccca tttatcctta atatcaaacg aactcaaagc accgtcggtt   2220
ttatcaaaaa atagcacccg accaacacca accccaacat atggataaag tcgctcaaag   2280
ctatcgtaat gatattgaag cgaaagaatt gcagggccgt aatcaacttc actgactctt   2340
cccagcgagg agattgattt ctcaccttga aatttagccc tagctggcac cccaacaaaa   2400
aaatccaccg ctatatttga gctaacaaaa taggcgatat caaacgtaag tgttgtatca   2460
ttaccaatac ttacatcagc atttggcaaa gccccccctc caacatttag atcgccaagc   2520
tcctcaccca catagacctt agaaaaattg aagctagcga cccagtcacc ctgattatag   2580
ccagcagatt tcgccggata attttcattc gcccatgcag tggccgcccc caaaacaaaa   2640
ttagcaacca acaccggcat cgcgattact ttataattag aaaaactcat atgccactct   2700
ccttggttcc tagatccttt accaaacgtc ttcctggtag cggttctgaa cttttcaaga   2760
tttaaccagt tccgccgctt tatcttcatg gatatcacgg cttttagcaa cgattttagc   2820
gattgccgcc tgaacgtcac gcgccatacg ggacgcatca ccgcaaacgt aaatgattgc   2880
accagaagac agcagttcgt caaccagcgc agagttttcc aggattttat cttgaacgta   2940
aacttttttg gtcgggtcct gacgagagaa cgcgttgaac atctcgaaat tctcacccag   3000
tacagatgcg tattcagacc attcctgttt gtacagaaag tcctgttcgc tgttacggca   3060
accgtagaac agtacggtct taccgacgtt aacgccgttt ttaacctgtt gcacacgctc   3120
acgaacgaaa ccacgcagcg cgcaacacc agtacccgga ccaatcagaa taaccggggt    3180
agtggagttt ttcggcagtt tgaagttaga acgacgaacg tgaaccggca ggcggaattt   3240
agagaactta ccacgcggac cattcagatc gtaatgaacc atcggggttt caccggtttt   3300
gttttgttcg atttcgatgt ttttcagcag attggtaaca acaccggtaa ccggacgacc   3360
atccgcctcc tcttctgctt ctacaacagc ggtaacgttg atcgtctgtt tttcagacag   3420
agagctagag gagatagaat agtaacgcgg ggtcaggtgc tgaacattct cgatcagaaa   3480
ctcgaatggc acgtcggacc acggacgatt gttgctcgca aacagcagcg cgtcagcgat   3540
gttgaattta cgacgggtaa ccttagacgc aaattcctgt ttgtcaccac cgatacgggt   3600
gaaggatttt ttcgtctctt cgtcaggcgc gaaacccgcg atagacagga agaactggcg   3660
agaaaccgga ccagagattt ccaggtggtg gcggataacc gcaccatagg tgatcgggtt   3720
```

```
cgggaacggg atggagtacg tagagtccag cgctttcagt tcgataacgg tatccagttt    3780
gtcttccaga ccgaagcatt tcgcgaactg tttgatattt tcgtcagaat tagacggcca    3840
gatcgccagg tggtcacccg tggtgtattt caggttagat tcagagatat cgaattcgac    3900
atgaacgcag tgacggtctt cagaggtaaa cagctctttg gttttaacga tacgtgccag    3960
gaacgggtgg gtgtggtcga acggacctt cgtcaggtca acaccttcag atttgatgta     4020
cttaacattc ggctcgccca gagaaacgtc cgggtcatta ccagacaggt cgtcacgttc    4080
ggtcagttta acgttcggct cgtatttcag ttcttttttcc tcaaagttca gatcgttttt    4140
cagggagtcg aaaacattgt ctttccacgc cagaaagtcc tcgtccaggg tacccgtacc    4200
gtcgtcaccc tcaccgtact ccgcgaaacg atcgccacct ttttcaccca gcagacggtc    4260
gaatttacga ccgatggcgt tgaagaattc ataagtagaa ttacccaggc cgaagacggt    4320
gtacttcagg gtagacaggg tatccgcctc ttcggtcagc caggtgtgga actcgtccgc    4380
gttgtcggtc ggttcacctt cgccgtaggt cgcaacgatg aagaaaacca ggatatcttc    4440
cgtaatgtca ccgaaatttt cgaagtcgta gtcggcgaag tccgcaacca tggtcttcag    4500
gccaaaacga gagtgcagtt cacgagacag tttattcgcg tagtcttccg cggtaccggt    4560
ctgagaaccg aacagcagca gggtatttt gttatttttc ttcagcgcct gcagaatatc    4620
acggaaattg ccgtcgccag agtcggtgtt caggaagccg gtgtcctgct gctgatccag    4680
gaactgattc tttgcgaagt acgccgcgat ggcaacaacc agggtgatga taacgtacag    4740
gtccagcttg tccagcgcca tgcttctctc tttatctgtg ccttgggctt acatcttcac    4800
gaaaacacca tcgttgtgag acatagtcag gtggatgcat ttcggaggcg ggtactccag    4860
accagggtcg gagctaacgg tttcgaacat ctgcgccaga cgagtgatga cgtaggaggc    4920
ttccgtcaga gcgaactgct ggcccaggca aacacgcgga ccaccgttga acggcacgta    4980
cgcccaaccc agcttcttgg tagaaggctc gaaccaacgt tccggacgaa agtcgttggc    5040
gtctttaccg taatattctt ccagacggtg cgtcttgtaa acaacgtaag caacggtaga    5100
gcctttagga atgtagattg ggtccgtgcc attcgcgcca ccaccacgcg gcagggtggt    5160
gtcgcgcgtc gcggtacgga aattaacagg aacgcttggg tacatacgca gcgtttcgtt    5220
caggatcgct ttcagatact cacagcgttt cagcgcttca aaggtgatct cttccacacg    5280
agaatcctcg ccaacaccga agttaacctc gatttcctca cgcagtttag accacatttc    5340
cggatgacgc gccagttcaa acagcgcaaa agacagcaga cccgcagtag tgtcacgacc    5400
agccaccatg atattcagca gctggtcctg cagaactttt ggatcacggg tttgtttcac    5460
cagctcatac aggaaaacgt agccgctttt agattttcc tccagttcct ccggggtgaa      5520
attcagagct tgttcacaa agtatttcgc cagatgatga accttagcgt tgcaatcacg     5580
gaactccttc gggttggtca gaaaatagaa cgtctgagag taagaacggg ttgccaggta    5640
gtgttgagag acattgaatg ccgcagcaaa gttttcacgg cctgggattt cattaggagt    5700
cggaatgccc agtttctcgt cgtacagaga atgaacagat tcaccaaaca gaaactcggt    5760
ggcggtatca accgtaaagc gaaaaaacag ttcttgaata tcgaaggtct tacctgatt    5820 cagcttgatt tgttttgcca taatctggat atgcggctcc agcgccttta catgaccaat    5880
ctggtcacga gcaaattgtg ggcgcagcat tgcgcgagag tgtttccagc cctcaccgtc    5940
cagcgtaaag ataccgtcac ccagcagcgg agcgaaatgg gcgtgacgcg tgcccagaga    6000
gaagtccgtg aattgagttg ccagaacggc cttgatattt tcagggtcaa cagtcataac    6060
```

```
gatcttcagt gcaccggcaa cagacaggta gaaggtgtga ttcggatact cgtcaaagac   6120
ctcatcggcg aagttggcca ggcggccgtc attttggct tgattgccg caatcagaga     6180 agaaataccg gtcaggccag cgtccttcag gtaaggcgga tcaacgcact tcagcttttt   6240
agccttaacg tagtttttga tgttagtgga gatcaggaag accagaacag ccgcggtaat   6300
gacagtatac cacttcgtca ggtatggcag cacagagtca atgatttctt gggtcgccat   6360
gtcgctctcc gcaggcgcgc caagcatatg gaattctcca attttttatta aattagtcgc   6420 tacgagattt aagacgtaat tttatgccta actgagaaag ttaagccgcc cactctcact   6480
ctcgacatct taaacctgag ctaatcggac gcttgcgcca actacaccta cgggtagttt   6540
ttgctccgtc gtctgctgga aaaacacgag ctggccgcaa gcatgccagg taccgcgagc   6600
tactcgcgac ggctgaaagc accgaaatga gcgagctatc tggtcgattt tgacccggtg   6660
cccgtcttca aaatcggcga aggccgaagt cggccagaaa tagcggccta cttcagacct   6720
tccctagtaa atattttgca ccaccgatca tgccgactac acttaagtgt agttttaata   6780
tttaacaccg taacctatgg tgaaaatttc cagtcagctg gcgcgagaat agcataatga   6840
aaataataat aaataatgat ttcccggtcg ctaaggtcgg agcggatcaa attacgactc   6900
tagtaagtgc caaagttcat agttgcatat atcggccaag attgagtatc gcggatggag   6960
ccgctcccag agtatgcctt tacagagccc cacctggata tgggaaaacc gttgctcttg   7020
cgttcgagtg gctacgccac agaacagccg gacgtcctgc agtgtggctt tctttaagag   7080
ccagttctta cagtgaattt gatatctgcg cagagattat tgagcagctt gaaactttcg   7140
aaatggtaaa attcagccgt gtgagagagg gtgtgagcaa gcctgcgctc ttgcgagacc   7200
ttgcatctag tctttggcag agcacctcga ataacgagat agaaacgcta gtttgtttgg   7260
ataatattaa tcatgactta gacttgccgt tgttgcacgc acttatggag tttatgttaa   7320
atacaccaaa aaatatcagg tttgcagttg caggcaatac aataaaaggg ttctcgcagc   7380
ttaaacttgc aggcgctatg cgggagtaca ccgagaaaga cttggccttt agcgcagaag   7440
aggcggtggc gttagcggag gcagagtctg ttcttggagt tcctgaagaa cagatagaga   7500
ccttggtgca agaagttgag gggtggcctg ctccttgtagt ttttttgtta aagcgtgagt   7560
tgccggccaa gcatatttca gcagtagttg aagtagacaa ttactttagg gatgaaatat   7620
ttgaggcgat tcccgagcgc tatcgtgttt tccttgcaaa ttcttcattg ctcgatttcg   7680
tgacgcctga tcaatacaat tatgtattca aatgcgtcaa tggggtctca tgtattaagt   7740
atttaagcac taattacatg ttgcttcgcc atgtgagcgg tgagccagcg cagtttacac   7800
tgcatccagt actgcgtaat tttctacgag aaattacttg gactgaaaat cctgctaaaa   7860
gatcctacct gcttaagcgt gcagctttct ggcattggcg tagaggtgaa taccagtatg   7920
caatacgaat atccctacgg gcgaatgact gtcgctgggc agtcagcatg tctgagagaa   7980
taattttaga tttgtcattt cgtcagggcg aaatagatgc gctgagacag tggctgttag   8040
agctgccgaa gcaggcctgg caccaaaaac ccatagtgct tattagttac gcgtgggtat   8100
tgtatttcag tcagcaaggc gcgcgagcag agaagttaat taaagaccta tcttcacaat   8160
ccgataaaaa aaataatgg caagaaaagg aatggctgca gcttgtgctt gcaataggta   8220
aagcaaccaa agatgaaatg ctttcgagtg aggagctctg taataagtgg attagtttat   8280
ttggggattc aaacgcagtt ggaaaagggg ccgcgctaac ctgtttggct tttatttttg   8340
ccagtgagta tagatttgca gagttggaga aggtgctggc tcaggcccaa gccgtgaata   8400
aatttgcaaa acaaaatttt gcttttggtt ggctgtatgt cgcgaggttt caacaagccc   8460
```

```
tagcaagcgg aaaaatgggc tgggcgaggc agattataac tcaagcacgc acagacagtc   8520
gcgcgcagat gatggaatcc gagtttactt cgaaaatgtt tgacgctcta gagcttgagt   8580
tacattatga attgcgctgc ttggacacct cagaagaaaa gctctccaaa attttagagt   8640
tcatttccaa tcacggggtg acagacgtgt tttttccgt atgccgtgct gtgtcagctt    8700
ggcggcttgg aaggagtgac ctaaatggct ccattgagat attggagtgg gcgaaggcgc   8760
atgcggttga aaaaaatcta ccaagattgg aagttatgag ccaaattgag atctatcagc   8820
gcttagtctg tcaaggcata acgggcataa ataatttaaa aactcttgaa gatcataaga   8880
ttttctccgg acagcactca gccccctaa aagcacgcct gctgcttgtt caatcactag     8940
tgctttcccg agatcggaac tttcatagtg ccgcgcacag agcgttattg gctattcagc   9000
aagcccgtaa aattaacgcg ggccagctgg aagtccgtgg attattgtgt ttggccggag   9060
cgcaggcagg tgccggtgat ttaaaaaagg ctcagcttaa cattgtttat gcagtggaga   9120
tagcaaaaca gcttcaatgc tttcaaacag ttcttgatga agtatgttta attgagcgaa   9180
taataccggc ttcatgtgaa gccttcacag cagttaattt agatcaagcg attggggctt   9240
ttagtcttcc gcgaatagtt gagattgaa agtccgcaga gaataaagct gacgctttat     9300
tgacacggaa gcagattgct gtcttgaggc ttgtaaaaga ggggtgctca acaaacaaa     9360 tagcaacaaa tatgcatgtc accgaagatg ctataaagtg gcacatgagg aaaatatttg   9420
ccaccttgaa tgtagtgaat cgcacgcaag caacaattga agctgagcgt caaggaatta   9480
tctaaaataa tcggcattaa gtgatatagt gaaaagtata ctcgagctca tagtccacga   9540
cgcccgtgat tttgtagccc tggccgacgg ccagcaggta ggccgacagg ctcatgccgg   9600
ccgccgccgc cttttcctca atcgctcttc gttcgtctgg aaggcagtac accttgatag   9660
gtgggctgcc cttcctggtt ggcttggttt catcagccat ccgcttgccc tcatctgtta   9720
cgccggcggt agccggccag cctcgcagag caggattccc gttgagcacc gccaggtgcg   9780
aataagggac agtgaagaag gaacacccgc tcgcgggtgg gcctacttca cctatcctgc   9840
ccggctgacg ccgttggata caccaaggaa agtctacacg aacccttgg caaaatcctg     9900 tatatcgtgc gaaaaaggat ggatataccg aaaaaatcgc tataatgacc ccgaagcagg   9960
gttatgcagc ggaaaagcgc tgcttccctg ctgttttgtg gaatatctac cgactggaaa   10020
caggcaaatg caggaaatta ctgaactgag gggacaggcg agagaggatc aatggctatc   10080
tgggggaccg agggctgtcg ctgcgccaag gcacgattgg agatccccta tgcggtgtga   10140
aataccgcac agatgcgtaa ggagaaaata ccgcatcagg cgctcttccg cttcctcgct   10200
cactgactcg ctgcgctcgg tcgttcggct gcggcgagcg gtatcagctc actcaaaggc   10260
ggtaatacgg ttatccacag aatcagggga taacgcagga agaacatgt gagcaaaagg     10320 ccagcaaaag gccaggaacc gtaaaaaggc cgcgttgctg gcgttttttcc ataggctccg   10380 cccccctgac gagcatcaca aaaatcgacg ctcaagtcag aggtggcgaa acccgacagg   10440
actataaaga taccaggcgt ttccccctgg aagctccctc gtgcgctctc ctgttccgac   10500
cctgccgctt accggatacc tgtccgcctt tctcccttcg ggaagcgtgg cgctttctca   10560
tagctcacgc tgtaggtatc tcagttcggt gtaggtcgtt cgctccaagc tgggctgtgt   10620
gcacgaaccc ccgttcagc ccgaccgctg cgccttatcc ggtaactatc gtcttgagtc     10680
caacccggta agacacgact tatcgccact ggcagcagcc actggtaaca ggattagcag   10740
agcgaggtat gtaggcggtg ctacagagtt cttgaagtgg tggcctaact acggctacac   10800
```

| | |
|---|---|
| tagaaggaca gtatttggta tctgcgctct gctgaagcca gttaccttcg gaaaaagagt | 10860 |
| tggtagctct tgatccggca aacaaaccac cgctggtagc ggtggttttt ttgtttgcaa | 10920 |
| gcagcagatt acgcgcagaa aaaaggatc tcaagaagat cctttgatct tttctacggg | 10980 |
| gtctgacgct cagtggaacg aaaactcacg ttagggatt ttggtcatga gattatcaaa | 11040 |
| aaggatcttc acctagatcc ttttaaatta aaatgaagt tttaaatcaa tctaaagtat | 11100 |
| atatgagtaa acttggtctg acagttacca atcgattggt cggtcatttc gaaccccaga | 11160 |
| gtcccgctca gaagaactcg tcaagaaggc gatagaaggc gatgcgctgc gaatcgggag | 11220 |
| cggcgatacc gtaaagcacg aggaagcggt cagcccattc gccgccaagc tcttcagcaa | 11280 |
| tatcacgggt agccaacgct atgtcctgat agcggtccgc cacacccagc cggccacagt | 11340 |
| cgatgaatcc agaaaagcgg ccattttcca ccatgatatt cggcaagcag gcatcgccat | 11400 |
| gggtcacgac gagatcctcg ccgtcgggca tgcgcgcctt gagcctggcg aacagttcgg | 11460 |
| ctggcgcgag cccctgatgc tcttcgtcca gatcatcctg atcgacaaga ccggcttcca | 11520 |
| tccgagtacg tgctcgctcg atgcgatgtt tcgcttggtg gtcgaatggg caggtagccg | 11580 |
| gatcaagcgt atgcagccgc cgcattgcat cagccatgat ggatactttc tcggcaggag | 11640 |
| caaggtgaga tgacaggaga tcctgccccg gcacttcgcc caatagcagc cagtcccttc | 11700 |
| ccgcttcagt gacaacgtcg agcacagctg cgcaaggaac gcccgtcgtg gccagccacg | 11760 |
| atagccgcgc tgcctcgtcc tgcagttcat tcagggcacc ggacaggtcg gtcttgacaa | 11820 |
| aaagaaccgg gcgcccctgc gctgacagcc ggaacacggc ggcatcagag cagccgattg | 11880 |
| tctgttgtgc ccagtcatag ccgaatagcc tctccaccca gcggccgga gaacctgcgt | 11940 |
| gcaatccatc ttgttcaatc atgcgaaacg atcctcatcc tgtctcttga tcagatcttg | 12000 |
| atcccctgcg ccatcagatc cttggcggca agaaagccat ccagtttact ttgcagggct | 12060 |
| tccc | 12064 |

<210> SEQ ID NO 66
<211> LENGTH: 12046
<212> TYPE: DNA
<213> ORGANISM: Artificial Sequence
<220> FEATURE:
<223> OTHER INFORMATION: Synthetic expression vector

<400> SEQUENCE: 66

| | |
|---|---|
| atcgattgga tgcccgaggc atagactgta caaaaaaaca gtcataacaa gccatgaaaa | 60 |
| ccgccactgc gccgttacca ccgctgcgtt cggtcaaggt tctggaccag ttgcgtgagc | 120 |
| gcatacgcta cttgcattac agtttacgaa ccgaacaggc ttatgtcaat cgcctctca | 180 |
| ggcgccgctg gtgccgctgg ttggacgcca agggtgaatc cgcctcgata ccctgattac | 240 |
| tcgcttcctg cgccctctca ggcggcgata ggggactggt aaaacgggga ttgcccagac | 300 |
| gcctcccccg cccttcagg ggcacaaatg cggcccaac ggggcacgt agtggtgcgt | 360 |
| tttttgcgtt tccacccttt tcttcctttt ccctttaaa ccttttagga cgtctacagg | 420 |
| ccacgtaatc cgtggcctgt agagtttaaa aagggacgga tttgttgcca ttaagggacg | 480 |
| gatttgttgt taagaaggga cggatttgtt gttgtaaagg dacggatttg ttgtattgtg | 540 |
| ggacgcagat acagtgtccc cttatacaca aggaatgtcg aacgtggcct caccccaat | 600 |
| ggtttacaaa agcaatgccc tggtcgaggc cgcgtatcgc ctcagtgttc aggaacagcg | 660 |
| gatcgttctg gcctgtatta gccaggtgaa gaggagcgag cctgtcaccg atgaagtgat | 720 |
| gtattcagtg acggcggagg acatagcgac gatggcgggt gtccctatcg aatcttccta | 780 |

```
caaccagctc aaagaagcgg ccctgcgcct gaaacggcgg gaagtccggt taacccaaga    840
gcccaatggc aaggggaaaa gaccgagtgt gatgattacc ggctgggtgc aaacaatcat    900
ctaccgggag ggtgagggcc gtgtagaact caggttcacc aaagacatgc tgccgtacct    960 gacgaactc accaaacagt tcaccaaata cgccttggct gacgtggcca agatggacag    1020
cacccacgcg atcaggcttt acgagctgct catgcaatgg acagcatcg gccagcgcga    1080 aatagaaatt gaccagctgc gaaagtggtt tcaactggaa ggccggtatc cctcgatcaa    1140
ggacttcaag ttgcgagtgc ttgatccagc cgtgacgcag atcaacgagc acagcccgct    1200
acaggtggag tgggcgcagc gaaagaccgg gcgcaaggtc acacatctgt tgttcagttt    1260
tggaccgaag aagcccgcca aggcggtggg taaggcccca gcgaagcgca aggccgggaa    1320
gatttcagat gctgagatcg cgaaacaggc tcgccctggt gagacatggg aagcggcccg    1380
cgctcgacta acccagatgc cgctggatct ggcctagagg ccgtggccac cacggcccgg    1440
cctgcctttc aggctgcatt attgaagcat ttatcagggt tattgtctca tgagcggata    1500
catatttgaa tgtatttaga aaaataaaca aaagagtttg tagaaacgca aaaaggccat    1560
ccgtcaggat ggccttctgc ttaatttgat gcctggcagt ttatggcggg cgtcctgccc    1620
gccaccctcc gggccgttgc ttcgcaacgt tcaaatccgc tcccggcgga tttgtcctac    1680
tcaggagagc gttcaccgac aaacaacaga taaaacgaaa ggcccagtct ttcgactgag    1740
cctttcgttt tatttgatgc ctggcagttc cctactctcg catggggaga ccccacacta    1800
ccatcggcgc tacggcgttt cacttctgag ttcggcatgg ggtcaggtgg gaccaccgcg    1860
ctactgccgc caggcaaatt ctgttttatc agaccgcttc tgcgttctga tttaatctgt    1920
atcaggctga aaatcttctc tcatccgcca aaacagaagc ttggctgcag gtcgacagaa    1980
gcttggctgc aggtcgatta gaaaacatat gacgcaccaa gactgagaat gaaaggatca    2040
acctcaattt tagtagaaac aggaaccggg ccaagagtac ctgtgacgtc cgttttgaaa    2100
ggaatataac gcacatctga atttagcatc catgagttac caaggtcata tctaaggcca    2160
acctgaaaag caggcgccca tttatcctta atatcaaacg aactcaaagc accgtcggtt    2220
ttatcaaaaa atagcacccg accaacacca accccaacat atggataaag tcgctcaaag    2280
ctatcgtaat gatattgaag cgaaagaatt gcagggccgt aatcaacttc actgactctt    2340
cccagcgagg agattgattt ctcaccttga aatttagccc tagctggcac cccaacaaaa    2400
aaatccaccg ctatatttga gctaacaaaa taggcgatat caaacgtaag tgttgtatca    2460
ttaccaatac ttcatcagc atttggcaaa gcccccctc caacatttag atcgccaagc    2520
tcctcaccca catagacctt agaaaaattg aagctagcga cccagtcacc ctgattatag    2580
ccagcagatt tcgccggata atttcattc gcccatgcag tggccgcccc aaaacaaaa    2640 ttagcaacca acaccggcat cgcgattact ttataattag aaaaactcat atgccactct    2700
ccttggttcc tagatccttt accaaacgtc ttcctggtag cggttctgaa cttttccaaga   2760 tttaaccagt tccgccgctt tatcttcatg gatatcacgg cttttagcaa cgattttagc    2820
gattgccgcc tgaacgtcac gcgccatacg ggacgcatca ccgcaaacgt aaatgattgc    2880
accagaagac agcagttcgt caaccagcgc agagttttcc aggattttat cttgaacgta    2940 aactttttg gtcgggtcct gacgagagaa cgcgttgaac atctcgaaat tctcacccag    3000
tacagatgcg tattcagacc attcctgttt gtacagaaag tcctgttcgc tgttacggca    3060
accgtagaac agtacggtct taccgacgtt aacgccgttt ttaacctgtt gcacacgctc    3120
```

| | |
|---|---|
| acgaacgaaa ccacgcagcg gcgcaacacc agtacccgga ccaatcagaa taaccggggt | 3180 |
| agtggagttt ttcggcagtt tgaagttaga acgacgaacg tgaaccggca ggcggaattt | 3240 |
| agagaactta ccacgcggac cattcagatc gtaatgaacc atcggggttt caccggtttt | 3300 |
| gttttgttcg atttcgatgt ttttcagcag attggtaaca acaccggtaa ccggacgacc | 3360 |
| atccgcctcc tcttctgctt ctacaacagc ggtaacgttg atcgtctgtt tttcagacag | 3420 |
| agagctagag gagatagaat agtaacgcgg ggtcaggtgc tgaacattct cgatcagaaa | 3480 |
| ctcgaatggc acgtcggacc acggacgatt gttgctcgca aacagcagcg cgtcagcgat | 3540 |
| gttgaattta cgacgggtaa ccttagacgc aaattcctgt ttgtcaccac cgatacgggt | 3600 |
| gaaggatttt ttcgtctctt cgtcaggcgc gaaacccgcg atagacagga agaactggcg | 3660 |
| agaaaccgga ccagagattt ccaggtggtg gcggataacc gcaccatagg tgatcgggtt | 3720 |
| cgggaacggg atggagtacg tagagtccag cgctttcagt tcgataacgg tatccagttt | 3780 |
| gtcttccaga ccgaagcatt tcgcgaactg tttgatattt tcgtcagaat tagacggcca | 3840 |
| gatcgccagg tggtcacccg tggtgtattt caggttagat tcagagatat cgaattcgac | 3900 |
| atgaacgcag tgacggtctt cagaggtaaa cagctctttg gttttaacga tacgtgccag | 3960 |
| gaacgggtgg gtgtggtcga acggaccttt cgtcaggtca acaccttcag atttgatgta | 4020 |
| cttaacattc ggctcgccca gagaaacgtc cgggtcatta ccagacaggt cgtcacgttc | 4080 |
| ggtcagttta acgttcggct cgtatttcag ttcttttttcc tcaaagttca gatcgttttt | 4140 |
| cagggagtcg aaaacattgt ctttccacgc cagaaagtcc tcgtccaggg tacccgtacc | 4200 |
| gtcgtcaccc tcaccgtact ccgcgaaacg atcgccacct ttttcaccca gcagacggtc | 4260 |
| gaatttacga ccgatggcgt tgaagaattc ataagtagaa ttacccaggc cgaagacggt | 4320 |
| gtacttcagg gtagacaggg tatccgcctc ttcggtcagc caggtgtgga actcgtccgc | 4380 |
| gttgtcggtc ggttcacctt cgccgtaggt cgcaacgatg aagaaaacca ggatatcttc | 4440 |
| cgtaatgtca ccgaaatttt cgaagtcgta gtcggcgaag tccgcaacca tggtcttcag | 4500 |
| gccaaaacga gagtgcagtt cacgagacag tttattcgcg tagtcttccg cggtaccggt | 4560 |
| ctgagaaccg aacagcagca gggtattttt gttattttc ttcagcgcct gcagaatatc | 4620 |
| acgggaattg ccgtcgccag agtcggtgtt caggaagccg gtgtcctgct gctgatccag | 4680 |
| gaactgattc tttgcgaagt acgccgcgat ggcaacaacc agggtgatga taacgtacag | 4740 |
| gtccagcttg tccagcgcca tgcttctctc tttatctgtg ccttgggcct agtcgaactt | 4800 |
| aacgatcgca ccgtcctgca ggcacatggt caggttggtc agacgtttcg gcgggtaaac | 4860 |
| ttcgtccggg tcagagcgaa cgtgagagaa ttcctgaacc agacgaacca gaacgtaacc | 4920 |
| cgcttcggtc agcgcgaact gctgacccag gcagatacgc ggaccaccgt tgaacggcag | 4980 |
| gtacgcccaa cccagtttct tggtagacgg ttcgaaccaa cgttccggac ggaattccgc | 5040 |
| cgcgtccgga ccgtagtaaa ccgggtccag gtgggtagag ttgataccgt aagaaaccgc | 5100 |
| ttcacctttc tggatcagga tcggagaggt accgtcagaa ccaccaccac gcggcagggt | 5160 |
| ggtgtttttg gtcgcgatac ggaagttacg cggaacagac gggtagatac gcagggtttc | 5220 |
| gttcaggaac gctttcaggt attgcaacg tttcagagat tcgaaggtga tttcttcaac | 5280 |
| acgagagtct tcacccagac cgaactgctg ttcgatttct tcacgcagtt tcgcccagat | 5340 |
| ttccgggtga cgcgccagtt cgaaaaccgc gaaagacagc agaccgcgg tggtgtcacg | 5400 |
| acccgccagc aggatgttca gagactggtc acgcagaacg ttcgggtcac gggtctgttt | 5460 |
| aaccagttcg tacaggaata cgtaaccaga ctgttttttcc agttcttccg gagacgcgtc | 5520 |

```
cagcgctttc tgaacgtagt agttggtgaa tttgtgaaca gatttggtgc agtcacggaa      5580
ttctttgttg ttaaccagcc agtagaaggt ctgaaccagg gtacggatcg ccaggtattc      5640
ctgcgcttta ttgaaagatt ccgcgaagtc tttacgaccc gcgaagtcga tgtcgtcctg      5700
gttgataccg atagattcgt ctttcagaga gtgaacagat tcaccgaaca ggaattcggt      5760
cgcagagtca acggtgaaac ggaagaacag ttcctggatg tcgaagtatt cacctttgtg      5820
tttcaggatg tgcttttca gcagctgaa gtgcggttcc agagaggtaa cgtgcgcaac      5880
ctgttcacgc gcgaactgcg gacgcagcat cgcgcgagag tgtttccaac cttcaccgtc      5940
cagggtgaag ataccgtcac ccagcagcgg cttgaacagg gtgtgacgtt acccagaga      6000 gaagtcaccg aactgggtcg ccaggatcgc tttgatgttt tccgggtctt tggtaacaac      6060
gatacgggta ccgaacagga tagaaacgta ggtaccaaca gacgggtttt tagagtggtc      6120
gaatttgtag tcgttgtatt cctgcgcacg accttctttt ttgaactgca gcgctttcca      6180
accgttaacg ataccgaacg cgttgtcgta cagtttgttg gtaaccggcg ccgcacccag      6240
ttttttcatc agaacgcggg ttttggtgta cgccagcagc tgtttgatga tgtacagaac      6300
cggaacaaca acgtaccagt attccagcag ttgttcgatc atgtcgctct ccgcaggcgc      6360
gccaagcata tggaattctc caatttttat taaattagtc gctacgagat ttaagacgta      6420
attttatgcc taactgagaa agttaagccg cccactctca ctctcgacat cttaaacctg      6480
agctaatcgg acgcttcgc caactacacc tacgggtagt ttttgctccg tcgtctgctg      6540
gaaaaacacg agctggccgc aagcatgcca ggtaccgcga gctactcgcg acggctgaaa      6600
gcaccgaaat gagcgagcta tctggtcgat tttgacccgg tgcccgtctt caaaatcggc      6660
gaaggccgaa gtcggccaga aatagcggcc tacttcagac cttccctagt aaatattttg      6720
caccaccgat catgccgact acacttaagt gtagttttaa tatttaacac cgtaacctat      6780
ggtgaaaatt tccagtcagc tggcgcgaga atagcataat gaaaataata ataaataatg      6840
atttcccggt cgctaaggtc ggagcggatc aaattacgac tctagtaagt gccaaagttc      6900
atagttgcat atatcggcca agattgagta tcgcggatgg agccgctccc agagtatgcc      6960
tttacagagc cccacctgga tatgggaaaa ccgttgctct tgcgttcgag tggctacgcc      7020
acagaacagc cggacgtcct gcagtgtggc tttctttaag agccagttct tacagtgaat      7080
ttgatatctg cgcagagatt attgagcagc ttgaaacttt cgaaatggta aaattcagcc      7140
gtgtgagaga gggtgtgagc aagcctgcgc tcttgcgaga ccttgcatct agtctttggc      7200
agagcacctc gaataacgag atagaaacgc tagtttgttt ggataatatt aatcatgact      7260
tagacttgcc gttgttgcac gcacttatgg agtttatgtt aaatacacca aaaaatatca      7320
ggtttgcagt tgcaggcaat acaataaaag ggttctcgca gcttaaactt gcaggcgcta      7380
tgcgggagta caccgagaaa gacttggcct ttagcgcaga agaggcggtg gcgttagcgg      7440
aggcagagtc tgttcttgga gttcctgaag aacagataga gaccttggtg caagaagttg      7500
aggggtggcc tgctcttgta gttttttgt taaagcgtga gttgccggcc aagcatattt      7560
cagcagtagt tgaagtagac aattacttta gggatgaaat atttgaggcg attcccgagc      7620
gctatcgtgt ttttcttgca aattcttcat tgctcgattt cgtgacgcct gatcaataca      7680
attatgtatt caaatgcgtc aatgggtct catgtattaa gtatttaagc actaattaca      7740
tgttgcttcg ccatgtgagc ggtgagccag cgcagtttac actgcatcca gtactgcgta      7800
attttctacg agaaattact tggactgaaa atcctgctaa aagatcctac ctgcttaagc      7860
```

```
gtgcagcttt ctggcattgg cgtagaggtg aataccagta tgcaatacga atatccctac    7920
gggcgaatga ctgtcgctgg gcagtcagca tgtctgagag aataatttta gatttgtcat    7980
ttcgtcaggg cgaaatagat gcgctgagac agtggctgtt agagctgccg aagcaggcct    8040
ggcaccaaaa acccatagtg cttattagtt acgcgtgggt attgtatttc agtcagcaag    8100
gcgcgcgagc agagaagtta attaaagacc tatcttcaca atccgataaa aaaataaat     8160 ggcaagaaaa ggaatggctg cagcttgtgc ttgcaatagg taaagcaacc aaagatgaaa    8220
tgctttcgag tgaggagctc tgtaataagt ggattagttt atttggggat tcaaacgcag    8280
ttggaaaagg ggccgcgcta acctgtttgg cttttatttt tgccagtgag tatagatttg    8340
cagagttgga gaaggtgctg gctcaggccc aagccgtgaa taaatttgca aaacaaaatt    8400
ttgcttttgg ttggctgtat gtcgcgaggt ttcaacaagc cctagcaagc ggaaaaatgg    8460
gctgggcgag gcagattata actcaagcac gcacagacag tcgcgcgcag atgatggaat    8520
ccgagtttac ttcgaaaatg tttgacgctc tagagcttga gttacattat gaattgcgct    8580
gcttggacac ctcagaagaa aagctctcca aaatttttaga gttcatttcc aatcacgggg   8640
tgacagacgt gttttttttcc gtatgccgtg ctgtgtcagc ttggcggctt ggaaggagtg   8700
acctaaatgg ctccattgag atattggagt gggcgaaggc gcatgcggtt gaaaaaaatc    8760
taccaagatt ggaagttatg agccaaattg agatctatca gcgcttagtc tgtcaaggca    8820
taacgggcat aaataattta aaaactcttg aagatcataa gattttctcc ggacagcact    8880 cagccccct aaaagcacgc ctgctgcttg ttcaatcact agtgctttcc cgagatcgga     8940
actttcatag tgccgcgcac agagcgttat tggctattca gcaagcccgt aaaattaacg    9000
cgggccagct ggaagtccgt ggattattgt gtttggccgg agcgcaggca ggtgccggtg    9060
atttaaaaaa ggctcagctt aacattgttt atgcagtgga gatagcaaaa cagcttcaat    9120
gctttcaaac agttcttgat gaagtatgtt taattgagcg aataataccg gcttcatgtg    9180
aagccttcac agcagttaat ttagatcaag cgattgggc ttttagtctt ccgcgaatag     9240
ttgagattgg aaagtccgca gagaataaag ctgacgcttt attgacacgg aagcagattg    9300
ctgtcttgag gcttgtaaaa gaggggtgct caaacaaaca aatagcaaca aatatgcatg    9360
tcaccgaaga tgctataaag tggcacatga ggaaaatatt tgccaccttg aatgtagtga    9420
atcgcacgca agcaacaatt gaagctgagc gtcaaggaat tatctaaaat aatcggcatt    9480
aagtgatata gtgaaaagta tactcgagct catagtccac gacgcccgtg attttgtagc    9540
cctggccgac ggccagcagg taggccgaca ggctcatgcc ggccgccgcc gccttttcct    9600
caatcgctct tcgttcgtct ggaaggcagt acaccttgat aggtgggctg cccttcctgg    9660
ttggcttggt ttcatcagcc atccgcttgc cctcatctgt tacgccggcg gtagccggcc    9720
agcctcgcag agcaggattc ccgttgagca ccgccaggtg cgaataaggg acagtgaaga    9780
aggaacaccc gctcgcgggt gggcctactt cacctatcct gcccggctga cgccgttgga    9840
tacaccaagg aaagtctaca cgaacccttt ggcaaaatcc tgtatatcgt gcgaaaaagg    9900
atggatatac cgaaaaaatc gctataatga ccccgaagca gggttatgca gcggaaaagc    9960
gctgcttccc tgctgttttg tggaatatct accgactgga acaggcaaa tgcaggaaat     10020 tactgaactg aggggacagg cgagagagga tcaatggcta tctggggac cgagggctgt    10080 cgctgcgcca aggcacgatt ggagatcccc tatgcggtgt gaaataccgc acagatgcgt    10140
aaggagaaaa taccgcatca ggcgctcttc cgcttcctcg ctcactgact cgctgcgctc    10200
ggtcgttcgg ctgcggcgag cggtatcagc tcactcaaag gcggtaatac ggttatccac    10260
```

```
agaatcaggg gataacgcag gaaagaacat gtgagcaaaa ggccagcaaa aggccaggaa    10320
ccgtaaaaag gccgcgttgc tggcgttttt ccataggctc cgccccctg acgagcatca     10380
caaaaatcga cgctcaagtc agaggtggcg aaacccgaca ggactataaa gataccaggc    10440
gtttccccct ggaagctccc tcgtgcgctc tcctgttccg accctgccgc ttaccggata    10500
cctgtccgcc tttctccctt cgggaagcgt ggcgctttct catagctcac gctgtaggta    10560
tctcagttcg gtgtaggtcg ttcgctccaa gctgggctgt gtgcacgaac cccccgttca    10620
gcccgaccgc tgcgccttat ccggtaacta tcgtcttgag tccaacccgg taagacacga    10680
cttatcgcca ctggcagcag ccactggtaa caggattagc agagcgaggt atgtaggcgg    10740
tgctacagag ttcttgaagt ggtggcctaa ctacggctac actagaagga cagtatttgg    10800
tatctgcgct ctgctgaagc cagttacctt cggaaaaaga gttggtagct cttgatccgg    10860
caaacaaacc accgctggta gcggtggttt ttttgtttgc aagcagcaga ttacgcgcag    10920
aaaaaaagga tctcaagaag atcctttgat cttttctacg gggtctgacg ctcagtggaa    10980
cgaaaactca cgttaaggga ttttggtcat gagattatca aaaaggatct tcacctagat    11040
ccttttaaat taaaaatgaa gttttaaatc aatctaaagt atatatgagt aaacttggtc    11100
tgacagttac caatcgattg gtcggtcatt tcgaacccca gagtcccgct cagaagaact    11160
cgtcaagaag gcgatagaag gcgatgcgct gcgaatcggg agcggcgata ccgtaaagca    11220
cgaggaagcg gtcagcccat tcgccgccaa gctcttcagc aatatcacgg gtagccaacg    11280
ctatgtcctg atagcggtcc gccacaccca gccggccaca gtcgatgaat ccagaaaagc    11340
ggccattttc caccatgata ttcggcaagc aggcatcgcc atgggtcacg acgagatcct    11400
cgccgtcggg catgcgcgcc ttgagcctgg cgaacagttc ggctggcgcg agccctgat     11460
gctcttcgtc cagatcatcc tgatcgacaa gaccggcttc catccgagta cgtgctcgct    11520
cgatgcgatg tttcgcttgg tggtcgaatg ggcaggtagc cggatcaagc gtatgcagcc    11580
gccgcattgc atcagccatg atggatactt tctcggcagg agcaaggtga gatgacagga    11640
gatcctgccc cggcacttcg cccaatagca gccagtccct tcccgcttca gtgacaacgt    11700
cgagcacagc tgcgcaagga acgcccgtcg tggccagcca cgatagccgc gctgcctcgt    11760
cctgcagttc attcagggca ccggacaggt cggtcttgac aaaaagaacc gggcgcccct    11820
gcgctgacag ccggaacacg gcggcatcag agcagccgat tgtctgttgt gcccagtcat    11880
agccgaatag cctctccacc caagcggccg gagaacctgc gtgcaatcca tcttgttcaa    11940
tcatgcgaaa cgatcctcat cctgtctctt gatcagatct tgatccctg cgccatcaga   12000
tccttggcgg caagaaagcc atccagttta ctttgcaggg cttccc                   12046
```

<210> SEQ ID NO 67
<211> LENGTH: 12
<212> TYPE: PRT
<213> ORGANISM: Artificial Sequence
<220> FEATURE:
<223> OTHER INFORMATION: Synthetic sequence motif from AlkL
<220> FEATURE:
<221> NAME/KEY: MOD_RES
<222> LOCATION: (2)..(2)
<223> OTHER INFORMATION: proteinogenic amino acid
<220> FEATURE:
<221> NAME/KEY: MOD_RES
<222> LOCATION: (7)..(7)
<223> OTHER INFORMATION: proteinogenic amino acid
<220> FEATURE:
<221> NAME/KEY: MOD_RES
<222> LOCATION: (9)..(9)

```
<223> OTHER INFORMATION: Val or Ala
<220> FEATURE:
<221> NAME/KEY: MOD_RES
<222> LOCATION: (11)..(11)
<223> OTHER INFORMATION: proteinogenic amino acid

<400> SEQUENCE: 67

Asp Xaa Trp Ala Pro Ala Xaa Gln Xaa Gly Xaa Arg
1               5                   10

<210> SEQ ID NO 68
<211> LENGTH: 698
<212> TYPE: PRT
<213> ORGANISM: Candida cloacae

<400> SEQUENCE: 68

Met Ser His Gln Val Glu Asp His Asp Leu Asp Val Phe Cys Leu Leu
1               5                   10                  15

Ala Asp Ala Val Leu His Glu Ile Pro Pro Ser Glu Ile Val Glu Tyr
            20                  25                  30

Leu His Pro Asp Phe Pro Lys Asp Lys Ile Glu Glu Tyr Leu Thr Gly
        35                  40                  45

Phe Ser Arg Pro Ser Ala Val Pro Gln Phe Arg Gln Cys Ala Lys Lys
    50                  55                  60

Leu Ile Asn Arg Gly Ser Glu Leu Ser Ile Lys Leu Phe Leu Tyr Leu
65                  70                  75                  80

Thr Thr Ala Leu Asp Ser Arg Ile Leu Ala Pro Ala Leu Thr Asn Ser
                85                  90                  95

Leu Thr Leu Ile Arg Asp Met Asp Leu Ser Gln Arg Glu Glu Leu Leu
            100                 105                 110

Arg Ser Trp Arg Asp Ser Pro Leu Thr Ala Lys Arg Arg Leu Phe Arg
        115                 120                 125

Val Tyr Ala Ser Phe Thr Leu Ser Thr Phe Asn Lys Leu Gly Thr Asp
    130                 135                 140

Leu His Phe Lys Ala Leu Gly Tyr Pro Gly Arg Glu Leu Arg Thr Gln
145                 150                 155                 160

Ile Gln Asp Tyr Glu Val Asp Pro Phe Arg Tyr Ser Phe Met Glu Lys
                165                 170                 175

Leu Lys His Glu Gly His Glu Leu Phe Leu Pro Asp Ile Asp Val Leu
            180                 185                 190

Ile Ile Gly Ser Gly Ser Gly Ala Gly Val Val Ala Gln Thr Leu Thr
        195                 200                 205

Glu Ser Gly Leu Lys Ser Leu Val Leu Glu Lys Gly Lys Tyr Phe Ala
    210                 215                 220

Ser Glu Glu Leu Cys Met Thr Asp Leu Asp Gly Asn Glu Ala Leu Phe
225                 230                 235                 240

Glu Ser Gly Gly Thr Ile Pro Ser Thr Asn Gln Gln Leu Phe Met Ile
                245                 250                 255

Ala Gly Ser Thr Phe Gly Gly Gly Ser Thr Val Asn Trp Ser Ala Cys
            260                 265                 270

Leu Lys Thr Pro Phe Lys Val Arg Lys Glu Trp Tyr Asp Asp Phe Gly
        275                 280                 285

Leu Asp Phe Val Ala Thr Gln Gln Tyr Asp Asp Cys Met Asp Tyr Val
    290                 295                 300

Trp Lys Lys Met Gly Ala Ser Thr Glu His Ile Glu His Ser Ala Ala
305                 310                 315                 320
```

```
Asn Ala Val Ile Met Asp Gly Ala Ala Lys Leu Gly Tyr Ala His Arg
                325                 330                 335

Ala Leu Glu Gln Asn Thr Gly Gly His Val His Asp Cys Gly Met Cys
            340                 345                 350

His Leu Gly Cys Arg Phe Gly Ile Lys Gln Gly Gly Val Asn Cys Trp
        355                 360                 365

Phe Arg Glu Pro Ser Glu Lys Gly Ser Lys Phe Met Glu Gln Val Val
    370                 375                 380

Val Glu Lys Ile Leu Gln His Lys Gly Lys Ala Thr Gly Ile Leu Cys
385                 390                 395                 400

Arg Asp Thr Glu Ser Gly Ile Lys Phe Lys Ile Thr Gly Pro Lys Lys
                405                 410                 415

Tyr Val Val Ser Gly Gly Ser Leu Gln Thr Pro Val Leu Leu Gln Lys
                420                 425                 430

Ser Gly Phe Lys Asn Lys His Ile Gly Ala Asn Leu Lys Leu His Pro
            435                 440                 445

Val Ser Val Ala Leu Gly Asp Phe Gly Asn Glu Val Asp Phe Glu Ala
        450                 455                 460

Tyr Lys Arg Pro Leu Met Thr Ala Val Cys Asn Ala Val Asp Asp Leu
465                 470                 475                 480

Asp Gly Lys Ala His Gly Thr Arg Ile Glu Ala Ile Leu His Ala Pro
                485                 490                 495

Tyr Val Thr Ala Pro Phe Tyr Pro Trp Gln Ser Gly Ala Gln Ala Arg
                500                 505                 510

Lys Asn Leu Leu Lys Tyr Lys Gln Thr Val Pro Leu Leu Leu Leu Ser
            515                 520                 525

Arg Asp Thr Ser Ser Gly Thr Val Thr Tyr Asp Lys Gln Lys Pro Asp
        530                 535                 540

Val Leu Val Val Asp Tyr Thr Val Asn Lys Phe Asp Arg Asn Ser Ile
545                 550                 555                 560

Leu Gln Gly Phe Leu Val Ala Ser Asp Ile Leu Tyr Ile Glu Gly Ala
                565                 570                 575

Lys Glu Ile Leu Ser Pro Gln Ala Trp Val Pro Thr Phe Lys Ser Asn
                580                 585                 590

Lys Pro Lys His Ala Arg Ser Ile Lys Asp Glu Asp Tyr Val Lys Trp
            595                 600                 605

Arg Glu Thr Val Ala Lys Ile Pro Phe Asp Ser Tyr Gly Ser Pro Tyr
        610                 615                 620

Gly Ser Ala His Gln Met Ser Ser Cys Arg Met Ser Gly Lys Gly Pro
625                 630                 635                 640

Gly Tyr Gly Ala Cys Asp Thr Lys Gly Arg Leu Phe Glu Cys Asn Asn
                645                 650                 655

Val Tyr Val Ala Asp Ala Ser Val Met Pro Thr Ala Ser Gly Val Asn
                660                 665                 670

Pro Met Ile Thr Thr Met Ala Phe Ala Arg His Val Ala Leu Cys Leu
            675                 680                 685

Ala Lys Asp Leu Gln Pro Gln Thr Lys Leu
690                 695
```